(12) United States Patent
Oliner

(10) Patent No.: US 7,521,053 B2
(45) Date of Patent: Apr. 21, 2009

(54) ANGIOPOIETIN-2 SPECIFIC BINDING AGENTS

(75) Inventor: Jonathan Daniel Oliner, Newbury Park, CA (US)

(73) Assignees: Amgen Inc., Thousand Oaks, CA (US); Medarex, Inc., Princeton, NJ (US)

( * ) Notice: Subject to any disclaimer, the term of this patent is extended or adjusted under 35 U.S.C. 154(b) by 697 days.

(21) Appl. No.: 10/269,805

(22) Filed: Oct. 10, 2002

(65) Prior Publication Data

US 2003/0124129 A1 Jul. 3, 2003

Related U.S. Application Data

(60) Provisional application No. 60/328,604, filed on Oct. 11, 2001.

(51) Int. Cl.
- *C07K 16/00* (2006.01)
- *C07K 16/30* (2006.01)
- *A61K 39/395* (2006.01)

(52) U.S. Cl. ............. 424/155.1; 530/387.7; 530/388.85

(58) Field of Classification Search ................ 530/300, 530/350; 424/155.1
See application file for complete search history.

(56) References Cited

U.S. PATENT DOCUMENTS

| | | | |
|---|---|---|---|
| 5,447,860 A | 9/1995 | Ziegler | |
| 5,521,073 A | 5/1996 | Davis et al. | |
| 5,562,903 A | 10/1996 | Co et al. | |
| 5,608,039 A * | 3/1997 | Pastan et al. | 530/387.3 |
| 5,639,641 A | 6/1997 | Pedersen et al. | |
| 5,643,755 A | 7/1997 | Davis et al. | |
| 5,650,490 A | 7/1997 | Davis et al. | |
| 5,681,722 A | 10/1997 | Newman et al. | |
| 5,744,580 A | 4/1998 | Better et al. | |
| 5,750,106 A * | 5/1998 | Ostberg | 424/142.1 |
| 5,770,196 A | 6/1998 | Studnicka | |
| 5,773,218 A | 6/1998 | Gallatin et al. | |
| 5,811,517 A | 9/1998 | Gallatin et al. | |
| 5,814,464 A | 9/1998 | Davis et al. | |
| 5,837,491 A | 11/1998 | Better et al. | |
| 5,837,822 A | 11/1998 | Gallatin et al. | |
| 5,879,672 A | 3/1999 | Davis et al. | |
| 5,889,157 A | 3/1999 | Pastan et al. | |
| 5,955,291 A | 9/1999 | Alitalo et al. | |
| 5,972,338 A | 10/1999 | Godowski et al. | |
| 5,977,319 A | 11/1999 | Pope et al. | |
| 5,977,322 A | 11/1999 | Marks et al. | |
| 5,981,726 A | 11/1999 | Pastan | |
| 6,030,831 A | 2/2000 | Godowski et al. | |
| 6,046,310 A | 4/2000 | Queen et al. | |
| 6,146,629 A | 11/2000 | Dagan | |
| 6,166,185 A | 12/2000 | Davis et al. | |
| RE39,586 E | 4/2001 | Dagan | |
| 6,287,562 B1 | 9/2001 | Pastan et al. | |
| 6,300,064 B1 | 10/2001 | Knappik et al. | |
| 6,455,035 B1 | 9/2002 | Suri et al. | |
| 6,777,540 B1 | 8/2004 | Okumura et al. | |
| 6,794,363 B2 | 9/2004 | Bejanin et al. | |
| 6,924,360 B2 | 8/2005 | Green et al. | |
| 7,067,131 B2 | 6/2006 | Gudas et al. | |
| 7,074,571 B2 | 7/2006 | Bejanin et al. | |
| 7,084,257 B2 | 8/2006 | Deshpande et al. | |
| 7,090,844 B2 | 8/2006 | Bar-Eli et al. | |
| 7,112,661 B1 | 9/2006 | Miller | |
| 7,135,174 B2 | 11/2006 | Corvalan et al. | |
| 7,138,501 B2 | 11/2006 | Ruben et al. | |
| 7,147,851 B1 | 12/2006 | Ponath et al. | |
| 7,179,892 B2 | 2/2007 | Basi et al. | |
| 7,193,064 B2 | 3/2007 | Mikayama et al. | |
| 7,193,069 B2 | 3/2007 | Isogai et al. | |
| 7,220,840 B2 | 5/2007 | Ruben et al. | |
| 7,241,444 B2 | 7/2007 | Goetsch et al. | |
| 7,250,166 B2 | 7/2007 | Drakenberg et al. | |
| 7,256,273 B2 | 8/2007 | Basi et al. | |
| 7,262,028 B2 | 8/2007 | Van Berkel et al. | |
| 2003/0082177 A1 | 5/2003 | Kalish | |

FOREIGN PATENT DOCUMENTS

| | | |
|---|---|---|
| EP | 0528767 | 2/1993 |
| EP | 0873363 | 10/1998 |
| EP | 0957166 | 11/1999 |
| EP | 1051620 | 11/2000 |
| EP | 1071458 | 1/2001 |
| EP | 1245676 | 10/2002 |
| EP | 1303303 | 4/2003 |
| EP | 1479696 | 11/2004 |
| JP | 2005160485 | 12/1991 |
| JP | 06153984 | 6/1994 |
| JP | 2000080100 | 3/2000 |
| JP | 2001507210 | 6/2001 |
| JP | 2001292787 | 10/2001 |
| JP | 2003531129 | 10/2003 |
| JP | 2004500847 | 1/2004 |
| JP | 2005500808 | 1/2005 |
| JP | 2005046143 | 2/2005 |

(Continued)

OTHER PUBLICATIONS

Paul, Fundamental Immunology, 3rd Edition, 1993, pp. 292-295.*

(Continued)

*Primary Examiner*—Brandon J Fetterolf
(74) *Attorney, Agent, or Firm*—McDonnell Boehnen Hulbert & Berghoff LLP

(57) ABSTRACT

Disclosed are specific binding agents, such as fully human antibodies, that bind to angiopoietin-2. Also disclosed are heavy chain fragments, light chain fragments, and CDRs of the antibodies, as well as methods of making and using the antibodies.

17 Claims, 4 Drawing Sheets

FOREIGN PATENT DOCUMENTS

| WO | WO 91/07492 | 5/1991 |
| --- | --- | --- |
| WO | WO 95/13387 | 5/1995 |
| WO | WO 95/21866 | 8/1995 |
| WO | WO9708320 | 3/1997 |
| WO | WO 98/05779 | 2/1998 |
| WO | WO9806248 | 2/1998 |
| WO | WO 98/18914 | 5/1998 |
| WO | WO 99/43801 | 9/1999 |
| WO | WO 00/06195 | 2/2000 |
| WO | WO 00/37504 | 6/2000 |
| WO | WO 00/57901 | 10/2000 |
| WO | WO 00/75323 | 12/2000 |
| WO | WO 00/77037 | 12/2000 |
| WO | WO0073430 | 12/2000 |
| WO | WO0127279 | 4/2001 |
| WO | WO0136642 | 5/2001 |
| WO | WO0157276 | 8/2001 |
| WO | WO0178779 | 10/2001 |
| WO | WO0186003 | 11/2001 |
| WO | WO0246237 | 6/2002 |
| WO | WO02087611 | 7/2002 |
| WO | WO02059260 | 8/2002 |
| WO | WO03002608 | 1/2003 |

OTHER PUBLICATIONS

Rudikoff et al (Proc. Natl. Acad. Sci. USA 1982 vol. 79: p. 1979.*
Coleman (Research in Immunology, 145:33-36, 1994.*
[Fundamental Immunology 242 (William E. Paul, M.D. ed., 3rd ed. 1993)].*
Connell et al. (2001), *Ashley Publications Ltd. ISSN* 1354-3776, pp. 1171-1203.
Coxon et al. (2002), "Inhibition of interleukin-1 but not tumor necrosis factor suppresses neovascularization in rat models of corneal angiogenesis and adjuvant arthritis," *Arthritis Rheum.* 46:2604-2612.
Feige et al. (2000), "Anti-interleukin-1 and anti-tumor necrosis factor-α synergistically inhibit adjuvant arthritis in Lewis rats," *Cell Mol. Life Sci.* 57:1457-1470.
Peacock et al. (1992), "Angiogenesis inhibition suppresses collagen arthritis," *J. Exp. Med.* 175:1135-1138.
Peacock et al. (1995), "A novel angiogenesis inhibitor suppresses rat adjuvant arthritis," *Cell Immunol.* 160:178-184.
Walsh et al. (2001), "Angiogenesis in the pathogenesis of inflammatory joint and lung diseases," *Arthritis Res.* 3:147-153.
Coxon A. et al., "Inhibition of Interleukin-1 but Not Tumor Necrosis Factor Suppresses Neovascularization in Rat Models of Cornmeal Angiogenesis and Adjuvant Arthritis," Arthritis & Rheumatism, vol. 46(10) p. 2604-2612 (2002).
Feige U. et al., "Anti-Interleukin-1 and anti-tumor necrosis factor-α synergistically inhibit adjuvant arthritis in Lewis rats," CMLS, vol. 57, p. 1457-1470 (2000).
Peacock J.D. et al., "Angiogenesis inhibiton Suppresses Collagen Arthritis" J. Exp. Med., vol. 175, p. 1135-38 (1992).
Peacock J.D. et al. "A Novel Angiogenesis Inhibitor Suppresses Rat Adjuvant Arthritis," Cellular Immunology, vol. 160, p. 178-184 (1995).
Walsh D. et al., "Angiogenesis in the pathogenesis of inflammatory joint and lung diseases," Arthritis Research, vol. 3(3), p. 147-153 (2001).
Oliner J. et al., "Suppression of Angiogenesis and Tumor Growth by selective inhibition of angiopoietin-2," Cancer Cell, vol. 6(5), p. 507-516 (2004).
Ahmad S.A. et al., "Differential Expression of Angiopoietin-1 and Angiopoietin-2 in Colon Carcinoma. A Possible Mechanism for the Installation of Angiogenesis," Cancer, vol. 92(5), p. 1138-1143 (2001).

* cited by examiner

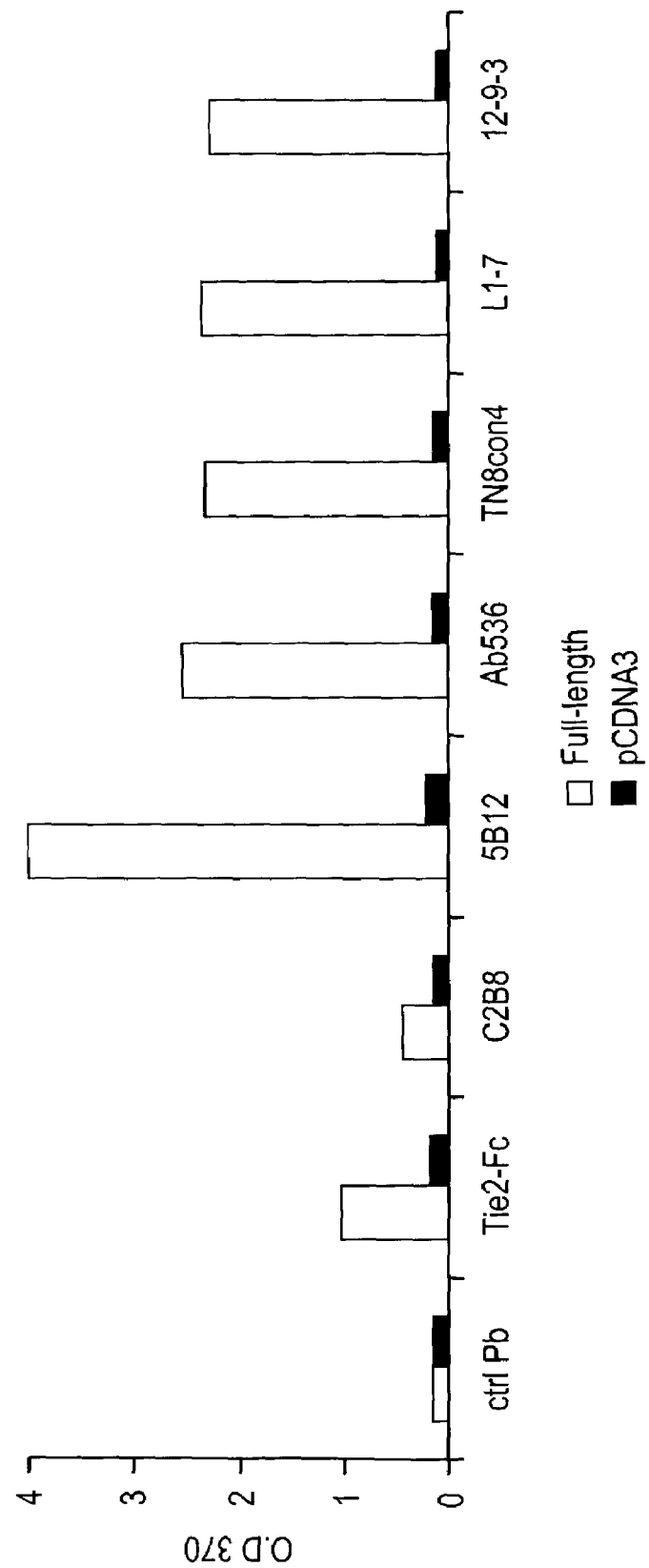

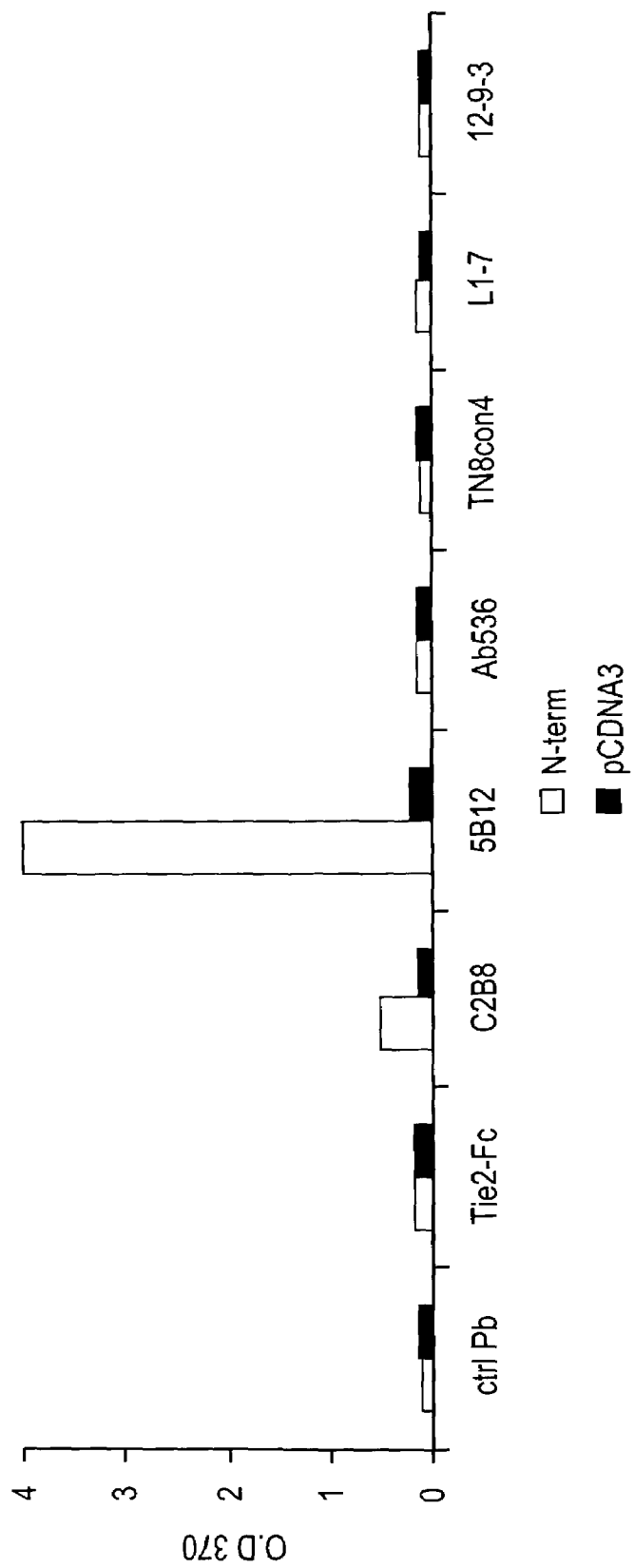

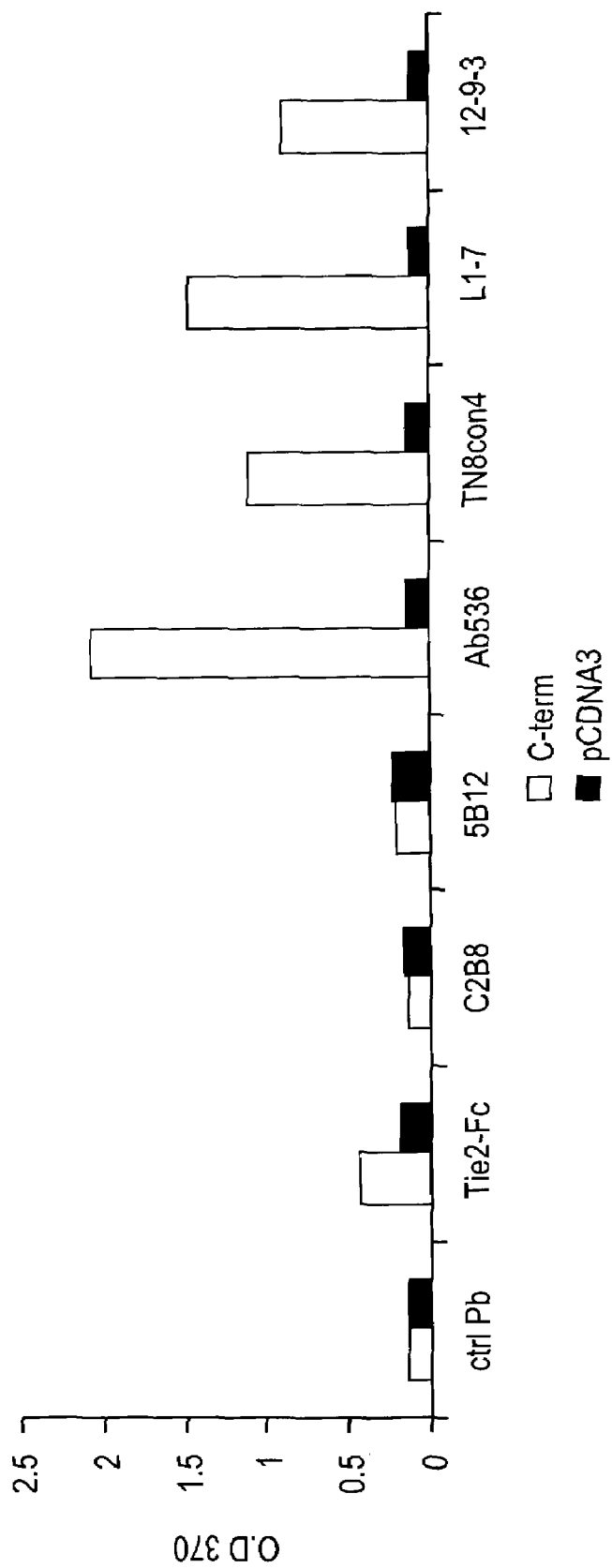

SEQUENCE LISTING

```
<160> NUMBER OF SEQ ID NOS: 76
<210> SEQ ID NO 1
<211> LENGTH: 123
<212> TYPE: PRT
<213> ORGANISM: Homo sapiens

<400> SEQUENCE: 1

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Asp Tyr Asp Ile Leu Thr Gly Pro Tyr Ala Tyr
                100                 105                 110

Trp Gly Gln Gly Thr Leu Val Thr Val Ser Ser
            115                 120

<210> SEQ ID NO 2
<211> LENGTH: 112
<212> TYPE: PRT
<213> ORGANISM: Homo sapiens

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Thr Phe Gly Gly Gly Thr Lys Val Glu Ile Lys
                100                 105                 110

<210> SEQ ID NO 3
<211> LENGTH: 123
<212> TYPE: PRT
<213> ORGANISM: Homo sapiens

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
```

```
                35                  40                  45
Gly Gly Ile Ile Pro Ile Phe Gly Thr Ala Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Val Val Gly Asp Phe Asp Trp Leu Ser Phe Phe Asp Tyr
             100                 105                 110

Trp Gly Gln Gly Thr Leu Val Thr Val Ser Ser
             115                 120

<210> SEQ ID NO 4
<211> LENGTH: 107
<212> TYPE: PRT
<213> ORGANISM: Homo sapiens

<400> SEQUENCE: 4

Ser Tyr Glu Leu Thr Gln Pro Pro Ser Val Ser Val Ser Pro Gly Gln
 1               5                  10                  15

Thr Ala Ser Ile Thr Cys Ser Gly Asp Lys Leu Gly Tyr Thr Tyr Thr
             20                  25                  30

Ser Trp Phe Gln Gln Lys Pro Gly Gln Ser Pro Val Leu Val Ile Phe
         35                  40                  45

Gln Asp Phe Lys Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Thr Thr Ala Val
                 85                  90                  95

Val Phe Gly Thr Gly Thr Lys Val Thr Val Leu
             100                 105

<210> SEQ ID NO 5
<211> LENGTH: 120
<212> TYPE: PRT
<213> ORGANISM: Homo sapiens

<400> SEQUENCE: 5

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Leu Gly Ile Ala Asn Tyr Ala Gln Lys Phe
     50                  55                  60

Gln Gly Arg Val Thr Ile Thr Ala Asp Lys Ser Thr Asn Thr Ala Tyr
 65                  70                  75                  80

Met Glu Leu Thr Ser Leu Thr Ser Asp Asp Thr Ala Val Tyr Tyr Cys
                 85                  90                  95

Ala Arg Asp Arg Glu Asp Thr Ala Met Val Phe Asn Tyr Trp Gly Gln
             100                 105                 110

Gly Thr Leu Val Thr Val Ser Ser
         115                 120
```

```
<210> SEQ ID NO 6
<211> LENGTH: 111
<212> TYPE: PRT
<213> ORGANISM: Homo sapiens

<400> SEQUENCE: 6

Gln Ser Val Leu Thr Gln Pro Pro Ser Val Ser Ala Ala Pro Gly Gln
 1               5                  10                  15

Lys Val Thr Val Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Phe Trp Val Phe Gly Gly Gly Thr Lys Leu Thr Val Leu
            100                 105                 110

<210> SEQ ID NO 7
<211> LENGTH: 122
<212> TYPE: PRT
<213> ORGANISM: Homo sapiens

<400> SEQUENCE: 7

Glu Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Asp Tyr Asp Ile Leu Thr Gly Tyr Gly Tyr Trp
            100                 105                 110

Gly Gln Gly Thr Leu Val Thr Val Ser Ser
        115                 120

<210> SEQ ID NO 8
<211> LENGTH: 106
<212> TYPE: PRT
<213> ORGANISM: Homo sapiens

<400> SEQUENCE: 8

Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60
```

```
Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser His Val Val
                 85                  90                  95

Phe Gly Gly Gly Thr Lys Leu Thr Val Leu
            100                 105
```

<210> SEQ ID NO 9
<211> LENGTH: 121
<212> TYPE: PRT
<213> ORGANISM: Homo sapiens

<400> SEQUENCE: 9

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ala Phe Ser Pro Phe Thr Glu Thr Asp Ala Phe Asp Ile Trp Gly
             100                 105                 110

Gln Gly Thr Met Val Thr Val Ser Ser
        115                 120
```

<210> SEQ ID NO 10
<211> LENGTH: 112
<212> TYPE: PRT
<213> ORGANISM: Homo sapiens

<400> SEQUENCE: 10

```
Gln Ser Val Leu Thr Gln Pro Pro Ser Val Ser Ala Ala Pro Gly Gln
 1               5                  10                  15

Lys Val Thr Ile Ser Cys Ser Gly Ser Asn Ser Asn Ile Gly Asn Asn
                 20                  25                  30

Phe Val Ser Trp Tyr Gln Gln Leu Pro Gly Thr Ala Pro Lys Leu Leu
             35                  40                  45

Val Tyr Asp Asn Asn Lys Arg Pro Ser Gly Ile Pro Asp Arg Phe Ser
     50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Ala Glu Val Val Phe Gly Gly Gly Thr Lys Leu Thr Val Leu
             100                 105                 110
```

<210> SEQ ID NO 11
<211> LENGTH: 122
<212> TYPE: PRT
<213> ORGANISM: Homo sapiens

<400> SEQUENCE: 11

```
Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Asp Tyr Asp Ile Leu Thr Gly Tyr Gly Tyr Trp
            100                 105                 110

Gly Gln Gly Thr Leu Val Thr Val Ser Ser
            115                 120
```

<210> SEQ ID NO 12
<211> LENGTH: 112
<212> TYPE: PRT
<213> ORGANISM: Homo sapiens

<400> SEQUENCE: 12

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gln Gly Thr Lys Leu Glu Ile Lys
            100                 105                 110
```

<210> SEQ ID NO 13
<211> LENGTH: 119
<212> TYPE: PRT
<213> ORGANISM: Homo sapiens

<400> SEQUENCE: 13

```
Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Gly Leu Gly Ser Glu Asp Thr Ala Val Tyr Tyr Cys
                85                  90                  95
```

```
Ala Arg Gly Ser Ser Asp Ala Ala Val Ala Gly Met Trp Gly Gln Gly
            100                 105                 110

Thr Leu Val Thr Val Ser Ser
            115

<210> SEQ ID NO 14
<211> LENGTH: 111
<212> TYPE: PRT
<213> ORGANISM: Homo sapiens

<400> SEQUENCE: 14

Gln Ser Val Leu Thr Gln Pro Pro Ser Val Ser Ala Ala Pro Gly Gln
1               5                   10                  15

Asp Val Thr Ile Ser Cys Ser Gly Asn Asn Ser Asn Ile Gly Asn Asn
            20                  25                  30

Tyr Val Ser Trp Tyr Gln Gln Val Pro Gly Thr Ala Pro Lys Leu Leu
        35                  40                  45

Val Tyr Asp Asn His Lys Arg Pro Ser Gly Ile Ser Asp Arg Phe Ser
50                  55                  60

Gly Ser Lys Ser Asp Thr Ser Ala Thr Leu Asp Ile Thr Gly Leu Gln
65                  70                  75                  80

Pro Gly Asp Glu Ala Asp Tyr Tyr Cys Gly Thr Trp Asp Thr Ser Leu
                85                  90                  95

Ser Ala Asn Trp Val Phe Gly Gly Gly Thr Lys Leu Thr Val Leu
            100                 105                 110

<210> SEQ ID NO 15
<211> LENGTH: 120
<212> TYPE: PRT
<213> ORGANISM: Homo sapiens

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
50                  55                  60

Gln Gly Arg Val Thr Ile Thr Ala Asp Lys Phe Thr Ser Thr Ala Tyr
65                  70                  75                  80

Met Glu Leu Ser Ser Leu Gly Ser Glu Asp Thr Ala Val Tyr Tyr Cys
                85                  90                  95

Ala Arg Ala Val Pro Gly Thr Glu Asp Ala Phe Asp Ile Trp Gly Gln
            100                 105                 110

Gly Thr Met Val Thr Val Ser Ser
            115                 120

<210> SEQ ID NO 16
<211> LENGTH: 111
<212> TYPE: PRT
<213> ORGANISM: Homo sapiens

<400> SEQUENCE: 16

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Ala Asn
```

```
                  20                  25                  30

Tyr Val Ser Trp Tyr Gln Gln Leu Pro Gly Thr Ala Pro Lys Leu Leu
             35                  40                  45

Ile Tyr Asn Asn Asn Lys Arg Pro Ser Gly Ile Pro Asp Arg Phe Ser
 50                  55                  60

Gly Ser Lys Ser Asp Thr Ser Ala Thr Leu Gly Ile Thr Gly Leu Gln
 65                  70                  75                  80

Thr Gly Asp Glu Ala Asp Tyr Tyr Cys Gly Ala Trp Asp Ser Ser Leu
                 85                  90                  95

Ser Ala Ser Trp Val Phe Gly Gly Gly Thr Lys Leu Thr Val Leu
            100                 105                 110

<210> SEQ ID NO 17
<211> LENGTH: 123
<212> TYPE: PRT
<213> ORGANISM: Homo sapiens

<400> SEQUENCE: 17

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
             35                  40                  45

Gly Arg Ile Ile Pro Ile Leu Gly Ile Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Pro Tyr Tyr Asp Phe Trp Ser Gly Pro Gly Gly Met Asp Val
            100                 105                 110

Trp Gly Gln Gly Thr Thr Val Thr Val Ser Ser
        115                 120

<210> SEQ ID NO 18
<211> LENGTH: 112
<212> TYPE: PRT
<213> ORGANISM: Homo sapiens

<400> SEQUENCE: 18

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
            100                 105                 110
```

<210> SEQ ID NO 19
<211> LENGTH: 121
<212> TYPE: PRT
<213> ORGANISM: Homo sapiens

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Glu Ser Gly Tyr Trp Gly Asp Ala Phe Asp Ile Trp Gly
            100                 105                 110

Gln Gly Thr Met Val Thr Val Ser Ser
        115                 120

<210> SEQ ID NO 20
<211> LENGTH: 112
<212> TYPE: PRT
<213> ORGANISM: Homo sapiens

<400> SEQUENCE: 20

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asn Trp Tyr Leu Gln Lys Pro Gly Gln Ser
        35                  40                  45

Pro Gln Ile Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Thr Pro Pro Thr Phe Gly Gln Gly Thr Lys Leu Glu Ile Lys
            100                 105                 110

<210> SEQ ID NO 21
<211> LENGTH: 123
<212> TYPE: PRT
<213> ORGANISM: Homo sapiens

<400> SEQUENCE: 21

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Pro Val Asp Phe Asp Tyr Gly Asp Tyr Ala Ile Asp Tyr
            100                 105                 110

Trp Gly Gln Gly Thr Leu Val Thr Val Ser Ser
        115                 120

<210> SEQ ID NO 22
<211> LENGTH: 111
<212> TYPE: PRT
<213> ORGANISM: Homo sapiens

<400> SEQUENCE: 22

Gln Ser Val Leu Thr Gln Pro Ser Ser Val Ser Gly Ala Pro Gly Gln
 1               5                  10                  15

Arg Val Thr Ile Ser Cys Thr Gly Gln Ser Ser Asn Ile Gly Ala Gly
             20                  25                  30

Tyr Asp Val His Trp Tyr Gln Gln Phe Pro Gly Arg Ala Pro Lys Leu
         35                  40                  45

Leu Ile Tyr Gly Asn Ser Asn Arg Pro Ser Gly Val Pro Asp Arg Phe
     50                  55                  60

Ser Gly Ser Lys Ser Gly Thr Ser Ala Ser Leu Ala Ile Thr Gly Leu
 65                  70                  75                  80

Gln Pro Glu Asp Glu Ala Asp Tyr Tyr Cys Gln Ser Tyr Asp Ser Arg
                 85                  90                  95

Leu Ser Gly Ser Val Phe Gly Gly Gly Thr Lys Leu Thr Val Leu
            100                 105                 110

<210> SEQ ID NO 23
<211> LENGTH: 123
<212> TYPE: PRT
<213> ORGANISM: Homo sapiens

<400> SEQUENCE: 23

Glu Val Gln Leu Val Asp Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Thr Ile Ser Phe Thr Phe Ser Gly Tyr Phe Asp Tyr
            100                 105                 110

Trp Ala Gln Gly Thr Leu Val Thr Val Ser Ser
        115                 120

<210> SEQ ID NO 24
<211> LENGTH: 110
<212> TYPE: PRT
<213> ORGANISM: Homo sapiens
```

```
<400> SEQUENCE: 24

Gln Ser Val Leu Thr Gln Pro Ser Ser Val Ser Glu Ala Pro Arg Gln
1               5                   10                  15

Arg Val Thr Ile Ser Cys Ser Gly Ser Ala Ser Asn Ile Gly Ala Asn
                20                  25                  30

Gly Val Ser Trp Tyr His Gln Val Pro Gly Lys Ala Pro Arg Leu Leu
            35                  40                  45

Leu Ser His Asp Gly Leu Val Thr Ser Gly Val Pro Asp Arg Leu Ser
    50                  55                  60

Val Ser Lys Ser Gly Thr Ser Ala Ser Leu Ala Ile Ser Gly Leu His
65                  70                  75                  80

Ser Asp Asp Glu Gly Asp Tyr Tyr Cys Ala Val Trp Asp Asp Ser Leu
                85                  90                  95

Asn Ala Val Val Phe Gly Gly Gly Thr Lys Leu Thr Val Leu
                100                 105                 110

<210> SEQ ID NO 25
<211> LENGTH: 124
<212> TYPE: PRT
<213> ORGANISM: Homo sapiens

<400> SEQUENCE: 25

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Phe Trp Ser Gly Tyr Ser Leu Asp Ala Phe Asp
                100                 105                 110

Ile Trp Gly Gln Gly Thr Met Val Thr Val Ser Ser
            115                 120

<210> SEQ ID NO 26
<211> LENGTH: 112
<212> TYPE: PRT
<213> ORGANISM: Homo sapiens

<400> SEQUENCE: 26

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 27
<211> LENGTH: 123
<212> TYPE: PRT
<213> ORGANISM: Homo sapiens

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Gly Leu Arg Ser Glu Asp Thr Ala Val Tyr Tyr Cys
                85                  90                  95

Ala Arg Gly Val Asp Asp Tyr Gly Gly Asn Ser Trp Ala Phe Asp Ile
            100                 105                 110

Trp Gly Gln Gly Thr Met Val Thr Val Ser Ser
        115                 120

<210> SEQ ID NO 28
<211> LENGTH: 112
<212> TYPE: PRT
<213> ORGANISM: Homo sapiens

<400> SEQUENCE: 28

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Thr Gly Ser Gly Ser Ala Thr Asp Phe Thr Leu Arg Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 29
<211> LENGTH: 128
<212> TYPE: PRT
<213> ORGANISM: Homo sapiens

<400> SEQUENCE: 29

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
```

```
                20                  25                  30
Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Ala Ser Asp His Tyr Tyr Asp Ser Ser Gly Tyr Tyr Ser
            100                 105                 110

Asp Ala Phe Asp Ile Trp Gly Gln Gly Thr Met Val Thr Val Ser Ser
        115                 120                 125

<210> SEQ ID NO 30
<211> LENGTH: 112
<212> TYPE: PRT
<213> ORGANISM: Homo sapiens

<400> SEQUENCE: 30

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Ala Ser Asn Arg Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Met Gln Thr
                85                  90                  95

Leu Gln Ile Pro Ile Thr Phe Gly Pro Gly Thr Lys Val Asp Ile Lys
            100                 105                 110

<210> SEQ ID NO 31
<211> LENGTH: 123
<212> TYPE: PRT
<213> ORGANISM: Homo sapiens

<400> SEQUENCE: 31

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Gly Lys Gly Leu Glu Trp Ile
         35                 40                  45

Gly Glu Ile Asn His Ser Gly Ser Thr Asn Phe Asn Pro Ser Leu Lys
    50                  55                  60

Ser Arg Ile Thr Ile Ser Val Asp Thr Ser Asn Asn Gln Phe Ser Leu
65                  70                  75                  80

Lys Leu Ser Ser Val Thr Ala Ala Asp Thr Ala Ala Tyr Tyr Cys Ala
                85                  90                  95

Arg Gly His Asp Trp Gly Met Gly Ile Gly Gly Ala Tyr Asp Ile
            100                 105                 110

Trp Gly Gln Gly Thr Met Val Thr Val Ser Ser
```

-continued

```
                115                 120

<210> SEQ ID NO 32
<211> LENGTH: 108
<212> TYPE: PRT
<213> ORGANISM: Homo sapiens

<400> SEQUENCE: 32

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Leu Ala Trp Tyr Gln Gln Lys Pro Gly Gln Ala Pro Arg Leu Leu
        35                  40                  45

Val Tyr Ala Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Ser Pro
                85                  90                  95

Arg Thr Phe Gly Gln Gly Thr Lys Val Glu Ile Lys
            100                 105

<210> SEQ ID NO 33
<211> LENGTH: 122
<212> TYPE: PRT
<213> ORGANISM: Homo sapiens

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Ser
            20                  25                  30

Ser Met His Trp Val Arg Gln Ala Pro Gly Lys Gly Leu Glu Trp Met
        35                  40                  45

Gly Gly Phe Asp Pro Glu His Gly Glu Thr Ile Tyr Ala Gln Lys Phe
    50                  55                  60

Gln Gly Arg Leu Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Phe Cys
                85                  90                  95

Ala Arg Gly Val Gln Val Thr Ser Gly Tyr His Tyr Phe Asp His Trp
            100                 105                 110

Gly Gln Gly Thr Leu Val Thr Val Ser Ser
        115                 120

<210> SEQ ID NO 34
<211> LENGTH: 110
<212> TYPE: PRT
<213> ORGANISM: Homo sapiens

<400> SEQUENCE: 34

Gln Ser Ala Leu Thr Gln Pro Pro Ser Ala Ser Gly Ser Pro Gly Gln
1               5                   10                  15

Ser Ile Thr Ile Ser Cys Thr Gly Thr Asn Ser Asp Ile Gly Ser Tyr
            20                  25                  30

Pro Phe Val Ser Trp Tyr Gln Arg His Pro Gly Lys Ala Pro Lys Leu
        35                  40                  45
```

```
Leu Ile Tyr Asp Val Ser Asn Arg Pro Ser Gly Val Ser Asp Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Gly Asp Tyr Tyr Cys Ser Ser Phe Thr Met Asn
                 85                  90                  95

Ser Phe Val Ile Phe Gly Gly Thr Lys Leu Thr Val Leu
            100                 105                 110

<210> SEQ ID NO 35
<211> LENGTH: 125
<212> TYPE: PRT
<213> ORGANISM: Homo sapiens

<400> SEQUENCE: 35

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Pro Ile Tyr Tyr Asp Ile Leu Thr Gly Ile Asp Ala Phe
            100                 105                 110

Asp Ile Trp Gly Gln Gly Thr Met Val Thr Val Ser Ser
            115                 120                 125

<210> SEQ ID NO 36
<211> LENGTH: 108
<212> TYPE: PRT
<213> ORGANISM: Homo sapiens

<400> SEQUENCE: 36

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Ser Leu Ala Trp Tyr Gln Gln Lys Pro Gly Gln Ala Pro Arg Leu Leu
             35                  40                  45

Val Tyr Ala Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln His Tyr Gly Ser Ser Pro
                 85                  90                  95

Arg Thr Phe Gly Gln Gly Thr Lys Val Glu Ile Lys
            100                 105

<210> SEQ ID NO 37
<211> LENGTH: 120
<212> TYPE: PRT
<213> ORGANISM: Homo sapiens
```

```
<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Ile Pro Ser Gly Trp Tyr Phe Asp Leu Trp Gly Arg
                100                 105                 110

Gly Thr Leu Val Thr Val Ser Ser
                115                 120

<210> SEQ ID NO 38
<211> LENGTH: 110
<212> TYPE: PRT
<213> ORGANISM: Homo sapiens

<400> SEQUENCE: 38

Gln Ser Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
                20                  25                  30

Ala Val Asn Trp Tyr Gln Gln Leu Pro Gly Lys Ala Pro Lys Leu Leu
            35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Ser Gly Trp Val Phe Gly Gly Gly Thr Lys Leu Thr Val Leu
                100                 105                 110

<210> SEQ ID NO 39
<211> LENGTH: 122
<212> TYPE: PRT
<213> ORGANISM: Homo sapiens

<400> SEQUENCE: 39

Gln Val Gln Leu Val Glu Ser Gly Gly Gly Leu Val Lys Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Glu Val Gly Asn Tyr Tyr Asp Ser Ser Gly Tyr Gly Tyr Trp
            100                 105                 110

Gly Gln Gly Thr Leu Val Thr Val Ser Ser
        115                 120
```

<210> SEQ ID NO 40
<211> LENGTH: 110
<212> TYPE: PRT
<213> ORGANISM: Homo sapiens

<400> SEQUENCE: 40

```
Asn Phe Met Leu Thr Gln Pro His Ser Val Ser Glu Ser Pro Gly Lys
1               5                   10                  15

Thr Val Thr Ile Ser Cys Thr Arg Ser Gly Gly Ile Gly Ser Ser
            20                  25                  30

Phe Val His Trp Phe Gln Gln Arg Pro Gly Ser Ser Pro Thr Thr Val
            35                  40                  45

Ile Phe Asp Asp Asn Gln Arg Pro Thr Gly Val Pro Asp Arg Phe Ser
        50                  55                  60

Ala Ala Ile Asp Thr Ser Ser Ser Ala Ser Leu Thr Ile Ser Gly
65                  70                  75                  80

Leu Thr Ala Glu Asp Glu Ala Asp Tyr Tyr Cys Gln Ser Ser His Ser
                85                  90                  95

Thr Ala Val Val Phe Gly Gly Thr Lys Leu Thr Val Leu
            100                 105                 110
```

<210> SEQ ID NO 41
<211> LENGTH: 122
<212> TYPE: PRT
<213> ORGANISM: Homo sapiens

<400> SEQUENCE: 41

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Thr Val Ser Ser Asn
            20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Ser Asp Tyr Ala
        50                  55                  60

Val Ser Leu Arg Gly Arg Ile Thr Ile Asn Leu Asp Thr Asp Thr Ser
65                  70                  75                  80

Lys Asn Gln Phe Ser Leu Gln Leu Asn Ser Val Thr Pro Glu Asp Thr
                85                  90                  95

Ala Val Tyr Tyr Cys Ala Arg Asp Arg Gly Tyr Ile Asp Ser Trp
            100                 105                 110

Gly Gln Gly Thr Leu Val Thr Val Ser Ser
        115                 120
```

<210> SEQ ID NO 42
<211> LENGTH: 110
<212> TYPE: PRT
<213> ORGANISM: Homo sapiens

<400> SEQUENCE: 42

```
Asn Phe Met Leu Thr Gln Pro His Ser Val Ser Glu Ser Pro Gly Lys
```

```
1               5                   10                  15
Thr Val Thr Ile Ser Cys Thr Arg Ser Ser Gly Ser Ile Ala Thr Asn
                    20                  25                  30

Tyr Val Gln Trp Tyr Gln Gln Arg Pro Gly Ser Ser Pro Ala Thr Val
                35                  40                  45

Ile Tyr Glu Asp Asn Gln Arg Pro Ser Gly Val Pro Asp Arg Phe Ser
            50                  55                  60

Gly Ser Ile Asp Thr Ser Ser Asn Ser Ala Ser Leu Thr Ile Ser Gly
65                  70                  75                  80

Leu Thr Thr Glu Asp Glu Ala Asp Tyr Phe Cys Gln Ser Tyr Gly Asp
                    85                  90                  95

Asn Asn Trp Val Phe Gly Gly Gly Thr Lys Leu Thr Val Leu
                100                 105                 110

<210> SEQ ID NO 43
<211> LENGTH: 122
<212> TYPE: PRT
<213> ORGANISM: Homo sapiens

<400> SEQUENCE: 43

Glu Val Gln Leu Val Glu Ser Gly Gly Gly Leu Gly Gln Pro Gly Gly
1               5                   10                  15

Ser Leu Arg Leu Ser Cys Ala Ala Thr Gly Phe Ser Leu Asp Asp Tyr
                20                  25                  30

Glu Met Asn Trp Val Arg Gln Ala Pro Gly Arg Gly Leu Glu Trp Val
                35                  40                  45

Ser Tyr Ile Ile Gly Ser Gly Lys Thr Ile Phe Tyr Ala Asp Ser Val
            50                  55                  60

Lys Gly Arg Phe Thr Ile Ser Arg Asp Asn Gly Lys Asn Ser Val Tyr
65                  70                  75                  80

Leu Gln Met Asn Ser Leu Arg Ala Glu Asp Thr Ala Ile Tyr Tyr Cys
                    85                  90                  95

Ala Arg Gly Gly Gly Ser Ala Tyr Tyr Leu Asn Thr Ser Asp Ile Trp
                100                 105                 110

Gly Gln Gly Thr Met Val Thr Val Ser Ser
                115                 120

<210> SEQ ID NO 44
<211> LENGTH: 112
<212> TYPE: PRT
<213> ORGANISM: Homo sapiens

<400> SEQUENCE: 44

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Lys Gly Asp Asn Tyr Leu Asp Trp Tyr Leu Gln Lys Pro Gly Gln Ser
            35                  40                  45

Pro Gln Leu Leu Ile Tyr Leu Gly Ser His Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                    85                  90                  95

Leu Gln Thr Pro Leu Thr Phe Gly Gly Gly Thr Lys Val Glu Ile Lys
```

<210> SEQ ID NO 45
<211> LENGTH: 125
<212> TYPE: PRT
<213> ORGANISM: Homo sapiens

<400> SEQUENCE: 45

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Asn Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Arg Gly Ile Ala Ala Arg Ser Ala Tyr Tyr Tyr Gly Met
            100                 105                 110
Asp Val Trp Gly Gln Gly Thr Thr Val Thr Val Ser Ser
        115                 120                 125
```

<210> SEQ ID NO 46
<211> LENGTH: 113
<212> TYPE: PRT
<213> ORGANISM: Homo sapiens

<400> SEQUENCE: 46

```
Asp Ile Val Met Thr Gln Thr Pro Leu Ser Leu Pro Val Thr Pro Gly
1               5                   10                  15
Glu Pro Ala Ser Ile Ser Cys Arg Ser Ser Gln Ser Leu Leu Asp Ser
            20                  25                  30
Asp Asp Gly Lys Thr Tyr Leu Asp Trp Tyr Leu Gln Arg Pro Gly Gln
        35                  40                  45
Ser Pro Gln Leu Leu Met Tyr Thr Thr Ser Ser Arg Ala Ser Gly Val
    50                  55                  60
Pro Asp Arg Phe Ser Gly Ser Gly Ser Gly Thr Asp Phe Thr Leu Lys
65                  70                  75                  80
Ile Ser Arg Val Glu Ala Glu Asp Val Gly Val Tyr Tyr Cys Met Gln
                85                  90                  95
Ala Thr Gln Phe Pro Tyr Thr Phe Gly Gln Gly Thr Lys Leu Glu Ile
            100                 105                 110
Lys
```

<210> SEQ ID NO 47
<211> LENGTH: 120
<212> TYPE: PRT
<213> ORGANISM: Homo sapiens

<400> SEQUENCE: 47

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
```

```
Asp Leu Asn Trp Val Arg Gln Ala Ser Gly Gln Gly Leu Glu Trp Met
            35                  40                  45

Gly Trp Met Asn Pro Thr Ser Gly Asn Thr Gly Tyr Ala Gln Lys Phe
 50                  55                  60

Gln Gly Arg Ile Thr Met Thr Arg Asn Thr Ser Ile Ser Thr Ala Tyr
 65                  70                  75                  80

Met Glu Leu Arg Ser Leu Arg Ser Asp Thr Ala Val Tyr Tyr Cys
                85                  90                  95

Ala Arg Asp Pro Pro Ser Gly Gly Trp Glu Phe Asp Tyr Trp Gly Gln
            100                 105                 110

Gly Thr Leu Val Thr Val Ser Ser
            115                 120
```

<210> SEQ ID NO 48
<211> LENGTH: 112
<212> TYPE: PRT
<213> ORGANISM: Homo sapiens

<400> SEQUENCE: 48

```
Asp Ile Val Met Thr Gln Thr Pro Leu Ser Ser Thr Val Thr Leu Gly
 1               5                  10                  15

Gln Pro Ala Ser Ile Ser Cys Arg Ser Ser Gln Ser Leu Val His Glu
            20                  25                  30

Asp Gly Asn Thr Tyr Leu Asn Trp Leu His Gln Arg Pro Gly Gln Pro
        35                  40                  45

Pro Arg Leu Leu Ile Tyr Lys Ile Ser Lys Arg Phe Ser Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Pro Glu Asp Val Gly Val Tyr Tyr Cys Met Gln Ser
                85                  90                  95

Thr Arg Phe Pro Arg Thr Phe Gly Gln Gly Thr Lys Leu Glu Ile Lys
            100                 105                 110
```

<210> SEQ ID NO 49
<211> LENGTH: 120
<212> TYPE: PRT
<213> ORGANISM: Homo sapiens

<400> SEQUENCE: 49

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser His
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Thr Ser Arg Leu Glu Trp Leu Leu Tyr Leu Asp Tyr Trp Gly Gln
            100                 105                 110

Gly Thr Leu Val Thr Val Ser Ser
            115                 120
```

```
<210> SEQ ID NO 50
<211> LENGTH: 110
<212> TYPE: PRT
<213> ORGANISM: Homo sapiens

<400> SEQUENCE: 50

Asn Phe Met Leu Thr Gln Pro His Ser Val Ser Glu Ser Pro Gly Lys
1               5                   10                  15

Thr Val Ile Ile Pro Cys Thr Arg Ser Ser Gly Ser Ile Ala Ser Asn
            20                  25                  30

Tyr Val Gln Trp Tyr Gln Lys Arg Pro Gly Ser Ala Pro Ser Ile Val
        35                  40                  45

Ile Tyr Glu Asp Lys Gln Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asn Ser
                85                  90                  95

Arg Gly Val Met Phe Gly Gly Gly Thr Lys Leu Thr Val Leu
            100                 105                 110

<210> SEQ ID NO 51
<211> LENGTH: 123
<212> TYPE: PRT
<213> ORGANISM: Homo sapiens

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Val Arg Ser Leu Arg Ser Asp Asp Thr Ala Val Tyr Tyr Cys
                85                  90                  95

Ala Arg Gly Gly Ser Pro Tyr Gly Gly Tyr Ala Tyr Pro Phe Asp Tyr
            100                 105                 110

Trp Gly Gln Gly Thr Leu Val Thr Val Ser Ser
        115                 120

<210> SEQ ID NO 52
<211> LENGTH: 110
<212> TYPE: PRT
<213> ORGANISM: Homo sapiens

SEQUENCE: 52

Asn Phe Met Leu Thr Gln Pro His Ser Val Leu Glu Ser Ala Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Thr Ser Pro Thr Asn Val
        35                  40                  45

Ile Phe Glu Asp Asn Gln Arg Pro Ser Gly Val Pro Asp Arg Phe Ser
```

```
                50                  55                  60
Gly Ser Ile Asp Ser Ser Asn Ser Ala Ser Leu Thr Ile Ser Gly
 65                  70                  75                  80

Leu Lys Thr Glu Asp Glu Ala Asp Tyr Phe Cys Gln Ser Tyr Asp Ser
                 85                  90                  95

Asn Ile Trp Val Phe Gly Gly Gly Thr Lys Leu Thr Val Leu
            100                 105                 110

<210> SEQ ID NO 53
<211> LENGTH: 122
<212> TYPE: PRT
<213> ORGANISM: Homo sapiens

<400> SEQUENCE: 53

Glu Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ser Tyr Ile Ser Ser Ser Gly Ser Thr Ile Tyr Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Leu Asp Tyr Asp Ile Leu Thr Gly Tyr Gly Tyr Trp
            100                 105                 110

Gly Gln Gly Thr Leu Val Thr Val Ser Ser
            115                 120

<210> SEQ ID NO 54
<211> LENGTH: 111
<212> TYPE: PRT
<213> ORGANISM: Homo sapiens

SEQUENCE: 54

Gln Ser Val Leu Thr Gln Pro Pro Ser Val Ser Ala Ala Pro Gly Gln
  1               5                  10                  15

Lys Val Thr Ile Ser Cys Ser Gly Ser Ser Ser Asn Ile Gly Asn Asn
                 20                  25                  30

Tyr Val Ser Trp Tyr Gln His Leu Pro Gly Thr Ala Pro Lys Leu Leu
             35                  40                  45

Ile Tyr Gly Asn Thr Asn Arg Pro Ser Gly Val Pro Asp Arg Phe Ser
         50                  55                  60

Gly Ser Lys Ser Gly Thr Ser Ala Ser Leu Ala Ile Ala Gly Leu Gln
 65                  70                  75                  80

Ala Glu Asp Glu Ala Asp Tyr Tyr Cys Gln Ser Tyr Asp Ser Ser Leu
                 85                  90                  95

Ser Gly Ser Leu Val Phe Gly Gly Gly Thr Lys Leu Thr Val Leu
            100                 105                 110

<210> SEQ ID NO 55
<211> LENGTH: 123
<212> TYPE: PRT
<213> ORGANISM: Homo sapiens
```

SEQUENCE: 55

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Gly Lys Gly Leu Glu Trp Ile
        35                  40                  45

Gly Glu Ile Asn His Ser Gly Ser Thr Asn Phe Asn Pro Ser Leu Lys
    50                  55                  60

Ser Arg Ile Thr Ile Ser Val Asp Thr Ser Asn Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly His Asp Trp Gly Met Gly Ile Gly Gly Ala Ala Tyr Asp Ile
            100                 105                 110

Trp Gly Gln Gly Thr Met Val Thr Val Ser Ser
            115                 120

<210> SEQ ID NO 56
<211> LENGTH: 108
<212> TYPE: PRT
<213> ORGANISM: Homo sapiens

SEQUENCE: 56

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Ala Gly Gln Ala Pro Arg Leu Leu
        35                  40                  45

Ile Tyr Asp Thr Ser Thr Arg Ala Thr Gly Ile Ala Asp Arg Phe Ser
    50                  55                  60

Gly Ser Gly Ser Gly Thr Asp Phe Thr Leu Thr Ile Ser Arg Leu Glu
65                  70                  75                  80

Ala Glu Asp Ser Ala Val Tyr Tyr Cys Gln Gln Tyr Asp Phe Ser Pro
                85                  90                  95

Leu Thr Phe Gly Gly Gly Thr Lys Val Glu Ile Lys
            100                 105

<210> SEQ ID NO 57
<211> LENGTH: 112
<212> TYPE: PRT
<213> ORGANISM: Homo sapiens

<400> SEQUENCE: 57

Gln Val Gln Leu Val Glu Ser Gly Gly Gly Leu Val Gln Pro Gly Gly
1               5                   10                  15

Ser Leu Arg Leu Ser Cys Ala Ser Gly Phe Thr Phe Phe Ser Thr
            20                  25                  30

Tyr Ala Met Thr Trp Val Arg Gln Ala Pro Gly Lys Gly Leu Glu Trp
        35                  40                  45

Val Ser Val Ile Arg Ser Asn Gly Gly Thr Asp Tyr Ala Asp Phe Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ala Glu Asp Thr Ala Val Tyr Tyr Cys
                85                  90                  95

Met Thr Asp Tyr Tyr Trp Gly Gln Gly Thr Leu Val Thr Val Ser Ser
                100                 105                 110

<210> SEQ ID NO 58
<211> LENGTH: 110
<212> TYPE: PRT
<213> ORGANISM: Homo sapiens

<400> SEQUENCE: 58

Asn Phe Met Leu Thr Gln Pro His Ser Val Ser Glu Ser Pro Gly Lys
1               5                   10                  15

Thr Val Thr Ile Ser Cys Thr Gly Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Thr Trp Val Phe Gly Gly Gly Thr Lys Leu Thr Val Leu
                100                 105                 110

<210> SEQ ID NO 59
<211> LENGTH: 123
<212> TYPE: PRT
<213> ORGANISM: Homo sapiens

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Thr Ile Ser Phe Ser Thr Phe Ser Gly Tyr Phe Asp Tyr
                100                 105                 110

Trp Gly Gln Gly Thr Leu Val Thr Val Ser Ser
            115                 120

<210> SEQ ID NO 60
<211> LENGTH: 110
<212> TYPE: PRT
<213> ORGANISM: Homo sapiens

<400> SEQUENCE: 60

Gln Ser Ala Leu Thr Gln Pro Ala Ser Val Ser Gly Ser Pro Gly Gln
1               5                   10                  15

```
Ser Ile Thr Ile Ser Cys Thr Gly Thr Ser Ser Asp Val Gly Gly Tyr
             20                  25                  30

Asn Tyr Val Ser Trp Phe Gln Gln His Pro Gly Lys Ala Pro Lys Leu
         35                  40                  45

Met Ile Tyr Lys Val Asn Asn Arg Pro Ser Gly Leu Ser Asn Arg Phe
 50                  55                  60

Ser Gly Ser Gln Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Leu Gly Phe Gly Gly Gly Thr Lys Leu Thr Val Leu
            100                 105                 110

<210> SEQ ID NO 61
<211> LENGTH: 122
<212> TYPE: PRT
<213> ORGANISM: Homo sapiens

<400> SEQUENCE: 61

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
             20                  25                  30

Asp Ile Asn Trp Val Arg Gln Ala Thr Gly Gln Gly Leu Glu Trp Met
         35                  40                  45

Gly Trp Met Asn Pro Asn Ser Gly Asn Thr Gly Tyr Ala Gln Lys Phe
 50                  55                  60

Gln Gly Arg Val Thr Met Thr Arg Asn Thr Ser Ile Ser Thr Ala Tyr
65                   70                  75                  80

Met Glu Leu Ser Ser Leu Arg Ser Glu Asp Thr Ala Val Tyr Tyr Cys
                 85                  90                  95

Ala Lys Glu Ile Ala Val Ala Gly Thr Arg Tyr Gly Met Asp Val Trp
            100                 105                 110

Gly Gln Gly Thr Thr Val Thr Val Ser Ser
            115                 120

<210> SEQ ID NO 62
<211> LENGTH: 107
<212> TYPE: PRT
<213> ORGANISM: Homo sapiens

<400> SEQUENCE: 62

Glu Ile Val Leu Thr Gln Ser Pro Gly Thr Leu Ser Leu Ser Pro Gly
1               5                  10                  15

Glu Arg Ala Thr Leu Ser Cys Arg Ala Ser Gln Ser Ile Ser Thr Phe
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Gly Arg Phe Ser Gly
 50                  55                  60

Ser Gly Ser Gly Thr Asp Phe Thr Leu Thr Ile Ser Asn Leu Glu Pro
65                   70                  75                  80

Glu Asp Phe Ala Val Tyr Tyr Cys Gln His Arg Ile Asn Trp Pro Leu
                 85                  90                  95

Thr Phe Gly Gly Gly Thr Lys Val Glu Ile Lys
            100                 105
```

<210> SEQ ID NO 63
<211> LENGTH: 106
<212> TYPE: PRT
<213> ORGANISM: Homo sapiens

<400> SEQUENCE: 63

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 64
<211> LENGTH: 106
<212> TYPE: PRT
<213> ORGANISM: Homo sapiens

<400> SEQUENCE: 64

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 65
<211> LENGTH: 106
<212> TYPE: PRT
<213> ORGANISM: Homo sapiens

<400> SEQUENCE: 65

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys

```
                65                  70                  75                  80
Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 66
<211> LENGTH: 106
<212> TYPE: PRT
<213> ORGANISM: Homo sapiens

<400> SEQUENCE: 66

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
                20                  25                  30

Phe Tyr Pro Gly Ala Val Thr Val Ala Trp Lys Ala Asp Gly Ser Pro
            35                  40                  45

Val Lys Val Gly Val Glu Thr Thr Lys Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105

<210> SEQ ID NO 67
<211> LENGTH: 107
<212> TYPE: PRT
<213> ORGANISM: Homo sapiens

<400> SEQUENCE: 67

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 68
<211> LENGTH: 330
<212> TYPE: PRT
<213> ORGANISM: Homo sapiens

<400> SEQUENCE: 68

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 69
<211> LENGTH: 22
<212> TYPE: PRT
<213> ORGANISM: Homo sapiens

<400> SEQUENCE: 69

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 70
<211> LENGTH: 40
<212> TYPE: DNA
<213> ORGANISM: Homo sapiens

<400> SEQUENCE: 70
```

-continued

```
gtggttgaga ggtgccagat gtcaggtcca gctggtgcag                40

<210> SEQ ID NO 71
<211> LENGTH: 30
<212> TYPE: DNA
<213> ORGANISM: Homo sapiens

<400> SEQUENCE: 71
attacgtctc acagttcgtt tgatctccac                           30

<210> SEQ ID NO 72
<211> LENGTH: 48
<212> TYPE: DNA
<213> ORGANISM: Homo sapiens

<400> SEQUENCE: 72
ccgctcagct cctggggctc ctgctattgt ggttgagagg tgccagat       48

<210> SEQ ID NO 73
<211> LENGTH: 9
<212> TYPE: PRT
<213> ORGANISM: Homo sapiens

<400> SEQUENCE: 73

Ala Gln Leu Leu Gly Leu Leu Leu Leu
  1               5

<210> SEQ ID NO 74
<211> LENGTH: 54
<212> TYPE: DNA
<213> ORGANISM: Homo sapiens

<400> SEQUENCE: 74
cagcagaagc ttctagacca ccatggacat gagggtcccc gctcagctcc tggg    54

<210> SEQ ID NO 75
<211> LENGTH: 45
<212> TYPE: DNA
<213> ORGANISM: Homo sapiens

<400> SEQUENCE: 75
gtggttgaga ggtgccagat gtgacattgt gatgactcag tctcc          45

<210> SEQ ID NO 76
<211> LENGTH: 31
<212> TYPE: DNA
<213> ORGANISM: Homo sapiens

<400> SEQUENCE: 76
cttgtcgact tattaacact ctcccctgtt g                         31
```

ANGIOPOIETIN-2 SPECIFIC BINDING AGENTS

This application claims benefit to U.S. Provisional Application Ser. No. 60/328,604, filed Oct. 11, 2001, which is incorporated herein by reference.

FIELD OF THE INVENTION

The present invention relates to specific binding agents that recognize and bind to angiopoietin-2 (Ang-2). More specifically, the invention relates to the production, diagnostic use, and therapeutic use of monoclonal and polyclonal antibodies, and fragments thereof, which specifically bind Ang-2.

BACKGROUND OF THE INVENTION

Angiogenesis, the formation of new blood vessels from existing ones, is essential to many physiological and pathological processes. Normally, angiogenesis is tightly regulated by pro- and anti-angiogenic factors, but in the case of diseases such as cancer, ocular neovascular diseases, arthritis, and psoriasis, the process can go awry. Folkman, J., *Nat. Med.*, 1:27-31 (1995).

There are a number of diseases known to be associated with deregulated or undesired angiogenesis. Such diseases include, but are not limited to, ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid (or hematopoietic) tumors (such as leukemias and lymphomas). Other diseases associated with undesired angiogenesis will be apparent to those skilled in the art.

Although many signal transduction systems have been implicated in the regulation of angiogenesis, one of the best-characterized and most endothelial cell-selective systems involves the Tie-2 receptor tyrosine kinase (referred to as "Tie-2" or "Tie-2R" (also referred to as "ORK"); murine Tie-2 is also referred to as "tek") and its ligands, the angiopoietins (Gale, N. W. and Yancopoulos, G. D., *Genes Dev.* 13:1055-1066 [1999]). There are 4 known angiopoietins; angiopoietin-1 ("Ang-1") through angiopoietin-4 ("Ang-4"). These angiopoietins are also referred to as "Tie-2 ligands". (Davis, S., et al., *Cell*, 87:1161-1169 [1996]; Grosios, K., et al., *Cytogenet Cell Genet*, 84:118-120 [1999]; Holash, J., et al., *Investigative Ophthalmology & Visual Science*, 42:1617-1625 [1999]; Koblizek, T. I., et al., *Current Biology*, 8:529-532 [1998]; Lin, P., et al., *Proc Natl Acad Sci USA*, 95:8829-8834 [1998]; Maisonpierre, P. C., et al., *Science*, 277:55-60 [1997]; Papapetropoulos, A., et al., *Lab Invest*, 79:213-223 [1999]; Sato, T. N., et al., *Nature*, 375:70-74 [1998]; Shyu, K. G., et al., *Circulation*, 98:2081-2087 [1998]; Suri, C., et al., *Cell*, 87:1171-1180 [1996]; Suri, C., et al., *Science*, 282:468-471 [1998]; Valenzuela, D. M., et al., *Proceedings of the National Academy of Sciences of the USA*, 96:1904-1909 [1999]; Witzenbichler, B., et al., *J Biol Chem*, 273:18514-18521 [1998]). Whereas Ang-1 binding to Tie-2 stimulates receptor phosphorylation in cultured endothelial cells, Ang-2 has been observed to both agonize and antagonize Tie-2 receptor phosphorylation (Davis, S., et al., [1996], supra; Maisonpierre, P. C., et al., [1997], supra; Kim, I., J. H. Kim, et al., *Oncogene* 19(39): 4549-4552 (2000); Teichert-Kuliszewska, K., P. C. Maisonpierre, et al., *Cardiovascular Research* 49(3): 659-70 (2001)).

The phenotypes of mouse Tie-2 and Ang-1 knockouts are similar and suggest that Ang-1-stimulated Tie-2 phosphorylation mediates remodeling and stabilization of developing vessels in utero through maintenance of endothelial cell-support cell adhesion (Dumont, D. J., et al., *Genes & Development*, 8:1897-1909 [1994]; Sato, T. N., et al., *Nature*, 376: 70-74 [1995]; Suri, C., et al., [1996], supra). The role of Ang-1 in vessel stabilization is thought to be conserved in the adult, where it is expressed widely and constitutively (Hanahan, D., *Science*, 277:48-50 [1997]; Zagzag, D., et al., *Experimental Neurology*, 159:391-400 [1999]). In contrast, Ang-2 expression is primarily limited to sites of vascular remodeling, where it is thought to block Ang-1 function, thereby inducing a state of vascular plasticity conducive to angiogenesis (Hanahan, D., [1997], supra; Holash, J., et al., *Science*, 284:1994-1998 [1999]; Maisonpierre, P. C., et al., [1997], supra).

Numerous published studies have purportedly demonstrated vessel-selective Ang-2 expression in disease states associated with angiogenesis. These pathological conditions include, for example, psoriasis, macular degeneration, and cancer (Bunone, G., et al., *American Journal of Pathology*, 155:1967-1976 [1999]; Etoh, T., et al., *Cancer Research*, 61:2145-2153 [2001]; Hangai, M., et al., *Investigative Ophthalmology & Visual Science*, 42:1617-1625 [2001]; Holash, J., et al., [1999] supra; Kuroda, K., et al., *Journal of Investigative Dermatology*, 116:713-720 [2001]; Otani, A., et al., *Investigative Ophthalmology & Visual Science*, 40:1912-1920 [1999]; Stratmann, A., et al., *American Journal of Pathology*, 153:1459-1466 [1998]; Tanaka, S., et al., *J Clin Invest*, 103:34-345 [1999]; Yoshida, Y., et al., *International Journal of Oncology*, 15:1221-1225 [1999]; Yuan, K., et al., *Journal of Periodontal Research*, 35:165-171 [2000]; Zagzag, D., et al., [1999] supra). Most of these studies have focused on cancer, in which many tumor types appear to display vascular Ang-2 expression. In contrast with its expression in pathological angiogenesis, Ang-2 expression in normal tissues is extremely limited (Maisonpierre, P. C., et al., [1997], supra; Mezquita, J., et al., *Biochemical and Biophysical Research Communications*, 260:492-498 [1999]). In the normal adult, the three main sites of angiogenesis are the ovary, placenta, and uterus; these are the primary tissues in normal (i.e., non-cancerous) tissues in which Ang-2 mRNA has been detected.

Certain functional studies suggest that Ang-2 may be involved in tumor angiogenesis. Ahmad et al. (*Cancer Res.*, 61:1255-1259 [2001]) describe Ang-2 over-expression and show that it is purportedly associated with an increase in tumor growth in a mouse xenograft model. See also Etoh et al., supra, and Tanaka et al., supra, wherein data is presented purportedly associating Ang-2 over expression with tumor hypervascularity. However, in contrast, Yu et al. (*Am. J. Path.*, 158:563-570 [2001]) report data to show that overexpression of Ang-2 in Lewis lung carcinoma and TA3 mammary carcinoma cells purportedly prolonged the survival of mice injected with the corresponding transfectants.

In the past few years, various publications have suggested Ang-1, Ang-2 and/or Tie-2 as a possible target for anti-cancer therapy. For example, U.S. Pat. Nos. 6,166,185, 5,650,490, and 5,814,464 each disclose the concept of anti-Tie-2 ligand antibodies and receptor bodies. Lin et al. (*Proc. Natl. Acad. Sci USA*, 95:8829-8834 [1998]) injected an adenovirus expressing soluble Tie-2 into mice; the soluble Tie-2 purportedly decreased the number and size of the tumors developed by the mice. In a related study, Lin et al (*J. Clin. Invest.,* 100:2072-2078 [1997]) injected a soluble form of Tie-2 into rats; this compound purportedly reduced tumor size in the rats. Siemeister et al. (*Cancer Res.,* 59:3185-3189 [1999]) generated human melanoma cell lines expressing the extracellular domain of Tie-2, injected these cell lines into nude mice, and concluded that soluble Tie-2 purportedly resulted in a "significant inhibition" of tumor growth and tumor angiogenesis. In view of this information, and given that both Ang-1 and Ang-2 bind to Tie-2, it is not clear from these studies whether Ang-1, Ang-2, or Tie-2 would be an attractive target for anti-cancer therapy.

The fusion of certain peptides to a stable plasma protein such as an Ig constant region to improve the half-life of these molecules has been described in, for example, PCT publication WO 00/24782, published May 4, 2000.

The fusion of a protein or fragment thereof to a stable plasma protein such as an Ig constant region to improve the half-life of these molecules has been variously described (see, for example, U.S. Pat. No. 5,480,981; Zheng et al., *J. Immunol.,* 154:5590-5600, (1995); Fisher et al., *N. Engl. J. Med.,* 334:1697-1702, (1996); Van Zee, K. et al., *J. Immunol.,* 156: 2221-2230, (1996); U.S. Pat. No. 5,808,029, issued Sep. 15, 1998; Capon et al., *Nature,* 337:525-531, (1989); Harvill et al., *Immunotech.,* 1:95-105, (1995); WO 97/23614, published Jul. 3, 1997; PCT/US 97/23183, filed Dec. 11, 1997; Linsley, *J. Exp. Med.,* 174:561-569, (1991); WO 95/21258, published Aug. 10, 1995).

An effective anti-Ang-2 therapy might benefit a vast population of cancer patients because most solid tumors require neovascularization to grow beyond 1-2 millimeters in diameter. Such therapy might have wider application in other angiogenesis-associated diseases as well, such as retinopathies, arthritis, and psoriasis.

There is an undeveloped need to identify new agents that specifically recognize and bind Ang-2. Such agents would be useful for diagnostic screening and therapeutic intervention in disease states that are associated with Ang-2 activity.

Accordingly, it is an object of the present invention to provide specific binding agents of Ang-2 that modulate Ang-2 activity.

SUMMARY OF THE INVENTION

The present invention provides an antibody comprising a heavy chain and a light chain, wherein said heavy chain comprises a heavy chain variable region selected from the group consisting of 526 HC (SEQ ID NO. 1); 528 HC (SEQ ID NO. 3); 531 HC (SEQ ID NO. 5); 533 HC (SEQ ID NO. 7); 535 HC (SEQ ID NO. 9); 536 HC (SEQ ID NO. 11); 537 HC (SEQ ID NO. 13); 540 HC (SEQ ID NO. 15); 543 HC (SEQ ID NO. 17); 544 HC (SEQ ID NO. 19); 545 HC (SEQ ID NO. 21); 546 HC (SEQ ID NO. 23); 551 HC (SEQ ID NO. 25); 553 HC (SEQ ID NO. 27); 555 HC (SEQ ID NO. 29); 558 HC (SEQ ID NO. 31); 559 HC (SEQ ID NO. 33); 565 HC (SEQ ID NO. 35); F1-C6 HC (SEQ ID NO. 37); FB1-A7 HC (SEQ ID NO. 39); FD-B2 HC (SEQ ID NO. 41); FE-B7 HC (SEQ ID NO. 43); FJ-G11 HC (SEQ ID NO. 45); FK-E3 HC (SEQ ID NO. 47); G1D4 HC (SEQ ID NO. 49); GC1E8 HC (SEQ ID NO. 51); H1C12 HC (SEQ ID NO. 53); IA1-1E7 HC (SEQ ID NO. 55); IF-1C10 HC (SEQ ID NO. 57); IK-2E2 HC (SEQ ID NO. 59); IP-2C11 HC (SEQ ID NO. 61); and antigen binding fragments thereof; and said light chain comprises a light chain variable region selected from the group consisting of: 526 kappa (SEQ ID NO. 2); 536 kappa (SEQ ID NO. 12); 543 kappa (SEQ ID NO. 18); 544 kappa (SEQ ID NO. 20); 551 kappa (SEQ ID NO. 26); 553 kappa (SEQ ID NO. 28); 555 kappa (SEQ ID NO. 30); 558 kappa (SEQ ID NO. 32); 565 kappa (SEQ ID NO. 36); FE-B7 kappa (SEQ ID NO. 44); FJ-G11 kappa (SEQ ID NO. 46); FK-E3 kappa (SEQ ID NO. 48); IA1-1E7 kappa (SEQ ID NO. 56); IP-2C11 kappa (SEQ ID NO. 62); 528 lambda (SEQ ID NO. 4); 531 lambda (SEQ ID NO. 6); 533 lambda (SEQ ID NO. 8); 535 lambda (SEQ ID NO. 10); 537 lambda (SEQ ID NO. 14); 540 lambda (SEQ ID NO. 16); 545 lambda (SEQ ID NO. 22); 546 lambda (SEQ ID NO. 24); 559 lambda (SEQ ID NO. 34); F1-C6 lambda (SEQ ID NO. 38); FB1-A7 lambda (SEQ ID NO. 40); FD-B2 lambda (SEQ ID NO. 42); G1D4 lambda (SEQ ID NO. 50); GC1E8 lambda (SEQ ID NO. 52); H1C12 lambda (SEQ ID NO. 54); IF-1C10 lambda (SEQ ID NO. 58); IK-2E2 lambda (SEQ ID NO. 60); and antigen binding fragments thereof.

The invention also provides a specific binding agent comprising at least one peptide selected from the group consisting of:

SEQ ID NO. 1; SEQ ID NO. 3; SEQ ID NO. 5; SEQ ID NO. 7; SEQ ID NO. 9; SEQ ID NO. 11; SEQ ID NO. 13; SEQ ID NO. 15; SEQ ID NO. 17; SEQ ID NO. 19; SEQ ID NO. 21; SEQ ID NO. 23; SEQ ID NO. 25; SEQ ID NO. 27; SEQ ID NO. 29; SEQ ID NO. 31; SEQ ID NO. 33; SEQ ID NO. 35; SEQ ID NO. 37; SEQ ID NO. 39; SEQ ID NO. 41; SEQ ID NO. 43; SEQ ID NO. 45; SEQ ID NO. 47; SEQ ID NO. 49; SEQ ID NO. 51; SEQ ID NO. 53; SEQ ID NO. 55; SEQ ID NO. 57; SEQ ID NO. 59; SEQ ID NO. 61; SEQ ID NO. 2; SEQ ID NO. 12; SEQ ID NO. 18; SEQ ID NO. 20; SEQ ID NO. 26; SEQ ID NO. 28; SEQ ID NO. 30; SEQ ID NO. 32; SEQ ID NO. 36; SEQ ID NO. 44; SEQ ID NO. 46; SEQ ID NO. 48; SEQ ID NO. 56; SEQ ID NO. 62; SEQ ID NO. 4; SEQ ID NO. 6; SEQ ID NO. 8; SEQ ID NO. 10; SEQ ID NO. 14; SEQ ID NO. 16; SEQ ID NO. 22; SEQ ID NO. 24; SEQ ID NO. 34; SEQ ID NO. 38; SEQ ID NO. 40; SEQ ID NO. 42; SEQ ID NO. 50; SEQ ID NO. 52; SEQ ID NO. 54; SEQ ID NO. 58; and SEQ ID NO. 60, and fragments thereof.

It will be appreciated that the specific binding agent can be, for example, an antibody, such as a polyclonal, monoclonal, chimeric, humanized, or a fully human antibody. The antibody may also be a single chain antibody. The invention further relates to a hybridoma that produces a monoclonal antibody according to the invention.

It will also be appreciated that the invention relates to conjugates as described herein. The conjugate can be, for example, a specific binding agent (such as an antibody) of the invention.

The invention further relates to nucleic acid molecules encoding the specific binding agents (such as an antibody) of the invention, as well as a vector comprising such nucleic acid molecule, as well as a host cell containing the vector.

Additionally, the invention provides a method of making a specific binding agent comprising, (a) transforming a host cell with at least one nucleic acid molecule encoding the specific binding agent of claim 1; (b) expressing the nucleic acid molecule in said host cell; and (c) isolating said specific binding agent. The invention further provides a method of making an antibody comprising: (a) transforming a host cell with at least one nucleic acid molecule encoding the antibody according to the invention; (b) expressing the nucleic acid molecule in said host cell; and (c) isolating said specific binding agent.

Further, the invention relates to a method of inhibiting undesired angiogenesis in a mammal by administering a therapeutically effective amount of a specific binding agent according to the invention. The invention also provides a method of treating cancer in a mammal by administering a therapeutically effective amount of a specific binding agent according to the invention.

The invention also relates to a method of inhibiting undesired angiogenesis in a mammal comprising by administering a therapeutically effective amount of an antibody according to the invention. The invention additionally provides a method of treating cancer in a mammal comprising administering a therapeutically effective amount of antibody according to the invention.

It will be appreciated that the invention further relates to pharmaceutical compositions comprising the specific binding agent according to the invention and a pharmaceutically acceptable formulation agent. The pharmaceutical composition may comprise an antibody according to the invention and a pharmaceutically acceptable formulation agent.

The invention provides a method of modulating or inhibiting angiopoietin-2 activity by administering one or more specific binding agents of the invention. The invention also provides a method of modulating or inhibiting angiopoietin-2 activity by administering an antibody of the invention.

The invention further relates to a method of modulating at least one of vascular permeability or plasma leakage in a mammal comprising administering a therapeutically effective amount of the specific binding agent according to the invention. The invention also relates to a method of treating at least one of ocular neovascular disease, obesity, hemangioblastoma, hemangioma, arteriosclerosis, inflammatory disease, inflammatory disorders, atherosclerosis, endometriosis, neoplastic disease, bone-related disease, or psoriasis in a mammal comprising administering a therapeutically effective amount of a specific binding agent according to the invention.

The invention further provides a method of modulating at least one of vascular permeability or plasma leakage in a mammal comprising administering a therapeutically effective amount of an antibody according to the invention. The invention also relates to a method of treating at least one of ocular neovascular disease, obesity, hemangioblastoma, hemangioma, arteriosclerosis, inflammatory disease, inflammatory disorders, atherosclerosis, endometriosis, neoplastic disease, bone-related disease, or psoriasis in a mammal comprising administering a therapeutically effective amount of an antibody according to the invention.

Furthermore, the invention relates to a method of treating cancer in a mammal comprising administering a therapeutically effective amount of a specific binding agent according to the invention and a chemotherapeutic agent. It will be appreciated by those in the art that the specific binding agent and chemotherapeutic agent need not be administered simultaneously.

The invention also relates to a method of treating cancer in a mammal comprising administering a therapeutically effective amount of an antibody according to the invention and a chemotherapeutic agent. The specific binding agent and chemotherapeutic agent need not be administered simultaneously.

The invention also provides a specific binding agent comprising complementarity determining region 1 (CDR 1) of any of: 526 HC (SEQ ID NO. 1); 528 HC (SEQ ID NO. 3); 531 HC (SEQ ID NO. 5); 533 HC (SEQ ID NO. 7); 535 HC (SEQ ID NO. 9); 536 HC (SEQ ID NO. 11); 537 HC (SEQ ID NO. 13); 540 HC (SEQ ID NO. 15); 543 HC (SEQ ID NO. 17); 544 HC (SEQ ID NO. 19); 545 HC (SEQ ID NO. 21); 546 HC (SEQ ID NO. 23); 551 HC (SEQ ID NO. 25); 553 HC (SEQ ID NO. 27); 555 HC (SEQ ID NO. 29); 558 HC (SEQ ID NO. 31); 559 HC (SEQ ID NO. 33); 565 HC (SEQ ID NO. 35); F1-C6 HC (SEQ ID NO. 37); FB1-A7 HC (SEQ ID NO. 39); FD-B2 HC (SEQ ID NO. 41); FE-B7 HC (SEQ ID NO. 43); FJ-G11 HC (SEQ ID NO. 45); FK-E3 HC (SEQ ID NO. 47); G1D4 HC (SEQ ID NO. 49); GC1E8 HC (SEQ ID NO. 51); H1C12 HC (SEQ ID NO. 53); IA1-1E7 HC (SEQ ID NO. 55); IF-1C10 HC (SEQ ID NO. 57); IK-2E2 HC (SEQ ID NO. 59); IP-2C11 HC (SEQ ID NO. 61); 526 kappa (SEQ ID NO. 2); 536 kappa (SEQ ID NO. 12); 543 kappa (SEQ ID NO. 18); 544 kappa (SEQ ID NO. 20); 551 kappa (SEQ ID NO. 26); 553 kappa (SEQ ID NO. 28); 555 kappa (SEQ ID NO. 30); 558 kappa (SEQ ID NO. 32); 565 kappa (SEQ ID NO. 36); FE-B7 kappa (SEQ ID NO. 44); FJ-G11 kappa (SEQ ID NO. 46); FK-E3 kappa (SEQ ID NO. 48); IA1-1E7 kappa (SEQ ID NO. 56); IP-2C11 kappa (SEQ ID NO. 62); 528 lambda (SEQ ID NO. 4); 531 lambda (SEQ ID NO. 6); 533 lambda (SEQ ID NO. 8); 535 lambda (SEQ ID NO. 10); 537 lambda (SEQ ID NO. 14); 540 lambda (SEQ ID NO. 16); 545 lambda (SEQ ID NO. 22); 546 lambda (SEQ ID NO. 24); 559 lambda (SEQ ID NO. 34); F1-C6 lambda (SEQ ID NO. 38); FB1-A7 lambda (SEQ ID NO. 40); FD-B2 lambda (SEQ ID NO. 42); G1D4 lambda (SEQ ID NO. 50); GC1E8 lambda (SEQ ID NO. 52); H1C12 lambda (SEQ ID NO. 54); IF-1C10 lambda (SEQ ID NO. 58); and IK-2E2 lambda (SEQ ID NO. 60).

The invention further relates to a specific binding agent comprising complementarity determining region 2 (CDR 2) of any of: 526 HC (SEQ ID NO. 1); 528 HC (SEQ ID NO. 3); 531 HC (SEQ ID NO. 5); 533 HC (SEQ ID NO. 7); 535 HC (SEQ ID NO. 9); 536 HC (SEQ ID NO. 11); 537 HC (SEQ ID NO. 13); 540 HC (SEQ ID NO. 15); 543 HC (SEQ ID NO. 17); 544 HC (SEQ ID NO. 19); 545 HC (SEQ ID NO. 21); 546 HC (SEQ ID NO. 23); 551 HC (SEQ ID NO. 25); 553 HC (SEQ ID NO. 27); 555 HC (SEQ ID NO. 29); 558 HC (SEQ ID NO. 31); 559 HC (SEQ ID NO. 33); 565 HC (SEQ ID NO. 35); F1-C6 HC (SEQ ID NO. 37); FB1-A7 HC (SEQ ID NO. 39); FD-B2 HC (SEQ ID NO. 41); FE-B7 HC (SEQ ID NO. 43); FJ-G11 HC (SEQ ID NO. 45); FK-E3 HC (SEQ ID NO. 47); G1D4 HC (SEQ ID NO. 49); GC1E8 HC (SEQ ID NO. 51); H1C12 HC (SEQ ID NO. 53); IA1-1E7 HC (SEQ ID NO. 55); IF-1C10 HC (SEQ ID NO. 57); IK-2E2 HC (SEQ ID NO. 59); IP-2C11 HC (SEQ ID NO. 61); 526 kappa (SEQ ID NO. 2); 536 kappa (SEQ ID NO. 12); 543 kappa (SEQ ID NO. 18); 544 kappa (SEQ ID NO. 20); 551 kappa (SEQ ID NO. 26); 553 kappa (SEQ ID NO. 28); 555 kappa (SEQ ID NO. 30); 558 kappa (SEQ ID NO. 32); 565 kappa (SEQ ID NO. 36); FE-B7 kappa (SEQ ID NO. 44); FJ-G11 kappa (SEQ ID NO. 46); FK-E3 kappa (SEQ ID NO. 48); IA1-1E7 kappa (SEQ ID NO. 56); IP-2C11 kappa (SEQ ID NO. 62); 528 lambda (SEQ ID NO. 4); 531 lambda (SEQ ID NO. 6); 533 lambda (SEQ ID NO. 8); 535 lambda (SEQ ID NO. 10); 537 lambda (SEQ ID NO. 14); 540 lambda (SEQ ID NO. 16); 545 lambda (SEQ ID NO. 22); 546 lambda (SEQ ID NO. 24); 559 lambda (SEQ ID NO. 34); F1-C6 lambda (SEQ ID NO. 38); FB1-A7 lambda (SEQ ID NO. 40); FD-B2 lambda (SEQ ID NO. 42); G1D4 lambda (SEQ ID NO. 50); GC1E8 lambda (SEQ ID NO. 52); H1C12 lambda (SEQ ID NO. 54); IF-1C10 lambda (SEQ ID NO. 58); and IK-2E2 lambda (SEQ ID NO. 60).

The invention also relates to a specific binding agent comprising complementarity determining region 3 (CDR 3) of any of: 526 HC (SEQ ID NO. 1); 528 HC (SEQ ID NO. 3); 531 HC (SEQ ID NO. 5); 533 HC (SEQ ID NO. 7); 535 HC (SEQ ID NO. 9); 536 HC (SEQ ID NO. 11); 537 HC (SEQ ID NO. 13); 540 HC (SEQ ID NO. 15); 543 HC (SEQ ID NO. 17); 544 HC (SEQ ID NO. 19); 545 HC (SEQ ID NO. 21); 546 HC (SEQ ID NO. 23); 551 HC (SEQ ID NO. 25); 553 HC (SEQ ID NO. 27); 555 HC (SEQ ID NO. 29); 558 HC (SEQ ID NO. 31); 559 HC (SEQ ID NO. 33); 565 HC (SEQ ID NO. 35); F1-C6 HC (SEQ ID NO. 37); FB1-A7 HC (SEQ ID NO. 39); FD-B2 HC (SEQ ID NO. 41); FE-B7 HC (SEQ ID NO. 43); FJ-G11 HC (SEQ ID NO. 45); FK-E3 HC (SEQ ID NO. 47); G1D4 HC (SEQ ID NO. 49); GC1E8 HC (SEQ ID NO.

51); H1C12 HC (SEQ ID NO. 53); IA1-1E7 HC (SEQ ID NO. 55); IF-1C10 HC (SEQ ID NO. 57); IK-2E2 HC (SEQ ID NO. 59); IP-2C11 HC (SEQ ID NO. 61); 526 kappa (SEQ ID NO. 2); 536 kappa (SEQ ID NO. 12); 543 kappa (SEQ ID NO. 18); 544 kappa (SEQ ID NO. 20); 551 kappa (SEQ ID NO. 26); 553 kappa (SEQ ID NO. 28); 555 kappa (SEQ ID NO. 30); 558 kappa (SEQ ID NO. 32); 565 kappa (SEQ ID NO. 36); FE-B7 kappa (SEQ ID NO. 44); FJ-G11 kappa (SEQ ID NO. 46); FK-E3 kappa (SEQ ID NO. 48); IA1-1E7 kappa (SEQ ID NO. 56); IP-2C11 kappa (SEQ ID NO. 62); 528 lambda (SEQ ID NO. 4); 531 lambda (SEQ ID NO. 6); 533 lambda (SEQ ID NO. 8); 535 lambda (SEQ ID NO. 10); 537 lambda (SEQ ID NO. 14); 540 lambda (SEQ ID NO. 16); 545 lambda (SEQ ID NO. 22); 546 lambda (SEQ ID NO. 24); 559 lambda (SEQ ID NO. 34); F1-C6 lambda (SEQ ID NO. 38); FB1-A7 lambda (SEQ ID NO. 40); FD-B2 lambda (SEQ ID NO. 42); G1D4 lambda (SEQ ID NO. 50); GC1E8 lambda (SEQ ID NO. 52); H1C12 lambda (SEQ ID NO. 54); IF-1C10 lambda (SEQ ID NO. 58); and IK-2E2 lambda (SEQ ID NO. 60).

The invention further provides a nucleic acid molecule encoding a specific binding agent according to the invention.

Moreover, the invention relates to a method of detecting the level of angiopoietin-2 in a biological sample by (a) contacting a specific binding agent of the invention with the sample; and (b) determining the extent of binding of the specific binding agent to the sample. The invention also relates to a method of detecting the level of angiopoietin-2 in a biological sample by (a) contacting an antibody of the invention with the sample; and (b) determining the extent of binding of the antibody to the sample.

The invention also relates to a method of inhibiting undesired angiogenesis in a mammal comprising administering a therapeutically effective amount of a polypeptide or composition as described herein. The invention also relates to a method of modulating angiogenesis in a mammal comprising administering a therapeutically effective amount of a polypeptide or composition as described herein. The invention further relates to a method of inhibiting tumor growth characterized by undesired angiogenesis in a mammal comprising administering a therapeutically effective amount of a polypeptide or composition as described herein. Additionally, the invention relates to a method of treating cancer in a mammal comprising administering a therapeutically effective amount of a polypeptide or composition as described herein, and a chemotherapeutic agent. In a preferred embodiment, the chemotherapeutic agent is at least one of 5-FU, CPT-11, and Taxotere. It will be appreciated, however, that other suitable chemotherapeutic agents and other cancer therapies can be used.

It will be appreciated that the specific binding agents of the invention can be used to treat a number of diseases associated with deregulated or undesired angiogenesis. Such diseases include, but are not limited to, ocular neovascularisation, such as retinopathies (including diabetic retinopathy and age-related macular degeneration) psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias). Additional diseases which can be treated by administration of the specific binding agents will be apparent to those skilled in the art. Such additional diseases include, but are not limited to, obesity, vascular permeability, plasma leakage, and bone-related disorders, including osteoporosis. Thus, the invention further relates to methods of treating these diseases associated with deregulated or undesired angiogenesis.

Other embodiments of this invention will be readily apparent from the disclosure provided herewith.

BRIEF DESCRIPTION OF THE FIGURES

FIGS. 2A, 2B, and 2C depict epitope mapping data (O.D. 370) for full-length human Ang-2 (hAng-2), to the N-terminus of hAng-2, and to the C-terminus of hAng-2, respectively, for peptibodies TN8-Con4-C, L1-7-N, and 12-9-3-C according to the invention, as well as for control peptibody, Tie2-Fc, C2B8, or 5B 12. Details are described in the Examples.

DETAILED DESCRIPTION OF INVENTION

Figure 1:
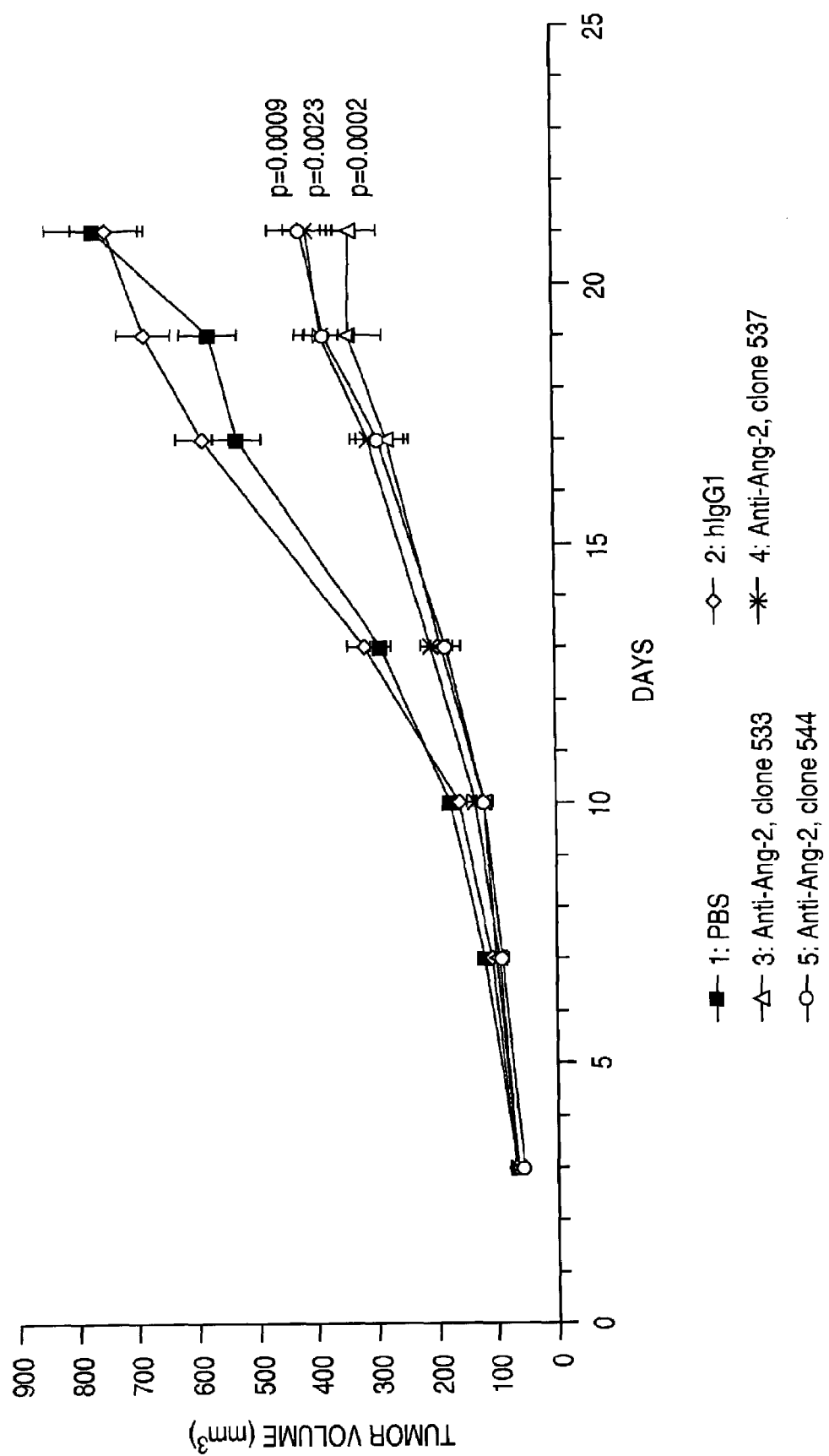
FIG. 1 depicts a graph of tumor size (y-axis) versus time x-axis) in tumor bearing mice treated with either an anti-Ang-2 antibody (clone 533, 537 or 544) of the invention, with a control antibody, or with phosphate buffered saline (PBS). Details are described in the Examples.

The section headings are used herein for organizational purposes only, and are not to be construed as in any way limiting the subject matter described.

Standard techniques may be used for recombinant DNA molecule, protein, and antibody production, as well as for tissue culture and cell transformation. Enzymatic reactions and purification techniques are typically performed according to the manufacturer's specifications or as commonly accomplished in the art using conventional procedures such as those set forth in Sambrook et al. (Molecular Cloning: A Laboratory Manual. Cold Spring Harbor Laboratory Press, Cold Spring Harbor, N.Y. [1989]), or as described herein. Unless specific definitions are provided, the nomenclature utilized in connection with, and the laboratory procedures and techniques of analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

DEFINITIONS

As utilized in accordance with the present disclosure, the following terms unless otherwise indicated, shall be understood to have the following meanings:

The term "Ang-2" refers to the polypeptide set forth in FIG. 6 of U.S. Pat. No. 6,166,185 ("Tie-2 ligand-2") or fragments thereof as well as related polypeptides which include allelic variants, splice variants, derivatives, substitution, deletions, and/or insertion variants, fusion peptides and polypeptides, and interspecies homologs. The Ang-2 polypeptide may or may not include additional terminal residues, e.g., leader sequences, targeting sequences, amino terminal methionine, amino terminal methionine and lysine residues, and/or tag or fusion proteins sequences, depending on the manner in which it is prepared.

The term "biologically active" when used in relation to Ang-2 or an Ang-2 specific binding agent refers to a peptide or polypeptide having at least one activity characteristic of Ang-2 or of an Ang-2 specific binding agent. A specific binding agent of Ang-2 may have agonist, antagonist, or neutralizing or blocking activity with respect to at least one biological activity of Ang-2.

The term "specific binding agent" refers to a molecule, preferably a proteinaceous molecule, that binds Ang-2 (and variants and derivatives thereof as defined herein) with a greater affinity than other angiopoietins. A specific binding agent may be a protein, peptide, nucleic acid, carbohydrate, lipid, or small molecular weight compound which binds preferentially to Ang-2. In a preferred embodiment, the specific binding agent according to the present invention is an antibody, such as a polyclonal antibody, a monoclonal antibody (mAb), a chimeric antibody, a CDR-grafted antibody, a multispecific antibody, a bi-specific antibody, a catalytic antibody, a humanized antibody, a human antibody, an anti-idiotypic (anti-Id) antibody, and antibodies that can be labeled in soluble or bound form, as well as fragments, variants or derivatives thereof, either alone or in combination with other amino acid sequences, provided by known techniques. Such techniques include, but are not limited to enzymatic cleavage, chemical cleavage, peptide synthesis or recombinant techniques. The anti-Ang-2 specific binding agents of the present invention are capable of binding portions of Ang-2 that modulate, e.g., inhibit or promote, the biological activity of Ang-2 and/or other Ang-2-associated activities.

The term "polyclonal antibody" refers to a heterogeneous mixture of antibodies that recognize and bind to different epitopes on the same antigen. Polyclonal antibodies may be obtained from crude serum preparations or may be purified using, for example, antigen affinity chromatography, or Protein A/Protein G affinity chromatography.

The term "monoclonal antibodies" refers to a collection of antibodies encoded by the same nucleic acid molecule which are optionally produced by a single hybridoma or other cell line, or by a transgenic mammal such that each monoclonal antibody will typically recognize the same epitope on the antigen. The term "monoclonal" is not limited to any particular method for making the antibody, nor is the term limited to antibodies produced in a particular species, e.g., mouse, rat, etc.

The term "chimeric antibodies" refers to antibodies in which a portion of the heavy and/or light chain is identical with or homologous to a corresponding sequence in an antibody derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, that exhibit the desired biological activity (i.e., the ability to specifically bind Ang-2). See, U.S. Pat. No. 4,816,567 and Morrison et al., *Proc Natl Acad Sci (USA)*, 81:6851-6855 [1985].

The term "CDR grafted antibody" refers to an antibody in which the CDR from one antibody of a particular species or isotype is recombinantly inserted into the framework of another antibody of the same or different species or isotype.

The term "multi-specific antibody" refers to an antibody having variable regions that recognize more than one epitope on one or more antigens. A subclass of this type of antibody is a "bi-specific antibody" which recognizes two distinct epitopes on the same or different antigens.

"Catalytic" antibodies refers to antibodies wherein one or more cytotoxic, or more generally one or more biologically active, moieties are attached to the targeting binding agent.

The term "humanized antibody" refers to a specific type of CDR-grafted antibody in which the antibody framework region is derived from a human but each CDR is replaced with that derived from another species, such as a murine CDR. The term "CDR" is defined infra.

The term "fully human" antibody refers to an antibody in which both the CDR and the framework are derived from one or more human DNA molecules.

The term "anti-idiotype" antibody refers to any antibody that specifically binds to another antibody that recognizes an antigen. Production of anti-idiotype antibodies can be performed by any of the methods described herein for production of an Ang-2-specific antibodies except that these antibodies arise from e.g., immunization of an animal with an Ang-2-specific antibody or Ang-2-binding fragment thereof, rather than Ang-2 polypeptide itself or a fragment thereof.

The term "variants," as used herein, include those polypeptides wherein amino acid residues are inserted into, deleted from and/or substituted into the naturally occurring (or at least a known) amino acid sequence for the binding agent. Variants of the invention include fusion proteins as described below.

"Derivatives" include those binding agents that have been chemically modified in some manner distinct from insertion, deletion, or substitution variants.

"Specifically binds Ang-2" refers to the ability of a specific binding agent (such as an antibody or fragment thereof) of the present invention to recognize and bind mature, full-length or partial-length human Ang-2 polypeptide, or an ortholog thereof, such that its affinity (as determined by, e.g., Affinity ELISA or BIAcore assays as described herein) or its neutralization capability (as determined by e.g., Neutralization ELISA assays described herein, or similar assays) is at least 10 times as great, but optionally 50 times as great, 100, 250 or 500 times as great, or even at least 1000 times as great as the affinity or neutralization capability of the same for any other angiopoietin or other peptide or polypeptide.

The term "antigen binding domain" or "antigen binding region" refers to that portion of the specific binding agent (such as an antibody molecule) which contains the specific binding agent amino acid residues (or other moieties) that interact with an antigen and confer on the binding agent its specificity and affinity for the antigen. In an antibody, the antigen-binding domain is commonly referred to as the "complementarity-determining region, or CDR."

The term "epitope" refers to that portion of any molecule capable of being recognized by and bound by a specific binding agent, e.g. an antibody, at one or more of the binding agent's antigen binding regions. Epitopes usually consist of chemically active surface groupings of molecules, such as for example, amino acids or carbohydrate side chains, and have specific three-dimensional structural characteristics as well as specific charge characteristics. Epitopes as used herein may be contiguous or non-contiguous. Moreover, epitopes may be mimetic in that they comprise a three dimensional structure that is identical to the epitope used to generate the antibody, yet comprise none or only some of the amino acid residues found in the Ang-2 used to stimulate the antibody immune response.

The term "inhibiting and/or neutralizing epitope" is an epitope, which when bound by a specific binding agent such as an antibody, results in the loss of (or at least the decrease in) biological activity of the molecule, cell, or organism containing such epitope, in vivo, in vitro, or in situ. In the context of the present invention, the neutralizing epitope is located on or is associated with a biologically active region of Ang-2. Alternatively, the term "activating epitope" is an epitope, which when bound by a specific binding agent of the invention, such as an antibody, results in activation, or at least maintenance of a biologically active conformation, of Ang-2.

The term "antibody fragment" refers to a peptide or polypeptide which comprises less than a complete, intact antibody. Complete antibodies comprise two functionally independent parts or fragments: an antigen binding fragment known as "Fab," and a carboxy terminal crystallizable fragment known as the "Fc" fragment. The Fab fragment includes the first constant domain from both the heavy and light chain (CH1 and CL1) together with the variable regions from both the heavy and light chains that bind the specific antigen. Each of the heavy and light chain variable regions includes three complementarity determining regions (CDRs) and framework amino acid residues which separate the individual CDRs. The Fc region comprises the second and third heavy chain constant regions (CH2 and CH3) and is involved in effector functions such as complement activation and attack by phagocytic cells. In some antibodies, the Fc and Fab regions are separated by an antibody "hinge region," and depending on how the full length antibody is proteolytically cleaved, the hinge region may be associated with either the Fab or Fc fragment. For example, cleavage of an antibody with the protease papain results in the hinge region being associated with the resulting Fc fragment, while cleavage with the protease pepsin provides a fragment wherein the hinge is associated with both Fab fragment simultaneously. Because the two Fab fragments are in fact covalently linked following pepsin cleavage, the resulting fragment is termed the F(ab')2 fragment.

An Fc domain may have a relatively long serum half-life, whereas a Fab is short-lived. [Capon et al., Nature, 337: 525-31 (1989)] When expressed as part of a fusion protein, an Fc domain can impart longer half-life or incorporate such functions as Fc receptor binding, Protein A binding, complement fixation and perhaps even placental transfer into the protein to which it is fused. The Fe region may be a naturally occurring Fe region, or may be altered to improve certain qualities, such as therapeutic qualities or circulation time.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. The variable regions typically differ extensively in amino acid sequence even among antibodies of the same species. The variable region of an antibody typically determines the binding and specificity of each particular antibody for its particular antigen. The variability in sequence is concentrated in those regions referred to as complementarity-determining regions (CDRs), while the more highly conserved regions in the variable domain are called framework regions (FR). The CDRs of the light and heavy chains contain within them the amino acids which are largely responsible for the direct interaction of the antibody with antigen, however, amino acids in the FRs can significantly affect antigen binding/recognition as discussed herein infra.

The term "light chain" when used in reference to an antibody collectively refers to two distinct types, called kappa (k) or lambda (l) based on the amino acid sequence of the constant domains.

The term "heavy chain" when used in reference to an antibody collectively refers to five distinct types, called alpha, delta, epsilon, gamma and mu, based on the amino acid sequence of the heavy chain constant domain. The combination of heavy and light chains give rise to five known classes of antibodies: IgA, IgD, IgE, IgG and IgM, respectively, including four known subclasses of IgG, designated as $IgG_1$, $IgG_2$, $IgG_3$ and $IgG_4$.

The term "naturally occurring" when used in connection with biological materials such as nucleic acid molecules, polypeptides, host cells, and the like, refers to those which are found in nature and not modified by a human being.

The term "isolated" when used in relation to Ang-2 or to a specific binding agent of Ang-2 refers to a compound that is free from at least one contaminating polypeptide or compound that is found in its natural environment, and preferably substantially free from any other contaminating mammalian polypeptides that would interfere with its therapeutic or diagnostic use.

The term "mature" when used in relation to Ang-2, anti-Ang-2 antibody, or to any other proteinaceous specific binding agent of Ang-2 refers to a peptide or a polypeptide lacking a leader or signal sequence. When a binding agent of the invention is expressed, for example, in a prokaryotic host cell, the "mature" peptide or polypeptide may also include additional amino acid residues (but still lack a leader sequence) such as an amino terminal methionine, or one or more methionine and lysine residues. A peptide or polypeptide produced in this manner may be utilized with or without these additional amino acid residues having been removed.

The terms "effective amount" and "therapeutically effective amount" when used in relation to a specific binding agent of Ang-2 refers to an amount of a specific binding agent that is useful or necessary to support an observable change in the level of one or more biological activities of Ang-2. The change may be either an increase or decrease in the level of Ang-2 activity. Preferably, the change is a decrease in Ang-2 activity.

Specific Binding Agents and Antibodies

As used herein, the term "specific binding agent" refers to a molecule that has specificity for recognizing and binding Ang-2 as described herein. Suitable specific binding agents include, but are not limited to, antibodies and derivatives thereof, polypeptides, and small molecules. Suitable specific binding agents may be prepared using methods known in the art. An exemplary Ang-2 polypeptide specific binding agent of the present invention is capable of binding a certain portion of the Ang-2 polypeptide, and preferably modulating the activity or function of Ang-2 polypeptide.

Specific binding agents such as antibodies and antibody fragments that specifically bind Ang-2 polypeptides are within the scope of the present invention. The antibodies may be polyclonal including mono-specific polyclonal, monoclonal (mAbs), recombinant, chimeric, humanized such as CDR-grafted, human, single chain, catalytic, multi-specific and/or bi-specific, as well as fragments, variants, and/or derivatives thereof.

Polyclonal antibodies directed toward an Ang-2 polypeptide generally are produced in animals (e.g., rabbits, hamsters, goats, sheep, horses, pigs, rats, gerbils, guinea pigs, mice, or any other suitable mammal, as well as other non-mammal species) by means of multiple subcutaneous or intraperitoneal injections of Ang-2 polypeptide or a fragment thereof with or without an adjuvant. Such adjuvants include, but are not limited to, Freund's complete and incomplete, mineral gels such as aluminum hydroxide, and surface-active substances such as lysolecithin, pluronic polyols, polyanions, peptides, oil emulsions, keyhole limpet hemocyanin, and dinitrophenol. BCG (bacilli Calmette-Guerin) and Corynebacterium parvum are potentially useful human adjuvants. It may be useful to conjugate an antigen polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-Ang-2 polypeptide antibody titer which can be determined using the assays described herein under "Examples". Polyclonal antibodies may be utilized in the sera from which they were detected, or may be purified from the sera, using, for example, antigen affinity chromatography or Protein A or G affinity chromatography.

Monoclonal antibodies directed toward Ang-2 polypeptides can be produced using, for example but without limitation, the traditional "hybridoma" method or the newer "phage display" technique. For example, monoclonal antibodies of the invention may be made by the hybridoma method as described in Kohler et al., *Nature* 256:495 [1975]; the human B-cell hybridoma technique [Kosbor et al., *Immunol Today* 4:72 (1983); Cote et al., *Proc Natl Acad Sci (USA)* 80: 2026-2030 (1983); Brodeur et al., *Monoclonal Antibody Production Techniques and Applications,* pp. 51-63, Marcel Dekker, Inc., New York, (1987)] and the EBV-hybridoma technique [Cole et al., *Monoclonal Antibodies and Cancer Therapy,* Alan R Liss Inc, New York N.Y., pp 77-96, (1985)]. Also provided by the invention are hybridoma cell lines that produce monoclonal antibodies reactive with Ang-2 polypeptides.

When the hybridoma technique is employed, myeloma cell lines can be used. Such cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas). For example, cell lines used in mouse fusions are Sp-20, P3-X63/Ag8, P3-X63-Ag8.653, NS1/1.Ag 4 1, Sp210-Ag14, FO, NSO/U, MPC-11, MPC 11-X45-GTG 1.7 and S194/5XX0 Bul; cell lines used in rat fusions are R210.RCY3, Y3-Ag 1.2.3, IR983F and 4B210. Other cell lines useful for cell fusions are U-266, GM1500-GRG2, LICR-LON-HMy2 and UC729-6. Hybridomas and other cell lines that produce monoclonal antibodies are contemplated to be novel compositions of the present invention.

The phage display technique may also be used to generate monoclonal antibodies from any species. Preferably, this technique is used to produce fully human monoclonal antibodies in which a polynucleotide encoding a single Fab or Fv antibody fragment is expressed on the surface of a phage particle. [Hoogenboom et al., *J Mol Biol* 227: 381 (1991); Marks et al., *J Mol Biol* 222: 581 (1991); see also U.S. Pat. No. 5,885,793)]. Each phage can be "screened" using binding assays described herein to identify those antibody fragments having affinity for Ang-2. Thus, these processes mimic immune selection through the display of antibody fragment repertoires on the surface of filamentous bacteriophage, and subsequent selection of phage by their binding to Ang-2. One such procedure is described in PCT Application No. PCT/US98/17364, filed in the name of Adams et al., which describes the isolation of high affinity and functional agonistic antibody fragments for MPL- and msk-receptors using such an approach. In this approach, a complete repertoire of human antibody genes can be created by cloning naturally rearranged human V genes from peripheral blood lymphocytes as previously described [Mullinax et al., *Proc Natl Acad Sci (USA)* 87: 8095-8099 (1990)].

Once a polynucleotide sequences are identified which encode each chain of the full length monoclonal antibody or the Fab or Fv fragment(s) of the invention, host cells, either eukaryotic or prokaryotic, may be used to express the monoclonal antibody polynucleotides using recombinant techniques well known and routinely practiced in the art. Alternatively, transgenic animals are produced wherein a polynucleotide encoding the desired specific binding agent is introduced into the genome of a recipient animal, such as, for example, a mouse, rabbit, goat, or cow, in a manner that permits expression of the polynucleotide molecules encoding a monoclonal antibody or other specific binding agent. In one aspect, the polynucleotides encoding the monoclonal antibody or other specific binding agent can be ligated to mammary-specific regulatory sequences, and the chimeric polynucleotides can be introduced into the germline of the target animal. The resulting transgenic animal then produces the desired antibody in its milk [Pollock et al., *J Immunol Meth* 231:147-157 (1999); Little et al., *Immunol Today* 8:364-370 (2000)]. In addition, plants may be used to express and produce Ang-2 specific binding agents such as monoclonal antibodies by transfecting suitable plants with the polynucleotides encoding the monoclonal antibodies or other specific binding agents.

In another embodiment of the present invention, a monoclonal or polyclonal antibody or fragment thereof that is derived from other than a human species may be "humanized" or "chimerized". Methods for humanizing non-human antibodies are well known in the art. (see U.S. Pat. Nos. 5,859,205, 5,585,089, and 5,693,762). Humanization is performed, for example, using methods described in the art [Jones et al., *Nature* 321: 522-525 (1986); Riechmann et al., *Nature,* 332: 323-327 (1988); Verhoeyen et al., *Science* 239: 1534-1536 (1988)] by substituting at least a portion of, e.g. a rodent, complementarity-determining region (CDRs) for the corresponding regions of a human antibody. The invention also provides variants and derivatives of these human antibodies as discussed herein and well known in the art.

Also encompassed by the invention are fully human antibodies that bind Ang-2 polypeptides, as well as, fragments, variants and/or derivatives thereof. Such antibodies can be produced using the phage display technique described above. Alternatively, transgenic animals (e.g., mice) that are capable of producing a repertoire of human antibodies in the absence of endogenous immunoglobulin production can be used to generate such antibodies. This can be accomplished by immunization of the animal with an Ang-2 antigen or fragments thereof where the Ang-2 fragments have an amino acid sequence that is unique to Ang-2. Such immunogens can be optionally conjugated to a carrier. See, for example, Jakobovits et al., *Proc Natl Acad Sci (USA),* 90: 2551-2555 (1993); Jakobovits et al., *Nature* 362: 255-258 (1993); Bruggermann et al., *Year in Immuno,* 7: 33 (1993). In one method, such transgenic animals are produced by incapacitating the endogenous loci encoding the heavy and light immunoglobulin chains therein, and inserting loci encoding human heavy and light chain proteins into the genome thereof. Partially modified animals, that are those having less than the full complement of these modifications, are then crossbred to obtain an animal having all of the desired immune system modifications. When administered an immunogen, these transgenic animals are capable of producing antibodies with human variable regions, including human (rather than e.g., murine) amino acid sequences, that are immuno-specific for the desired antigens. See PCT application Nos., PCT/US96/05928 and PCT/US93/06926. Additional methods are described in U.S. Pat. No. 5,545,807, PCT application Nos. PCT/US91/245, PCT/GB89/01207, and in EP 546073B1 and EP 546073A1. Human antibodies may also be produced by the expression of recombinant DNA in host cells or by expression in hybridoma cells as described herein.

Transgenesis is achieved in a number of different ways. See, for example, Bruggeman et al., *Immunol Today* 17:391-7 (1996). In one approach, a minilocus is constructed such that gene segments in a germline configuration are brought artificially close to each other. Due to size limitations (i.e., having generally less than 30 kb), the resulting minilocus will contain a limited number of differing gene segments, but is still capable of producing a large repertoire of antibodies.

Miniloci containing only human DNA sequences, including promoters and enhancers are fully functional in the transgenic mouse.

When larger number of gene segments are desired in the transgenic animal, yeast artificial chromosomes (YACs) are utilized. YACs can range from several hundred kilobases to 1 Mb and are introduced into the mouse (or other appropriate animal) genome via microinjection directly into an egg or via transfer of the YAC into embryonic stem (ES)-cell lines. In general, YACs are transferred into ES cells by lipofection of the purified DNA, or yeast spheroplast fusion wherein the purified DNA is carried in micelles and fusion is carried out in manner similar to hybridoma fusion protocols. Selection of desired ES cells following DNA transfer is accomplished by including on the YAC any of the selectable markers known in the art.

As another alternative, bacteriophage P1 vectors are used which are amplified in a bacterial *E. coli* host. While these vectors generally carry less inserted DNA than a YAC, the clones are readily grown in high enough yield to permit direct microinjection into a mouse egg. Use of a cocktail of different P1 vectors has been shown to lead to high levels of homologous recombination.

Once an appropriate transgenic mouse (or other appropriate animal) has been identified, using any of the techniques known in the art to detect serum levels of a circulating antibody (e.g., ELISA), the transgenic animal is crossed with a mouse in which the endogenous Ig locus has been disrupted. The result provides progeny wherein essentially all B cells express human antibodies.

As still another alternative, the entire animal Ig locus is replaced with the human Ig locus, wherein the resulting animal expresses only human antibodies. In another approach, portions of the animal's locus are replaced with specific and corresponding regions in the human locus. In certain cases, the animals resulting from this procedure may express chimeric antibodies, as opposed to fully human antibodies, depending on the nature of the replacement in the mouse Ig locus.

Human antibodies can also be produced by exposing human splenocytes (B or T cells) to an antigen in vitro, then reconstituting the exposed cells in an immunocompromised mouse, e.g. SCID or nod/SCID. See Brams et al., *J Immunol*, 160: 2051-2058 [1998]; Carballido et al., *Nat Med*, 6: 103-106 [2000]. In one approach, engraftment of human fetal tissue into SCID mice (SCID-hu) results in long-term hematopoiesis and human T-cell development [McCune et al., *Science* 241: 1532-1639 (1988); Ifversen et al., *Sem Immunol* 8:243-248 (1996)]. Any humoral immune response in these chimeric mice is completely dependent on co-development of T-cells in the animals [Martensson et al., *Immunol* 83:1271-179 (1994)]. In an alternative approach, human peripheral blood lymphocytes are transplanted intraperitoneally (or otherwise) into SCID mice [Mosier et al., *Nature* 335:256-259 (1988)]. When the transplanted cells are treated with either a priming agent, such as Staphylococcal Enterotoxin A (SEA) [Martensson et al., *Immunol* 84: 224-230 (1995)], or anti-human CD40 monoclonal antibodies [Murphy et al., *Blood* 86:1946-1953 (1995)], higher levels of B cell production are detected.

Alternatively, an entirely synthetic human heavy chain repertoire is created from unrearranged V gene segments by assembling each human VH segment with D segments of random nucleotides together with a human J segment [Hoogenboom et al., *J Mol Biol* 227:381-388 (1992)]. Likewise, a light chain repertoire is constructed by combining each human V segment with a J segment [Griffiths et al., *EMBO J.* 13:3245-3260 (1994)]. Nucleotides encoding the complete antibody (i.e., both heavy and light chains) are linked as a single chain Fv fragment and this polynucleotide is ligated to a nucleotide encoding a filamentous phage minor coat protein. When this fusion protein is expressed on the surface of the phage, a polynucleotide encoding a specific antibody is identified by selection using an immobilized antigen.

In still another approach, antibody fragments are assembled as two Fab fragments by fusion of one chain to a phage protein and secretion of the other into bacterial periplasm [Hoogenboom et al., *Nucl Acids Res* 19:4133-4137 [1991]; Barbas et al., *Proc Natl Acad Sci (USA)* 88:7978-7982 (1991)].

Large-scale production of chimeric, humanized, CDR-grafted, and fully human antibodies, or fragments thereof, are typically produced by recombinant methods. Polynucleotide molecule(s) encoding the heavy and light chains of each antibody or fragments thereof, can be introduced into host cells and expressed using materials and procedures described herein. In a preferred embodiment, the antibodies are produced in mammalian host cells, such as CHO cells. Details of such production is described below.

Fusion Partners of Specific Binding Agents

In a further embodiment of the invention, the polypeptides comprising the amino acid sequence variable domains of Ang-2 antibodies, such as a heavy chain variable region with an amino acid sequence as described herein or a light chain variable region with an amino acid sequence as described herein, may be fused at either the N-terminus or the C-terminus to one or more domains of an Fc region of human IgG. When constructed together with a therapeutic protein such as the Fab of an Ang-2-specific antibody, an Fc domain can provide longer half-life or incorporate such functions as Fc receptor binding, Protein A binding, complement fixation and perhaps even placental transfer. [Capon et al., Nature, 337: 525-531 (1989)].

In one example, the antibody hinge, CH2 and CH3 regions may be fused at either the N-terminus or C-terminus of the specific binding agent polypeptides such as an anti-Ang-2 Fab or Fv fragment (obtained, e.g., from a phage display library) using methods known to the skilled artisan. The resulting fusion protein may be purified by use of a Protein A or Protein G affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, decrease aggregation problems, etc. Other examples known in the art include those wherein the Fc region, which may be human or another species, or may be synthetic, is fused to the N-terminus of CD30L to treat Hodgkin's Disease, anaplastic lymphoma and T-cell leukemia (U.S. Pat. No. 5,480,981), the Fc region is fused to the TNF receptor to treat septic shock [Fisher et al., N Engl J Med, 334: 1697-1702 (1996)], and the Fc region is fused to the Cd4 receptor to treat AIDS [Capon et al., Nature, 337: 525-31 (1989)].

Catalytic antibodies are another type of fusion molecule and include antibodies to which one or more cytotoxic, or more generally one or more biologically active, moieties are attached to the specific binding agent. See, for example [Rader et al., *Chem Eur J* 12:2091-2095 (2000)]. Cytotoxic agents of this type improve antibody-mediated cytotoxicity, and include such moieties as cytokines that directly or indirectly stimulate cell death, radioisotopes, chemotherapeutic drugs (including prodrugs), bacterial toxins (ex. pseudomonas exotoxin, diphtheria toxin, etc.), plant toxins (ex. ricin, gelonin, etc.), chemical conjugates (e.g., maytansinoid toxins, calechaemicin, etc.), radioconjugates, enzyme conjugates (RNase conjugates, antibody-directed enzyme/prodrug therapy [ADEPT]]), and the like. In one aspect, the cytotoxic agent can be "attached" to one component of a bi-specific or multi-specific antibody by binding of this agent to one of the alternative antigen recognition sites on the antibody. As an alternative, protein cytotoxins can be expressed as fusion proteins with the specific binding agent following ligation of a polynucleotide encoding the toxin to a polynucleotide encoding the binding agent. In still another alternative, the specific binding agent can be covalently modified to include the desired cytotoxin.

Examples of such fusion proteins are immunogenic polypeptides, proteins with long circulating half lives, such as immunoglobulin constant regions, marker proteins, proteins or polypeptides that facilitate purification of the desired specific binding agent polypeptide, and polypeptide sequences that promote formation of multimeric proteins (such as leucine zipper motifs that are useful in dimer formation/stability).

This type of insertional variant generally has all or a substantial portion of the native molecule, linked at the N- or C-terminus, to all or a portion of a second polypeptide. For example, fusion proteins typically employ leader sequences from other species to permit the recombinant expression of a protein in a heterologous host. Another useful fusion protein includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

There are various commercially available fusion protein expression systems that may be used in the present invention. Particularly useful systems include but are not limited to the glutathione-S-transferase (GST) system (Pharmacia), the maltose binding protein system (NEB, Beverley, Mass.), the FLAG system (IBI, New Haven, Conn.), and the 6×His system (Qiagen, Chatsworth, Calif.). These systems are capable of producing recombinant polypeptides bearing only a small number of additional amino acids, which are unlikely to affect the antigenic ability of the recombinant polypeptide. For example, both the FLAG system and the 6×His system add only short sequences, both of which are known to be poorly antigenic and which do not adversely affect folding of the polypeptide to its native conformation. Another N-terminal fusion that is contemplated to be useful is the fusion of a Met-Lys dipeptide at the N-terminal region of the protein or peptides. Such a fusion may produce beneficial increases in protein expression or activity.

A particularly useful fusion construct may be one in which a specific binding agent peptide is fused to a hapten to enhance immunogenicity of a specific binding agent fusion construct which is useful, for example, in the production of anti-idiotype antibodies of the invention. Such fusion constructs to increase immunogenicity are well known to those of skill in the art, for example, a fusion of specific binding agent with a helper antigen such as hsp70 or peptide sequences such as from diphtheria toxin chain or a cytokine such as IL-2 will be useful in eliciting an immune response. In other embodiments, fusion construct can be made which will enhance the targeting of the antigen binding agent compositions to a specific site or cell.

Other fusion constructs including heterologous polypeptides with desired properties, e.g., an Ig constant region to prolong serum half-life or an antibody or fragment thereof for targeting also are contemplated. Other fusion systems produce polypeptide hybrids where it is desirable to excise the fusion partner from the desired polypeptide. In one embodiment, the fusion partner is linked to the recombinant specific binding agent polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.

The invention also provides fusion polypeptides comprising all or part of a variable domain of an Ang-2 antibody, such as a heavy chain variable region with an amino acid sequence as described herein or a light chain variable region with an amino acid sequence as described herein in combination with truncated tissue factor (tTF), a vascular targeting agent consisting of a truncated form of a human coagulation-inducing protein that acts as a tumor blood vessel clotting agent. The fusion of tTF to the anti-Ang-2 antibody, or fragments thereof may facilitate the delivery of anti-Ang-2 to target cells.

Variants of Specific Binding Agents

Variants of Specific Binding Agents of the present invention include insertion, deletion, and/or substitution variants. In one aspect of the invention, insertion variants are provided wherein one or more amino acid residues supplement a specific binding agent amino acid sequence. Insertions may be located at either or both termini of the protein, or may be positioned within internal regions of the specific binding agent amino acid sequence. Insertional variants with additional residues at either or both termini can include, for example, fusion proteins and proteins including amino acid tags or labels. Insertion variants include specific binding agent polypeptides wherein one or more amino acid residues are added to a specific binding agent amino acid sequence, or fragment thereof.

Variant products of the invention also include mature specific binding agent products. Such specific binding agent products have the leader or signal sequences removed, however the resulting protein has additional amino terminal residues as compared to wild-type Ang-2 polypeptide. The additional amino terminal residues may be derived from another protein, or may include one or more residues that are not identifiable as being derived from a specific protein. Specific binding agent products with an additional methionine residue at position −1 (Met$^{-1}$-specific binding agent) are contemplated, as are specific binding agent products with additional methionine and lysine residues at positions −2 and −1 (Met$^-_2$-Lys$^{-1}$-specific binding agent). Variants of specific binding agents having additional Met, Met-Lys, Lys residues (or one or more basic residues in general) are particularly useful for enhanced recombinant protein production in bacterial host cells.

The invention also embraces specific binding agent variants having additional amino acid residues that arise from use of specific expression systems. For example, use of commercially available vectors that express a desired polypeptide as part of glutathione-S-transferase (GST) fusion product provides the desired polypeptide having an additional glycine residue at amino acid position −1 after cleavage of the GST component from the desired polypeptide. Variants which result from expression in other vector systems are also contemplated, including those wherein poly-histidine tags are incorporated into the amino acid sequence, generally at the carboxy and/or amino terminus of the sequence.

Insertional variants also include fusion proteins as described above, wherein the amino and/or carboxy termini of the specific binding agent-polypeptide is fused to another polypeptide, a fragment thereof, or amino acid sequences which are not generally recognized to be part of any specific protein sequence.

In another aspect, the invention provides deletion variants wherein one or more amino acid residues in a specific binding agent polypeptide are removed. Deletions can be effected at one or both termini of the specific binding agent polypeptide, or from removal of one or more residues within the specific binding agent amino acid sequence. Deletion variants necessarily include all fragments of a specific binding agent polypeptide.

Antibody fragments include those portions of the antibody that bind to an epitope on the antigen polypeptide. Examples of such fragments include Fab and F(ab')$_2$ fragments generated, for example, by enzymatic or chemical cleavage of full-length antibodies. Other binding fragments include those generated by recombinant DNA techniques, such as the expression of recombinant plasmids containing nucleic acid sequences encoding antibody variable regions. The invention also embraces polypeptide fragments of an Ang-2 binding agent wherein the fragments maintain the ability to specifically bind an Ang-2 polypeptide. Fragments comprising at least 5, 10, 15, 20, 25, 30, 35, 40, 45 or 50 or more consecutive amino acids of a peptide or polypeptide of the invention are comprehended herein. Preferred polypeptide fragments display immunological properties unique to or specific for the antigen-binding agent so of the invention. Fragments of the invention having the desired immunological properties can be prepared by any of the methods well known and routinely practiced in the art.

In still another aspect, the invention provides substitution variants of specific binding agents of the invention. Substitution variants are generally considered to be "similar" to the original polypeptide or to have a certain "percent identity" to the original polypeptide, and include those polypeptides wherein one or more amino acid residues of a polypeptide are removed and replaced with alternative residues. In one aspect, the substitutions are conservative in nature, however, the invention embraces substitutions that are also non-conservative.

Identity and similarity of related polypeptides can be readily calculated by known methods. Such methods include, but are not limited to, those described in Computational Molecular Biology, Lesk, A. M., ed., Oxford University Press, New York (1988); Biocomputing: Informatics and Genome Projects, Smith, D. W., ed., Academic Press, New York (1993); Computer Analysis of Sequence Data, Part 1, Griffin, A. M., and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., M. Stockton Press, New York (1991); and Carillo et al., *SIAM J. Applied Math.*, 48:1073 (1988).

Preferred methods to determine the relatedness or percent identity of two polypeptides are designed to give the largest match between the sequences tested. Methods to determine identity are described in publicly available computer programs. Preferred computer program methods to determine identity between two sequences include, but are not limited to, the GCG program package, including GAP (Devereux et al., *Nucl. Acid. Res.*, 12:387 (1984); Genetics Computer Group, University of Wisconsin, Madison, Wis., BLASTP, BLASTN, and FASTA (Altschul et al., *J. Mol. Biol.*, 215:403-410 (1990)). The BLASTX program is publicly available from the National Center for Biotechnology Information (NCBI) and other sources (*BLAST Manual*, Altschul et al. NCB/NLM/NIH Bethesda, Md. 20894; Altschul et al., supra (1990)). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in certain embodiments, the selected alignment method (GAP program) will result in an alignment that spans at least ten percent of the full length of the target polypeptide being compared, i.e., at least 40 contiguous amino acids where sequences of at least 400 amino acids are being compared, 30 contiguous amino acids where sequences of at least 300 to about 400 amino acids are being compared, at least 20 contiguous amino acids where sequences of 200 to about 300 amino acids are being compared, and at least 10 contiguous amino acids where sequences of about 100 to 200 amino acids are being compared.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is typically calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see Dayhoff et al., *Atlas of Protein Sequence and Structure*, 5(3) (1978) for the PAM 250 comparison matrix; Henikoff et al., *Proc. Natl. Acad. Sci* USA, 89:10915-10919 (1992) for the BLOSUM 62 comparison matrix) is also used by the algorithm.

In certain embodiments, the parameters for a polypeptide sequence comparison include the following:

Algorithm: Needleman et al., *J. Mol. Biol.*, 48:443-453 (1970);
Comparison matrix: BLOSUM 62 from Henikoff et al., supra (1992);
Gap Penalty: 12
Gap Length Penalty: 4
Threshold of Similarity: 0

The GAP program may be useful with the above parameters. In certain embodiments, the aforementioned parameters are the default parameters for polypeptide comparisons (along with no penalty for end gaps) using the GAP algorithm.

In certain embodiments, the parameters for polynucleotide molecule sequence comparisons include the following:

Algorithm: Needleman et al., supra (1970);
Comparison matrix: matches=+10, mismatch=0
Gap Penalty: 50
Gap Length Penalty: 3

The GAP program may also be useful with the above parameters. The aforementioned parameters are the default parameters for polynucleotide molecule comparisons.

Other exemplary algorithms, gap opening penalties, gap extension penalties, comparison matrices, thresholds of similarity, etc. may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference for any purpose.

The amino acids may have either L or D stereochemistry (except for Gly, which is neither L nor D) and the polypeptides and compositions of the present invention may comprise a combination of stereochemistries. However, the L stereochemistry is preferred. The invention also provides reverse molecules wherein the amino terminal to carboxy terminal sequence of the amino acids is reversed. For example, the reverse of a molecule having the normal sequence $X_1$-$X_2$-$X_3$ would be $X_3$-$X_2$-$X_1$. The invention also provides retro-reverse molecules wherein, as above, the amino terminal to carboxy terminal sequence of amino acids is reversed and residues that are normally "L" enantiomers are altered to the "D" stereoisomer form.

Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include, without limitation: aminoadipic acid, beta-alanine, beta-aminopropionic acid, aminobutyric acid, piperidinic acid, aminocaprioic acid, aminoheptanoic acid, aminoisobutyric acid, aminopimelic acid, diaminobutyric acid, desmosine, diaminopimelic acid, diaminopropionic acid, N-ethylglycine, N-ethylaspargine, hyroxylysine, allo-hydroxylysine, hydroxyproline, isodesmosine, allo-isoleucine, N-methylglycine, sarcosine, N-methylisoleucine, N-methylvaline, norvaline, norleucine, orithine, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and amino acids (e.g., 4-hydroxyproline).

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues may be divided into classes based on common side chain properties:

1) hydrophobic: Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human antibody that are homologous with non-human antibodies, or into the non-homologous regions of the molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.*, 157:105-131 (1982). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln, Glu, Asp | Gln |
| Asp | Glu, Gln, Asn | Glu |
| Cys | Ser, Ala | Ser |
| Gln | Asn, Glu, Asp | Asn |
| Glu | Asp, Asn, Gln | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., *Curr. Op. in Biotech.*, 7(4):422-427 (1996), Chou et al., *Biochemistry*, 13(2):222-245 (1974); Chou et al., *Biochemistry*, 113(2):211-222 (1974); Chou et al., *Adv. Enzymol. Relat. Areas Mol. Biol.*, 47:45-148 (1978); Chou et al., *Ann. Rev. Biochem.*, 47:251-276 and Chou et al., *Biophys. J.*, 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., *Nucl. Acid. Res.*, 27(1):244-247 (1999). It has been suggested (Brenner et al., *Curr. Op. Struct. Biol.*, 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., *Curr. Opin. Struct. Biol.*, 7(3): 377-87 (1997); Sippl et al., *Structure*, 4(1):15-19 (1996)), "profile analysis" (Bowie et al., *Science*, 253:164-170 (1991); Gribskov et al., *Meth. Enzym.*, 183:146-159 (1990); Gribskov et al., *Proc. Nat. Acad. Sci.*, 84(13):4355-4358 (1987)), and "evolutionary linkage" (See Holm, supra (1999), and Brenner, supra (1997)).

In certain embodiments, antibody variants include glycosylation variants wherein the number and/or type of glycosylation site has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (5) confer or modify other functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991).

The specific binding agent molecules of this invention that are polypeptide or peptide substitution variants may have up to about ten to twelve percent of the original amino acid sequence replaced. For antibody variants, the heavy chain may have 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 amino acid replaced, while the light chain may have 25, 24, 23, 22, 21, 20, 19, 18, 17, 16, 15, 14, 13, 12, 11, 10, 9, 8, 7, 6, 5, 4, 3, 2, or 1 amino acid replaced.

Derivatives of Specific Binding Agents

The invention also provides derivatives of specific binding agent polypeptides. Derivatives include specific binding agent polypeptides bearing modifications other than insertion, deletion, or substitution of amino acid residues. Preferably, the modifications are covalent in nature, and include for example, chemical bonding with polymers, lipids, other organic, and inorganic moieties. Derivatives of the invention may be prepared to increase circulating half-life of a specific binding agent polypeptide, or may be designed to improve targeting capacity for the polypeptide to desired cells, tissues, or organs.

The invention further embraces derivative binding agents covalently modified to include one or more water soluble polymer attachments such as polyethylene glycol, polyoxyethylene glycol, or polypropylene glycol as described U.S. Pat. Nos. 4,640,835, 4,496,689, 4,301,144, 4,670,417, 4,791,192 and 4,179,337. Still other useful polymers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide copolymer, polyoxyethylated polyols (e.g., glycerol) and polyvinyl alcohol, as well as mixtures of these polymers. Particularly preferred are specific binding agent products covalently modified with polyethylene glycol (PEG) subunits. Water-soluble polymers may be bonded at specific positions, for example at the amino terminus of the specific binding agent products, or randomly attached to one or more side chains of the polypeptide. The use of PEG for improving the therapeutic capacity for specific binding agent, and for humanized antibodies in particular, is described in U.S. Pat. No. 6,133,426 to Gonzales et al., issued Oct. 17, 2000.

Target Sites for Antibody Mutagenesis

Certain strategies can be employed to manipulate inherent properties of an Ang-2-specific antibody, such as the affinity of the antibody for its target. These strategies include the use of site-specific or random mutagenesis of the polynucleotide molecule encoding the antibody to generate antibody variants, followed by a screening step designed to recover antibody variants that exhibit the desired change, e.g. increased or decreased affinity.

The amino acid residues most commonly targeted in mutagenic strategies are those in the CDRs. As described supra, these regions contain the residues that actually interact with Ang-2 and other amino acids that affect the spatial arrangement of these residues. However, amino acids in the framework regions of the variable domains outside the CDR regions have also been shown to make substantial contributions to the antigen-binding properties of the antibody, and can be targeted to manipulate such properties. See Hudson, *Curr Opin Biotech,* 9:395-402 (1999) and references therein.

Smaller and more effectively screened libraries of antibody variants can be produced by restricting random or site-directed mutagenesis to sites in the CDRs that correspond to areas prone to "hyper-mutation" during the somatic affinity maturation process. See Chowdhury and Pastan, *Nature Biotech,* 17: 568-572 [1999] and references therein. The types of DNA elements known to define hyper-mutation sites in this manner include direct and inverted repeats, certain consensus sequences, secondary structures, and palindromes. The consensus DNA sequences include the tetrabase sequence Purine-G-Pyrimidine-A/T (i.e. A or G-G-C or T-A or T) and the serine codon AGY (wherein Y can be a C or a T).

Thus, an embodiment of the present invention includes mutagenic strategies with the goal of increasing the affinity of an antibody for its target. These strategies include mutagenesis of the entire variable heavy and light chain, mutagenesis of the CDR regions only, mutagenesis of the consensus hyper-mutation sites within the CDRs, mutagenesis of framework regions, or any combination of these approaches ("mutagenesis" in this context could be random or site-directed). Definitive delineation of the CDR regions and identification of residues comprising the binding site of an antibody can be accomplished though solving the structure of the antibody in question, and the antibody-ligand complex, through techniques known to those skilled in the art, such as X-ray crystallography. Various methods based on analysis and characterization of such antibody crystal structures are known to those of skill in the art and can be employed, although not definitive, to approximate the CDR regions. Examples of such commonly used methods include the Kabat, Chothia, AbM and contact definitions.

The Kabat definition is based on the sequence variability and is the most commonly used definition to predict CDR regions. [Johnson and Wu, *Nucleic Acids Res,* 28: 214-8 (2000)]. The Chothia definition is based on the location of the structural loop regions. [Chothia et al., *J Mol Biol,* 196: 901-17 (1986); Chothia et al., *Nature,* 342: 877-83 (1989)]. The AbM definition is a compromise between the Kabat and Chothia definition. AbM is an integral suite of programs for antibody structure modeling produced by Oxford Molecular Group [Martin et al., *Proc Natl Acad Sci (USA)* 86:9268-9272 (1989); Rees, et al., ABM™, a computer program for modeling variable regions of antibodies, Oxford, UK; Oxford Molecular, Ltd.]. The AbM suite models the tertiary structure of an antibody from primary sequencing using a combination of knowledge databases and ab init10 methods. An additional definition, known as the contact definition, has been recently introduced. [MacCallum et al., *J Mol Biol,* 5:732-45 (1996)]. This definition is based on an analysis of the available complex crystal structures.

By convention, the CDR regions in the heavy chain are typically referred to as H1, H2 and H3 and are numbered sequentially in order counting from the amino terminus to the carboxy terminus. The CDR regions in the light chain are typically referred to as L1, L2 and L3 and are numbered sequentially in order counting from the amino terminus to the carboxy terminus.

The CDR-H1 is approximately 10 to 12 residues in length and typically starts 4 residues after a Cys according to the Chothia and AbM definitions or typically 5 residues later according to the Kabat definition. The H1 is typically followed by a Trp, typically Trp-Val, but also Trp-Ile, or Trp-Ala. The length of H1 is approximately 10 to 12 residues according to the AbM definition while the Chothia definition excludes the last 4 residues.

The CDR-H2 typically starts 15 residues after the end of H1 according to the Kabat and AbM definition. The residues preceding H2 are typically Leu-Glu-Trp-Ile-Gly but there are a number of variations. H2 is typically followed by the amino acid sequence Lys/Arg-Leu/Ile/Val/Phe/Thr/Ala-Thr/Ser/Ile/Ala. According to the Kabat definition, the length of the H2 is approximately 16 to 19 residues where the AbM definition predicts the length to be typically 9 to 12 residues.

The CDR-H3 typically starts 33 residues after the end of H2 and is typically preceded by the amino acid sequence (typically Cys-Ala-Arg). The H3 is typically followed by the amino acid sequence-Gly. The length of H3 can be anywhere between 3 to 25 residues.

The CDR-L1 typically starts at approximately residue 24 and will typically follow a Cys. The residue after the CDR-L1 is always a Trp and will typically begin the sequence Trp-Tyr-Gln, Trp-Leu-Gln, Trp-Phe-Gln, or Trp-Tyr-Leu. The length of CDR-L1 is approximately 10 to 17 residues. The punitive CDR-L1 for the antibodies of the invention follows this pattern exactly with a Cys residue followed by 15 amino acids then Trp-Tyr-Gln.

The CDR-L2 starts approximately 16 residues after the end of L1. It will generally follow residues Ile-Tyr, Val-Tyr, Ile-Lys or Ile-Phe. The length of CDR-L2 is approximately 7 residues.

The CDR-L3 typically starts 33 residues after the end of L2 and typically follows a Cys. L3 is typically followed by the amino acid sequence Phe-Gly-XXX-Gly. The length of L3 is approximately 7 to 11 residues.

Various methods for modifying antibodies have been described in the art. For example, U.S. Pat. No. 5,530,101 (to Queen et al., Jun. 25, 1996) describes methods to produce humanized antibodies wherein the sequence of the humanized immunoglobulin heavy chain variable region framework is 65% to 95% identical to the sequence of the donor immunoglobulin heavy chain variable region framework. Each humanized immunoglobulin chain will usually comprise, in addition to the CDRs, amino acids from the donor immunoglobulin framework that are, e.g., capable of interacting with the CDRs to affect binding affinity, such as one or more amino acids which are immediately adjacent to a CDR in the donor immunoglobulin or those within about 3 angstroms as predicted by molecular modeling. The heavy and light chains may each be designed by using any one or all of various position criteria. When combined into an intact antibody, the humanized immunoglobulins of the present invention will be substantially non-immunogenic in humans and retain substantially the same affinity as the donor immunoglobulin to the antigen, such as a protein or other compound containing an epitope. See also, related methods in U.S. Pat. No. 5,693,761 to Queen, et al., issued Dec. 2, 1997 ("Polynucleotides encoding improved humanized immunoglobulins"); U.S. Pat. No. 5,693,762 to Queen, et al., issued Dec. 2, 1997 ("Humanized Immunoglobulins"); U.S. Pat. No. 5,585,089 to Queen, et al. issued Dec. 17, 1996 ("Humanized Immunoglobulins").

In one example, U.S. Pat. No. 5,565,332 to Hoogenboom et al. issued Oct. 15, 1996 ("Production of chimeric antibodies—a combinatorial approach") describes methods for the production of antibodies, and antibody fragments which have similar binding specificity as a parent antibody but which have increased human characteristics. Humanized antibodies are obtained by chain shuffling, using, for example, phage display technology, and a polypeptide comprising a heavy or light chain variable domain of a non-human antibody specific for an antigen of interest is combined with a repertoire of human complementary (light or heavy) chain variable domains. Hybrid pairings that are specific for the antigen of interest are identified and human chains from the selected pairings are combined with a repertoire of human complementary variable domains (heavy or light). In another embodiment, a component of a CDR from a non-human antibody is combined with a repertoire of component parts of CDRs from human antibodies. From the resulting library of antibody polypeptide dimers, hybrids are selected and used in a second humanizing shuffling step. Alternatively, this second step is eliminated if the hybrid is already of sufficient human character to be of therapeutic value. Methods of modification to increase human character are also described. See also Winter, *FEBS Letts* 430:92-92 (1998).

As another example, U.S. Pat. No. 6,054,297 to Carter et al., issued Apr. 25, 2000 describes a method for making humanized antibodies by substituting a CDR amino acid sequence for the corresponding human CDR amino acid sequence and/or substituting a FR amino acid sequence for the corresponding human FR amino acid sequences.

As another example, U.S. Pat. No. 5,766,886 to Studnicka et al., issued Jun. 16, 1998 ("Modified antibody variable domains") describes methods for identifying the amino acid residues of an antibody variable domain which may be modified without diminishing the native affinity of the antigen binding domain while reducing its immunogenicity with respect to a heterologous species and methods for preparing these modified antibody variable domains which are useful for administration to heterologous species. See also U.S. Pat. No. 5,869,619 to Studnicka issued Feb. 9, 1999.

As discussed, modification of an antibody by any of the methods known in the art is typically designed to achieve increased binding affinity for an antigen and/or reduce immunogenicity of the antibody in the recipient. In one approach, humanized antibodies can be modified to eliminate glycosylation sites in order to increase affinity of the antibody for its cognate antigen [Co et al., *Mol Immunol* 30:1361-1367 (1993)]. Techniques such as "reshaping," "hyperchimerization," and "veneering/resurfacing" have produced humanized antibodies with greater therapeutic potential. [Vaswami et al., *Annals of Allergy, Asthma, & Immunol* 81:105 (1998); Roguska et al., *Prot Engineer* 9:895-904 (1996)]. See also U.S. Pat. No. 6,072,035 to Hardman et al., issued Jun. 6, 2000, which describes methods for reshaping antibodies. While these techniques diminish antibody immunogenicity by reducing the number of foreign residues, they do not prevent anti-idiotypic and anti-allotypic responses following repeated administration of the antibodies. Alternatives to these methods for reducing immunogenicity are described in Gilliland et al., *J Immunol* 62(6): 3663-71 (1999).

In many instances, humanizing antibodies results in a loss of antigen binding capacity. It is therefore preferable to "back mutate" the humanized antibody to include one or more of the amino acid residues found in the original (most often rodent) antibody in an attempt to restore binding affinity of the antibody. See, for example, Saldanha et al., *Mol Immunol* 36:709-19 (1999).

Non-Peptide Specific Binding Agent Analogs/Protein Mimetics

Furthermore, nonpeptide specific binding agent analogs of peptides that provide a stabilized structure or lessened biodegradation, are also contemplated. Specific binding agent peptide mimetic analogs can be prepared based on a selected inhibitory peptide by replacement of one or more residues by nonpeptide moieties. Preferably, the nonpeptide moieties permit the peptide to retain its natural confirmation, or stabilize a preferred, e.g., bioactive, confirmation which retains the ability to recognize and bind Ang-2. In one aspect, the resulting analog/mimetic exhibits increased binding affinity for Ang-2. One example of methods for preparation of nonpeptide mimetic analogs from specific binding agent peptides is described in Nachman et al., *Regul Pept* 57:359-370 (1995). If desired, the specific binding agent peptides of the invention can be modified, for instance, by glycosylation, amidation, carboxylation, or phosphorylation, or by the creation of acid addition salts, amides, esters, in particular C-terminal esters, and N-acyl derivatives of the peptides of the invention. The specific binding agent peptides also can be modified to create peptide derivatives by forming covalent or noncovalent complexes with other moieties. Covalently-bound complexes can be prepared by linking the chemical moieties to functional groups on the side chains of amino acids comprising the specific binding agent peptides, or at the N- or C-terminus.

In particular, it is anticipated that the specific binding agent peptides can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). The invention accordingly provides a molecule comprising an antibody molecule, wherein the molecule preferably further comprises a reporter group selected from the group consisting of a radiolabel, a fluorescent label, an enzyme, a substrate, a solid matrix, and a carrier. Such labels are well known to those of skill in the art, e.g., biotin labels are particularly contemplated. The use of such labels is well known to those of skill in the art and is described in, e.g., U.S. Pat. Nos. 3,817, 837; 3,850,752; 3,996,345 and 4,277,437. Other labels that will be useful include but are not limited to radioactive labels, fluorescent labels and chemiluminescent labels. U.S. Patents concerning use of such labels include for example U.S. Pat. Nos. 3,817,837; 3,850,752; 3,939,350 and 3,996,345. Any of the peptides of the present invention may comprise one, two, or more of any of these labels.

Methods of Making Specific Binding Agents

Specific binding agents of the present invention that are proteins can be prepared by chemical synthesis in solution or on a solid support in accordance with conventional techniques. The current limit for solid phase synthesis is about 85-100 amino acids in length. However, chemical synthesis techniques can often be used to chemically ligate a series of smaller peptides to generate full length polypeptides. Various automatic synthesizers are commercially available and can be used in accordance with known protocols. See, for example, Stewart and Young, Solid Phase Peptide Synthesis, 2d. ed., Pierce Chemical Co., (1984); Tam et al., *J Am Chem Soc*, 105:6442, (1983); Merrifield, Science, 232:341-347, (1986); and Barany and Merrifield, The Peptides, Gross and Meienhofer, eds, Academic Press, New York, 1-284; Barany et al., Int. J. Peptide Protein Res., 30, 705-739 (1987); and U.S. Pat. No. 5,424,398), each incorporated herein by reference.

Solid phase peptide synthesis methods use a copoly(styrene-divinylbenzene) containing 0.1-1.0 mM amines/g polymer. These methods for peptide synthesis use butyloxycarbonyl (t-BOC) or 9-fluorenylmethyloxy-carbonyl (FMOC) protection of alpha-amino groups. Both methods involve stepwise syntheses whereby a single amino acid is added at each step starting from the C-terminus of the peptide (See, Coligan et al., Current Protocols in Immunology, Wiley Interscience, 1991, Unit 9). On completion of chemical synthesis, the synthetic peptide can be deprotected to remove the t-BOC or FMOC amino acid blocking groups and cleaved from the polymer by treatment with acid at reduced temperature (e.g., liquid HF-10% anisole for about 0.25 to about 1 hours at 0° C.). After evaporation of the reagents, the specific binding agent peptides are extracted from the polymer with 1% acetic acid solution that is then lyophilized to yield the crude material. This can normally be purified by such techniques as gel filtration on Sephadex G-15 using 5% acetic acid as a solvent. Lyophilization of appropriate fractions of the column will yield the homogeneous specific binding agent peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Chemical synthesis of anti-Ang-2 antibodies, derivatives, variants, and fragments thereof, as well as other protein-based Ang-2 binding agents permits incorporation of non-naturally occurring amino acids into the agent.

Recombinant DNA techniques are a convenient method for preparing full length antibodies and other large proteinaceous specific binding agents of the present invention, or fragments thereof. A cDNA molecule encoding the antibody or fragment may be inserted into an expression vector, which can in turn be inserted into a host cell for production of the antibody or fragment. It is understood that the cDNAs encoding such antibodies may be modified to vary from the "original" cDNA (translated from the mRNA) to provide for codon degeneracy or to permit codon preference usage in various host cells.

Generally, a DNA molecule encoding an antibody can be obtained using procedures described herein in the Examples. Where it is desirable to obtain Fab molecules or CDRs that are related to the original antibody molecule, one can screen a suitable library (phage display library; lymphocyte library, etc.) using standard techniques to identify and clone related Fabs/CDRs. Probes used for such screening may be full length or truncated Fab probes encoding the Fab portion of the original antibody, probes against one or more CDRs from the Fab portion of the original antibody, or other suitable probes. Where DNA fragments are used as probes, typical hybridization conditions are those such as set forth in Ausubel et. al. (Current Protocols in Molecular Biology, Current Protocols Press [1994]). After hybridization, the probed blot can be washed at a suitable stringency, depending on such factors as probe size, expected homology of probe to clone, the type of library being screened, and the number of clones being screened. Examples of high stringency screening are 0.1× SSC, and 0.1 percent SDS at a temperature between 50-65° C.

A variety of expression vector/host systems may be utilized to contain and express the polynucleotide molecules encoding the specific binding agent polypeptides of the invention. These systems include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems.

Mammalian cells that are useful in recombinant specific binding agent protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells, as well as hybridoma cell lines as described herein. Mammalian cells are preferred for preparation of those specific binding agents such as antibodies and antibody fragments that are typically glycosylated and require proper refolding for activity. Preferred mammalian cells include CHO cells, hybridoma cells, and myeloid cells.

Some exemplary protocols for the recombinant expression of the specific binding agent proteins are described herein below.

The term "expression vector" refers to a plasmid, phage, virus or vector, for expressing a polypeptide from a DNA (RNA) sequence. An expression vector can comprise a transcriptional unit comprising an assembly of (1) a genetic element or elements having a regulatory role in gene expression, for example, promoters or enhancers, (2) a structural or sequence that encodes the binding agent which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant specific binding agent protein is expressed without a leader or transport sequence, it may include an amino terminal methionine residue. This residue may or may not be subsequently cleaved from the expressed recombinant protein to provide a final specific binding agent product.

For example, the specific binding agents may be recombinantly expressed in yeast using a commercially available expression system, e.g., the Pichia Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol.

The secreted specific binding agent peptide is purified from the yeast growth medium by, e.g., the methods used to purify the peptide from bacterial and mammalian cell supernatants.

Alternatively, the cDNA encoding the specific binding agent peptide may be cloned into the baculovirus expression vector pVL1393 (PharMingen, San Diego, Calif.). This vector can be used according to the manufacturer's directions (PharMingen) to infect Spodoptera frugiperda cells in sF9 protein-free media and to produce recombinant protein. The specific binding agent protein can be purified and concentrated from the media using a heparin-Sepharose column (Pharmacia).

Alternatively, the peptide may be expressed in an insect system. Insect systems for protein expression are well known to those of skill in the art. In one such system, Autographa californica nuclear polyhedrosis virus (AcNPV) can be used as a vector to express foreign genes in Spodoptera frugiperda cells or in Trichoplusia larvae. The specific binding agent peptide coding sequence can be cloned into a nonessential region of the virus, such as the polyhedrin gene, and placed under control of the polyhedrin promoter. Successful insertion of the specific binding agent peptide will render the polyhedrin gene inactive and produce recombinant virus lacking coat protein coat. The recombinant viruses can be used to infect S. frugiperda cells or Trichoplusia larvae in which peptide is expressed [Smith et al., J Virol 46: 584 (1983); Engelhard et al., Proc Nat Acad Sci (USA) 91: 3224-7 (1994)].

In another example, the DNA sequence encoding the specific binding agent peptide can be amplified by PCR and cloned into an appropriate vector for example, pGEX-3× (Pharmacia). The pGEX vector is designed to produce a fusion protein comprising glutathione-S-transferase (GST), encoded by the vector, and a specific binding agent protein encoded by a DNA fragment inserted into the vector's cloning site. The primers for the PCR can be generated to include for example, an appropriate cleavage site. Where the specific binding agent fusion moiety is used solely to facilitate expression or is otherwise not desirable as an attachment to the peptide of interest, the recombinant specific binding agent fusion protein may then be cleaved from the GST portion of the fusion protein. The pGEX-3×/specific binding agent peptide construct is transformed into E. coli XL-1 Blue cells (Stratagene, La Jolla Calif.), and individual transformants isolated and grown. Plasmid DNA from individual transformants can be purified and partially sequenced using an automated sequencer to confirm the presence of the desired specific binding agent encoding nucleic acid insert in the proper orientation.

Expression of polynucleotides encoding anti-Ang-2 antibodies and fragments thereof using the recombinant systems described above may result in production of antibodies or fragments thereof that must be "re-folded" (to properly create various disulphide bridges) in order to be biologically active. Typical refolding procedures for such antibodies are set forth in the Examples herein and in the following section.

Specific binding agents made in bacterial cells may be produced as an insoluble inclusion body in the bacteria, can be purified as follows. Host cells can be sacrificed by centrifugation; washed in 0.15 M NaCl, 10 mM Tris, pH 8, 1 mM EDTA; and treated with 0.1 mg/ml lysozyme (Sigma, St. Louis, Mo.) for 15 minutes at room temperature. The lysate can be cleared by sonication, and cell debris can be pelleted by centrifugation for 10 minutes at 12,000×g. The specific binding agent-containing pellet can be resuspended in 50 mM Tris, pH 8, and 10 mM EDTA, layered over 50% glycerol, and centrifuged for 30 min. at 6000×g. The pellet can be resuspended in standard phosphate buffered saline solution (PBS) free of $Mg^{++}$ and $Ca^{++}$. The specific binding agent can be further purified by fractionating the resuspended pellet in a denaturing SDS polyacrylamide gel (Sambrook et al., supra). The gel can be soaked in 0.4 M KCl to visualize the protein, which can be excised and electroeluted in gel-running buffer lacking SDS. If the GST fusion protein is produced in bacteria, as a soluble protein, it can be purified using the GST Purification Module (Pharmacia).

Mammalian host systems for the expression of the recombinant protein are well known to those of skill in the art. Host cell strains can be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Different host cells such as CHO, HeLa, MDCK, 293, W138, as well as hybridoma cell lines, and the like have specific cellular machinery and characteristic mechanisms for such post-translational activities and can be chosen to ensure the correct modification and processing of the introduced, foreign protein.

A number of selection systems can be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for DHFR which confers resistance to methotrexate; gpt which confers resistance to mycophenolic acid; neo which confers resistance to the aminoglycoside G418 and confers resistance to chlorsulfuron; and hygro which that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, β-glucuronidase and its substrate, GUS, and luciferase and its substrate, luciferin.

Purification and Refolding of Specific Binding Agents

In some cases, the specific binding agents produced using procedures described above may need to be "refolded" and oxidized into a proper tertiary structure and generating disulfide linkages in order to be biologically active. Refolding can be accomplished using a number of procedures well known in the art. Such methods include, for example, exposing the solubilized polypeptide agent to a pH usually above 7 in the presence of a chaotropic agent. The selection of chaotrope is similar to the choices used for inclusion body solubilization, however a chaotrope is typically used at a lower concentration. An exemplary chaotropic agent is guanidine. In most cases, the refolding/oxidation solution will also contain a reducing agent plus its oxidized form in a specific ratio to generate a particular redox potential which allows for dusykfide shuffling to occur for the formation of cysteine bridges. Some commonly used redox couples include cysteine/cystamine, glutathione/dithiobisGSH, cupric chloride, dithiothreitol DTT/dithiane DTT, and 2-mercaptoethanol (bME)/dithio-bME. In many instances, a co-solvent may be used to increase the efficiency of the refolding. Commonly used cosolvents include glycerol, polyethylene glycol of various molecular weights, and arginine.

It will be desirable to purify specific binding agent proteins or variants thereof of the present invention. Protein purification techniques are well known to those of skill in the art. These techniques involve, at one level, the crude fractionation of the polypeptide and non-polypeptide fractions. Having separated the specific binding agent polypeptide from other proteins, the polypeptide of interest can be further purified using chromatographic and electrophoretic techniques to achieve partial or complete purification (or purification to homogeneity). Analytical methods particularly suited to the preparation of a pure specific binding agent peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded specific binding agent protein or peptide. The term "purified specific binding agent protein or peptide" as used herein, is intended to refer to a composition, isolatable from other components, wherein the specific binding agent protein or peptide is purified to any degree relative to its naturally-obtainable state. A purified specific binding agent protein or peptide therefore also refers to a specific binding agent protein or peptide, free from the environment in which it may naturally occur.

Generally, "purified" will refer to a specific binding agent composition that has been subjected to fractionation to remove various other components, and which composition substantially retains its expressed biological activity. Where the term "substantially purified" is used, this designation will refer to a specific binding agent composition in which the specific binding agent protein or peptide forms the major component of the composition, such as constituting about 50%, about 60%, about 70%, about 80%, about 90%, about 95% or more of the proteins in the composition.

Various methods for quantifying the degree of purification of the specific binding agent will be known to those of skill in the art in light of the present disclosure. These include, for example, determining the specific binding activity of an active fraction, or assessing the amount of specific binding agent polypeptides within a fraction by SDS/PAGE analysis. A preferred method for assessing the purity of a specific binding agent fraction is to calculate the binding activity of the fraction, to compare it to the binding activity of the initial extract, and to thus calculate the degree of purification, herein assessed by a "-fold purification number." The actual units used to represent the amount of binding activity will, of course, be dependent upon the particular assay technique chosen to follow the purification and whether or not the expressed specific binding agent protein or peptide exhibits a detectable binding activity.

Various techniques suitable for use in specific binding agent protein purification will be well known to those of skill in the art. These include, for example, precipitation with ammonium sulphate, PEG, antibodies (immunoprecipitation) and the like or by heat denaturation, followed by centrifugation; chromatography steps such as affinity chromatography (e.g., Protein-A-Sepharose), ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified specific binding agent.

There is no general requirement that the specific binding agent always be provided in its most purified state. Indeed, it is contemplated that less substantially specific binding agent products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low-pressure chromatography system. Methods exhibiting a lower degree of relative purification may have advantages in total recovery of specific binding agent protein product, or in maintaining binding activity of an expressed specific binding agent protein.

It is known that the migration of a polypeptide can vary, sometimes significantly, with different conditions of SDS/PAGE [Capaldi et al., *Biochem Biophys\Res Comm,* 76: 425 (1977)]. It will therefore be appreciated that under differing electrophoresis conditions, the apparent molecular weights of purified or partially purified specific binding agent expression products may vary.

Binding Assays

Immunological binding assays typically utilize a capture agent to bind specifically to and often immobilize the analyte target antigen. The capture agent is a moiety that specifically binds to the analyte. In one embodiment of the present invention, the capture agent is an antibody or fragment thereof that specifically binds Ang-2. These immunological binding assays are well known in the art [see, Asai, ed., Methods in Cell Biology, Vol. 37, Antibodies in Cell Biology, Academic Press, Inc., New York (1993)].

Immunological binding assays frequently utilize a labeling agent that will signal the existence of the bound complex formed by the capture agent and antigen. The labeling agent can be one of the molecules comprising the bound complex; i.e. it can be labeled specific binding agent or a labeled anti-specific binding agent antibody. Alternatively, the labeling agent can be a third molecule, commonly another antibody, which binds to the bound complex. The labeling agent can be, for example, an anti-specific binding agent antibody bearing a label. The second antibody, specific for the bound complex, may lack a label, but can be bound by a fourth molecule specific to the species of antibodies which the second antibody is a member of. For example, the second antibody can be modified with a detectable moiety, such as biotin, which can then be bound by a fourth molecule, such as enzyme-labeled streptavidin. Other proteins capable of specifically binding immunoglobulin constant regions, such as protein A or protein G may also be used as the labeling agent. These binding proteins are normal constituents of the cell walls of streptococcal bacteria and exhibit a strong non-immunogenic reactivity with immunoglobulin constant regions from a variety of species [see, generally Akerstrom, *J Immunol,* 135:2589-2542 (1985); and Chaubert, *Mod Pathol,* 10:585-591 (1997)].

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures.

A. Non-competitive Binding Assays:

Immunological binding assays can be of the non-competitive type. These assays have an amount of captured analyte that is directly measured. For example, in one preferred "sandwich" assay, the capture agent (antibody) can be bound directly to a solid substrate where it is immobilized. These immobilized antibodies then capture (bind to) antigen present in the test sample. The protein thus immobilized is then bound to a labeling agent, such as a second antibody having a label. In another preferred "sandwich" assay, the second antibody lacks a label, but can be bound by a labeled antibody specific for antibodies of the species from which the second antibody is derived. The second antibody also can be modified with a detectable moiety, such as biotin, to which a third labeled molecule can specifically bind, such as streptavidin. [See, Harlow and Lane, Antibodies, A Laboratory Manual, Ch 14, Cold Spring Harbor Laboratory, NY (1988), incorporated herein by reference].

B. Competitive Binding Assays:

Immunological binding assays can be of the competitive type. The amount of analyte present in the sample is measure indirectly by measuring the amount of an added analyte displaced, or competed away, from a capture agent by the analyte present in the sample. In one preferred competitive binding assay, a known amount of analyte, usually labeled, is added to the sample and the sample is then contacted with an antibody (the capture agent). The amount of labeled analyze bound to the antibody is inversely proportional to the concentration of analyte present in the sample. (See, Harlow and Lane, Antibodies, A Laboratory Manual, Ch 14, pp. 579-583, supra).

In another preferred competitive binding assay, the antibody is immobilized on a solid substrate. The amount of protein bound to the antibody may be determined either by measuring the amount of protein present in a protein/antibody complex, or alternatively by measuring the amount of remaining uncomplexed protein. The amount of protein may be detected by providing a labeled protein. See, Harlow and Lane, Antibodies, A Laboratory Manual, Ch 14, supra).

Yet another preferred competitive binding assay, hapten inhibition is utilized. Here, a known analyte is immobilized on a solid substrate. A known amount of antibody is added to the sample, and the sample is contacted with the immobilized analyte. The amount of antibody bound to the immobilized analyte is inversely proportional to the amount of analyte present in the sample. The amount of immobilized antibody may be detected by detecting either the immobilized fraction of antibody or the fraction that remains in solution. Detection may be direct where the antibody is labeled or indirect by the subsequent addition of a labeled moiety that specifically binds to the antibody as described above.

C. Utilization of Competitive Binding Assays:

The competitive binding assays can be used for cross-reactivity determinations to permit a skilled artisan to determine if a protein or enzyme complex which is recognized by a specific binding agent of the invention is the desired protein and not a cross-reacting molecule or to determine whether the antibody to is specific for the antigen and does not bind unrelated antigens. In assays of this type, antigen can be immobilized to a solid support and an unknown protein mixture is added to the assay, which will compete with the binding of the specific binding agents to the immobilized protein. The competing molecule also binds one or more antigens unrelated to the antigen. The ability of the proteins to compete with the binding of the specific binding agents antibodies to the immobilized antigen is compared to the binding by the same protein that was immobilized to the solid support to determine the cross-reactivity of the protein mix.

D. Other Binding Assays:

The present invention also provides Western blot methods to detect or quantify the presence of Ang-2 in a sample. The technique generally comprises separating sample proteins by gel electrophoresis on the basis of molecular weight and transferring the proteins to a suitable solid support, such as nitrocellulose filter, a nylon filter, or derivatized nylon filter. The sample is incubated with antibodies or fragments thereof that specifically bind Ang-2 and the resulting complex is detected. These antibodies may be directly labeled or alternatively may be subsequently detected using labeled antibodies that specifically bind to the antibody.

Binding assays to detect those Ang-2 specific binding agents that disrupt Ang-2 binding to its receptor are set forth in the Examples herein.

Diagnostic Assays

The antibodies or fragments thereof of present invention are useful for the diagnosis of conditions or diseases characterized by expression of Ang-2 or subunits, or in assays to monitor patients being treated with inducers of Ang-2, its fragments, agonists or inhibitors of Ang-2 activity. Diagnostic assays for Ang-2 include methods utilizing a specific binding agent and a label to detect Ang-2 in human body fluids or extracts of cells or tissues. The specific binding agents of the present invention can be used with or without modification. In a preferred diagnostic assay, the specific binding agents will be labeled by attaching, e.g., a label or a reporter molecule. A wide variety of labels and reporter molecules are known, some of which have been already described herein. In particular, the present invention is useful for diagnosis of human disease.

A variety of protocols for measuring Ang-2 proteins using either polyclonal or monoclonal antibodies specific for the respective protein are known in the art. Examples include enzyme-linked immunosorbent assay (ELISA), radioimmunoassay (RIA) and fluorescence activated cell sorting (FACS). A two-site, monoclonal-based immunoassay utilizing monoclonal antibodies reactive to two non-interfering epitopes on Ang-2 is preferred, but a competitive binding assay can be employed. These assays are described, for example, in Maddox et al., *J Exp Med,* 158:1211 [1983].

In order to provide a basis for diagnosis, normal or standard values for human Ang-2 expression are usually established. This determination can be accomplished by combining body fluids or cell extracts from normal subjects, preferably human, with a specific binding agent, for example, an antibody, to Ang-2, under conditions suitable for complex formation that are well known in the art. The amount of standard complex formation can be quantified by comparing the binding of the specific binding agents to known quantities of Ang-2 protein, with both control and disease samples. Then, standard values obtained from normal samples can be compared with values obtained from samples from subjects potentially affected by disease. Deviation between standard and subject values suggests a role for Ang-2 in the disease state.

For diagnostic applications, in certain embodiments, specific binding agents typically will be labeled with a detectable moiety. The detectable moiety can be any one that is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; or an enzyme, such as alkaline phosphatase, β-galactosidase, or horseradish peroxidase [Bayer et al., *Meth Enz,* 184: 138-163, (1990)].

Diseases

The present invention provides a specific binding agent that binds to Ang-2 that is useful for the treatment of human diseases and pathological conditions. Agents that modulate Ang-2 binding activity, or other cellular activity, may be used in combination with other therapeutic agents to enhance their therapeutic effects or decrease potential side effects.

In one aspect, the present invention provides reagents and methods useful for treating diseases and conditions characterized by undesirable or aberrant levels of Ang-2 activity in a cell. These diseases include cancers, and other hyperproliferative conditions, such as hyperplasia, psoriasis, contact dermatitis, immunological disorders, and infertility.

The present invention also provides methods of treating cancer in an animal, including humans, comprising administering to the animal an effective amount of a specific binding agent that inhibits or decreases Ang-2 activity. The invention is further directed to methods of inhibiting cancer cell growth, including processes of cellular proliferation, invasiveness, and metastasis in biological systems. Methods include use of a compound of the invention as an inhibitor of cancer cell growth. Preferably, the methods are employed to inhibit or reduce cancer cell growth, invasiveness, metastasis, or tumor incidence in living animals, such as mammals. Methods of the invention are also readily adaptable for use in assay systems, e.g., assaying cancer cell growth and properties thereof, as well as identifying compounds that affect cancer cell growth.

The cancers treatable by methods of the present invention preferably occur in mammals. Mammals include, for example, humans and other primates, as well as pet or companion animals such as dogs and cats, laboratory animals such as rats, mice and rabbits, and farm animals such as horses, pigs, sheep, and cattle.

Tumors or neoplasms include growths of tissue cells in which the multiplication of the cells is uncontrolled and progressive. Some such growths are benign, but others are termed malignant and may lead to death of the organism. Malignant neoplasms or cancers are distinguished from benign growths in that, in addition to exhibiting aggressive cellular proliferation, they may invade surrounding tissues and metastasize. Moreover, malignant neoplasms are characterized in that they show a greater loss of differentiation (greater dedifferentiation), and of their organization relative to one another and their surrounding tissues. This property is also called "anaplasia."

Neoplasms treatable by the present invention also include solid tumors, i.e., carcinomas and sarcomas. Carcinomas include those malignant neoplasms derived from epithelial cells that infiltrate (invade) the surrounding tissues and give rise to metastases. Adenocarcinomas are carcinomas derived from glandular tissue, or which form recognizable glandular structures. Another broad category or cancers includes sarcomas, which are tumors whose cells are embedded in a fibrillar or homogeneous substance like embryonic connective tissue. The invention also enables treatment of cancers of the myeloid or lymphoid systems, including leukemias, lymphomas and other cancers that typically do not present as a tumor mass, but are distributed in the vascular or lymphoreticular systems.

The type of cancer or tumor cells amenable to treatment according to the invention include, for example, ACTH-producing tumor, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and non-small cell), malignant peritoneal effusion, malignant pleural effusion, melanoma, mesothelioma, multiple myeloma, neuroblastoma, glioma, non-Hodgkin's lymphoma, osteosarcoma, ovarian cancer, ovarian (germ cell) cancer, pancreatic cancer, penile cancer, prostate cancer, retinoblastoma, skin cancer, soft tissue sarcoma, squamous cell carcinomas, stomach cancer, testicular cancer, thyroid cancer, trophoblastic neoplasms, uterine cancer, vaginal cancer, cancer of the vulva, and Wilms' tumor.

The invention is particularly illustrated herein in reference to treatment of certain types of experimentally defined cancers. In these illustrative treatments, standard state-of-the-art in vitro and in vivo models have been used. These methods can be used to identify agents that can be expected to be efficacious in in vivo treatment regimens. However, it will be understood that the method of the invention is not limited to the treatment of these tumor types, but extends to any solid tumor derived from any organ system. Cancers whose invasiveness or metastasis is associated with Ang-2 expression or activity are especially susceptible to being inhibited or even induced to regress by means of the invention.

The invention can also be practiced by including with a specific binding agent of the invention, such as an antibody, in combination with another anti-cancer chemotherapeutic agent, such as any conventional chemotherapeutic agent. The combination of a specific binding agent with such other agents can potentiate the chemotherapeutic protocol. Numerous chemotherapeutic protocols will present themselves in the mind of the skilled practitioner as being capable of incorporation into the method of the invention. Any chemotherapeutic agent can be used, including alkylating agents, antimetabolites, hormones and antagonists, radioisotopes, as well as natural products. For example, the compound of the invention can be administered with antibiotics such as doxorubicin and other anthracycline analogs, nitrogen mustards such as cyclophosphamide, pyrimidine analogs such as 5-fluorouracil, cisplatin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of a tetracycline compound with another treatment modality, e.g., surgery, radiation, etc., also referred to herein as "adjunct antineoplastic modalities." Thus, the method of the invention can be employed with such conventional regimens with the benefit of reducing side effects and enhancing efficacy.

The present invention thus provides compositions and methods useful for the treatment of a wide variety of cancers, including solid tumors and leukemias. Types of cancer that may be treated include, but are not limited to: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell); histiocytic disorders; leukemia; histiocytosis malignant; Hodgkin's disease; immunoproliferative small lung cell carcinoma; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; tophoblastic tumor. Further, the following types of cancers may also be treated: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; Sertoli cell tumor; theca cell tumor; leiomyoma; leiomyosarcoma; myoblastoma; myoma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin; angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Another aspect of the present invention is using the materials and methods of the present invention to prevent and/or treat any hyperproliferative condition of the skin including psoriasis and contact dermatitis or other hyperproliferative diseases. It has been demonstrated that patients with psoriasis and contact dermatitis have elevated Ang-2 activity within these lesions [Ogoshi et al., *J. Inv. Dermatol.*, 110:818-23 (1998)]. Preferably, specific binding agents specific for Ang-2 will be used in combination with other pharmaceutical agents to treat humans that express these clinical symptoms. The specific binding agents can be delivered using any of the various carriers through routes of administration described herein and others that are well known to those of skill in the art.

Other aspects of the present invention include treating various retinopathies (including diabetic retinopathy and age-related macular degeneration) in which angiogenesis is involved, as well as disorders/diseases of the female reproductive tract such as endometriosis, uterine fibroids, and other such conditions associated with dysfunctional vascular proliferation (including endometrial microvascular growth) during the female reproductive cycle.

Still another aspect of the present invention relates to treating abnormal vascular growth including cerebral arteriovenous malformations (AVMs) gastrointestinal mucosal injury and repair, ulceration of the gastroduodenal mucosa in patients with a history of peptic ulcer disease, including ischemia resulting from stroke, a wide spectrum of pulmonary vascular disorders in liver disease and portal hypertension in patients with nonhepatic portal hypertension.

Another aspect of present invention is the prevention of cancers utilizing the compositions and methods provided by the present invention. Such reagents will include specific binding agents against Ang-2.

Pharmaceutical Compositions

Pharmaceutical compositions of Ang-2 specific binding agents are within the scope of the present invention. Pharmaceutical compositions comprising antibodies are described in detail in, for example, U.S. Pat. No. 6,171,586, to Lam et al., issued Jan. 9, 2001. Such compositions comprise a therapeutically or prophylactically effective amount of a specific binding agent, such as an antibody, or a fragment, variant, derivative or fusion thereof as described herein, in admixture with a pharmaceutically acceptable agent. In a preferred embodiment, pharmaceutical compositions comprise antagonist specific binding agents that modulate partially or completely at least one biological activity of Ang-2 in admixture with a pharmaceutically acceptable agent. Typically, the specific binding agents will be sufficiently purified for administration to an animal.

The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents [such as ethylenediamine tetraacetic acid (EDTA)]; complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company, 1990).

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the specific binding agent.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefore. In one embodiment of the present invention, binding agent compositions may be prepared for storage by mixing the selected composition having the desired degree of purity with optional formulation agents (Remington's Pharmaceutical Sciences, supra) in the form of a lyophilized cake or an aqueous solution. Further, the binding agent product may be formulated as a lyophilizate using appropriate excipients such as sucrose.

The pharmaceutical compositions can be selected for parenteral delivery. Alternatively, the compositions may be selected for inhalation or for enteral delivery such as orally, aurally, opthalmically, rectally, or vaginally. The preparation of such pharmaceutically acceptable compositions is within the skill of the art.

The formulation components are present in concentrations that are acceptable to the site of administration. For example, buffers are used to maintain the composition at physiological pH or at slightly lower pH, typically within a pH range of from about 5 to about 8.

When parenteral administration is contemplated, the therapeutic compositions for use in this invention may be in the form of a pyrogen-free, parenterally acceptable aqueous solution comprising the desired specific binding agent in a pharmaceutically acceptable vehicle. A particularly suitable vehicle for parenteral Injection is sterile distilled water in which a binding agent is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for parenteral administration may be formulated in aqueous solutions, preferably in physiologically compatible buffers such as Hanks' solution, ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

In another embodiment, a pharmaceutical composition may be formulated for inhalation. For example, a binding agent may be formulated as a dry powder for inhalation. Polypeptide or nucleic acid molecule inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins.

It is also contemplated that certain formulations may be administered orally. In one embodiment of the present invention, binding agent molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the binding agent molecule. Diluents, flavorings, low melting point waxes, vegetable oils, lubricants, suspending agents, tablet disintegrating agents, and binders may also be employed.

Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Another pharmaceutical composition may involve an effective quantity of binding agent in a mixture with non-toxic excipients that are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving binding agent molecules in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate [Sidman et al., *Biopolymers,* 22:547-556 (1983)], poly (2-hydroxyethyl-methacrylate) [Langer et al., *J Biomed Mater Res,* 15:167-277, (1981)] and [Langer et al., *Chem Tech,* 12:98-105(1982)], ethylene vinyl acetate (Langer et al., supra) or poly-D(−)-3-hydroxybutyric acid (EP 133,988). Sustained-release compositions also include liposomes, which can be prepared by any of several methods known in the art. See e.g., Eppstein et al., *Proc Natl Acad Sci (USA),* 82:3688-3692 (1985); EP 36,676; EP 88,046; EP 143,949.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding agent molecule is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. In other embodiments, the dosage may range from 0.1 mg/kg up to about 100 mg/kg; or 1 mg/kg up to about 100 mg/kg; or 5 mg/kg up to about 100 mg/kg.

For any compound, the therapeutically effective dose can be estimated initially either in cell culture assays or in animal models such as mice, rats, rabbits, dogs, or pigs. An animal model may also be used to determine the appropriate concentration range and route of administration. Such information can then be used to determine useful doses and routes for administration in humans.

The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

The frequency of dosing will depend upon the pharmacokinetic parameters of the binding agent molecule in the formulation used. Typically, a composition is administered until a dosage is reached that achieves the desired effect. The composition may therefore be administered as a single dose, or as multiple doses (at the same or different concentrations/ dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intracerebral (intraparenchymal), intracerebroventricular, intramuscular, intraocular, intraarterial, intraportal, intralesional routes, intramedullary, intrathecal, intraventricular, transdermal, subcutaneous, intraperitoneal, intranasal, enteral, topical, sublingual, urethral, vaginal, or rectal means, by sustained release systems or by implantation devices. Where desired, the compositions may be administered by bolus injection or continuously by infusion, or by implantation device.

Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use pharmaceutical compositions in an ex vivo manner. In such instances, cells, tissues, or organs that have been removed from the patient are exposed to the pharmaceutical compositions after which the cells, tissues and/or organs are subsequently implanted back into the patient.

In other cases, a binding agent which is a polypeptide can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Combination Therapy

Specific binding agents of the invention can be utilized in combination with other therapeutic in the treatment of Ang-2 pathologies. These other therapeutics include, for example radiation treatment, chemotherapeutic agents, as well as other growth factors.

Chemotherapy treatment can employ anti-neoplastic agents including, for example, alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; ppipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinium coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

Combination therapy with growth factors can include cytokines, lymphokines, growth factors, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNF0, TNF1, TNF2, G-CSF, Meg-CSF, GM-CSF, thrombopoietin, stem cell factor, and erythropoietin. Other are compositions can include known angiopoietins, for example Ang-1, -2, -4, -Y, and/or the human Ang-like polypeptide, and/or vascular endothelial growth factor (VEGF). Growth factors include angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-1, bone morphogenic protein-12, bone morphogenic protein-13, bone morphogenic protein-14, bone morphogenic protein-15, bone morphogenic protein receptor-IA, bone morphogenic protein receptor IB, brain derived neurotrophic factor, ciliary neutrophic factor, ciliary neutrophic factor receptor, cytokine-induced neutrophil chemotactic factor-1, cytokine-induced neutrophil, chemotactic factor-2, cytokine-induced neutrophil chemotactic factor-2, endothelial cell growth factor, endothelin-1, epidermal growth factor, epithelial-derived neutrophil attractant, fibroblast growth factor-4, fibroblast growth factor-5, fibroblast growth factor-6, fibroblast growth factor-7, fibroblast growth factor-8, fibroblast growth factor-8b, fibroblast growth factor-8c, fibroblast growth factor-9, fibroblast growth factor-10, fibroblast growth factor acidic, fibroblast growth factor basic, glial cell line-derived neutrophic factor receptor-1, glial cell line-derived neutrophic factor receptor-2, growth related protein, growth related protein-2, growth related protein-2, growth related protein-3, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor-1, nerve growth factor nerve growth factor receptor, neurotrophin-3, neurotrophin-4, placenta growth factor, placenta growth factor-2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor-1, platelet derived growth factor receptor-2, pre-B cell growth stimulating factor, stem cell factor, stem cell factor receptor, transforming growth factor-1, transforming growth factor-2, transforming growth factor-3, transforming growth factor-1.2, transforming growth factor-4, transforming growth facotr-5, latent transforming growth factor-1, transforming growth factor binding protein I, transforming growth factor binding protein II, transforming growth factor binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

Immunotherapeutics

Immunotherapeutics generally rely on the use of immune effector cells and molecules to target and destroy cancer cells. The immune effectors may be, for example an antibody of the present invention that recognizes some marker on the surface of a target cell. The antibody alone may serve as an effector of therapy or it may recruit other cells to actually effect cell killing. The antibody may also be conjugated to a drug or toxin (chemotherapeutic, radionuclide, ricin A chain, cholera toxin, pertussis toxin, etc.) and thus may merely serve as a targeting agent.

According to the present invention, mutant forms of Ang-2 may be targeted by immunotherapy either antibodies or antibody conjugates of the invention. It is particularly contemplated that the antibody compositions of the invention may be used in a combined therapy approach in conjunction with Ang-2 targeted therapy.

Passive immunotherapy has proved to be particularly effective against a number of cancers. See, for example, WO 98/39027.

The following examples are intended for illustration purposes only, and should not be construed as limiting the scope of the invention in any way.

EXAMPLE 1

Ang-2 Expression in Pathological and Normal Tissue

Ang-2 expression was examined in normal and pathological tissue using in situ hybridization. Fragments of the human (Genbank Accession Number: AF004327, nucleotides 1274-1726) and murine (Genbank Accession Number: AF004326, nucleotides 1135-1588) Ang-2 sequences were amplified by reverse transcriptase-PCR from human or murine fetal lung cDNA, cloned into the pGEM-T plasmid and verified by sequencing. $^{33}$P-labeled antisense RNA probes were transcribed from linearized plasmid templates using $^{33}$P-UTP and RNA polymerase. Blocks of formaldehyde-fixed, paraffin-embedded tissues were sectioned at 5 µm and collected on charged slides. Prior to in situ hybridization, tissues were permeabilized with 0.2M HCL, followed by digestion with Proteinase K, and acetylation with triethanolamine and acetic anhydride. Sections were hybridized with the radio labeled probe overnight at 55° C. then subjected to RNase digestion and a high stringency wash in about 0.1×SSC at 55° C. Slides were dipped in Kodak NTB2 emulsion, exposed at 4° C. for 2-3 weeks, developed, and counterstained. Sections were examined with dark field and standard illumination to allow simultaneous evaluation of tissue morphology and hybridization signal.

The results indicated that in the normal postnatal human, Ang-2 expression is restricted to the few tissues containing angiogenic vasculature, such as the ovary, placenta, and uterus. No Ang-2 expression was detectable in normal adult human heart, brain, kidney, liver, lung, pancreas, spleen, muscle, tonsil, thymus, appendix, lymph node, gall bladder, prostate or testis. In five-week-old mouse (but not adult monkey or human), kidneys displayed prominent Ang-2 expression in the vasa recta. To determine whether this expression was a remnant of embryonic development, this experiment was repeated on kidneys derived from mice ranging in age up to one-year-old using the murine Ang-2 probe and conditions described above. Ang-2 expression was observed to decrease during post-natal development, but was still evident in kidneys of one-year-old mice.

Ang-2 expression was also detected in virtually all tumor types tested, including, primary human tumors such as colon carcinoma (5 cases), breast carcinoma (10 cases), lung carcinoma (8 cases), glioblastoma (1 case), metastatic human tumors such as breast carcinoma (2 cases), lung carcinoma (2 cases) and ovarian carcinoma (2 cases) which had metastized to brain, and rodent tumor models such as C6 (rat glioma), HT29 (human colon carcinoma), Colo-205 (human colon carcinoma), HCT116 (human colon carcinoma), A431 (human epidermoid carcinoma), A673 (human rhabdomyosarcoma), HT1080 (human fibrosarcoma), PC-3 (human prostate carcinoma), B16F10 (murine melanoma), MethA (murine sarcoma), and Lewis lung carcinoma mets. Additionally, Ang-2 expression was detected in neovessels growing into a Matrigel plug in response to VEGF and in a mouse hypoxia model of retinopathy of prematurity.

EXAMPLE 2

Production of Recombinant mAng-2 Protein and Rabbit Polyclonal anti-Ang-2 Antiserum Full length, His-tagged murine Ang-2 cDNA was obtained by PCR (Clontech Advantage PCR Kit, Cat.# K1905-01) from a murine 15-day embryo cDNA library (Marathon-Ready-cDNA, Cat.# 7459-1, Clonetech, Inc.) using PCR primers for full length human Ang-2. The PCR product was ligated into a CMV promoter expression vector, and the resultant plasmid was transfected into HT1080 human fibrosarcoma cells (obtained from ATCC) using FuGENE6 Transfection Reagent (Roche, Cat. #1814443). Stable clones were isolated by G418 selection. Anti-His tag ELISAs and Western blotting were used to screen for mAng-2-his expressing clones.

Recombinant mAng-2 polypeptide was purified from conditioned media (C.M.) of these cells. The C.M. containing mAng-2-His was purified by a two-step chromatography protocol. Briefly, the conditioned media was titrated to pH 8.9 by adding Tris buffer pH 9.5 to about 20 mM final concentration. Additionally, the detergent CHAPS was added to about 5 mM final concentration. The C.M. was then applied directly to an anion exchange column Q-sepharose ff (Pharmacia). The column was then washed with about 10 mM Tris pH 8.0 containing about 50 mM NaCl. Recombinant mAng-2-His was eluted in a single step using 10 mM Tris pH 8.0 containing about 350 mM NaCl and about 5 mM CHAPS.

The eluate from the Q-sepharose column was adjusted to about 4 mM imidazole, and applied to an immobilized metal affinity column (Ni-NTA superflow [Qiagen]). The bound protein was eluted with PBS containing about 5 mM CHAPS and about 100 mM imidazole. The eluate was then concentrated to approximately 1.0 mg/ml, followed by dialysis against PBS. The purity of mAng-2-His was greater than 90 percent as measured by SDS-PAGE Coomassie staining.

Rabbits were immunized with about 0.2 mg mAng-2/injection in an attempt to produce antibodies. Rabbits were injected with about 1 mL Hunter's TiterMax® (Sigma) and mAng-2 at a ratio of 1:1. Four weeks later, each rabbit received a repeat injection or booster; two weeks after that, they received their next booster, and at week seven, sera were drawn and evaluated for titer against mAng-2. If the serum titer was high, 50 mL production bleeds were drawn on a weekly basis for six consecutive weeks. However, if serum titer was low, rabbits were given an additional booster, and 50 mL production bleeds were drawn on a weekly basis for six consecutive weeks, beginning at week 9. After six consecutive production bleeds, rabbits were allowed to rest for six weeks. If more sera were required, the rabbits were boosted again one month after the last production bleed.

Using the Neutralization ELISA (described infra), anti-mAng-2 rabbit polyclonal antisera from two rabbits, 5254 and 5255, were observed to neutralize the mAng-2:Tie2 interaction.

EXAMPLE 3

Molecular Assays to Evaluate Ang-2 Antibodies

Molecular assays (Affinity ELISA, Neutralization ELISA and BIAcore) were developed to assess direct antibody binding to Ang-2 and related family members, and the effect of antibodies on the Ang-2:Tie2 interaction. These in vitro and cell-based assays are described as follows.

A. Affinity ELISA

For the initial screening of candidate anti-Ang-2 antibodies, purified human Ang-2 (R and D Systems, Inc; catalog number 623-AN; Ang-2 is provided as a mixture of 2 truncated versions) or murine Ang-2 polypeptide (prepared as described above) were used. For confirmatory binding assays, human Ang-2 was obtained from conditioned media of human 293T cells transfected with full length human Ang-2 DNA and cultured in serum free DMEM containing about 50 micrograms per ml of bovine serum albumin (BSA).

Using microtiter plates, approximately 100 microliters per well of Ang-2 was added to each well and the plates were incubated about 2 hours, after which the plates were washed with phosphate buffered saline (PBS) containing about 0.1 percent Tween-20 four times. The wells were then blocked using about 250 microliters per well of about 5 percent BSA in PBS, and the plates were incubated at room temperature for about 2 hours. After incubation, excess blocking solution was discarded, and about 100 microliters of candidate anti-Ang-2 antibody was added to each well in a dilution series starting at a concentration of about 40 nanomolar and then serially diluting 4-fold in PBS containing about 1 percent BSA. The plates were then incubated overnight at room temperature. After incubation, plates were washed with PBS containing about 0.1 percent Tween-20. Washing was repeated four additional times, after which about 100 microliters per well of goat anti-human IgG(Fc)-HRP (Pierce Chemical Co., catalog # 31416) previously diluted 1:5000 in PBS containing 1 percent BSA (bovine serum albumin) was added. Plates were incubated approximately 1 hour at room temperature. Plates were then washed five times in PBS containing about 0.1 percent Tween-20, after which about 100 microliters per well of TMB (3,3',5,5'-Tetramethylbenzidine Liquid Substrate System; Sigma chemical Company, St. Louis, Mo., catalog number T8665) substrate was added and plates were incubated about 5-15 minutes until blue color developed. Absorbance was then read in a spectrophotomer at about 370 nm.

B. Neutralization ELISA

Microtiter plates to which human Ang-2 polypeptide was bound were prepared as described for the Affinity ELISA. Candidate anti-Ang-2 antibodies were prepared in serial dilutions as described for the Affinity ELISA above in a solution of PBS containing about 1 percent BSA and about 1 nM Tie2 (provided as a Tie2-Fc molecule where the Tie2 portion contains only the soluble extracellular portion of the molecule; R and D Systems, catalog number 313-TI). After about 100 microliters of the antibody/Tie2 solution was added to each well, the plates were incubated overnight at room temperature, and then washed five times in PBS containing about 0.1 percent Tween-20. After washing, about 100 microliters per well of anti-Tie2 antibody (Pharmingen Inc., catalog # 557039) was added to a final concentration of about 1 microgram per ml and the plates were incubated about 1 hour at room temperature. Next, about 100 microliters per well of goat anti-mouse-IgG-HRP (Pierce Chemical CO., catalog # 31432) was added at a dilution of 1:10,000 in PBS containing about 1 percent BSA. Plates were incubated at room temperature for about 1 hour, after which they were washed five times with PBS containing about 0.1 percent Tween-20. About 100 microliters per well of TMB substrate (described above) was then added and color was allowed to develop. Absorbance was then read in a spectrophotomer at 370 nm.

C. Affinity BIAcore

An affinity analysis of each candidate Ang-2 antibody was performed on a BIAcore®2000 (Biacore, Inc., Piscataway, N.J.) with PBS and 0.005 percent P20 surfactant (BIAcore, Inc.) as running buffer. Recombinant Protein G (Repligen, Needham, Mass.) was immobilized to a research grade CM5 sensor chip (Biacore, Inc.) via primary amine groups using the Amine Coupling Kit (Biacore, Inc.) according to the manufacturer's suggested protocol.

Binding assays were carried out by first attaching about 100 Ru of each candidate anti-Ang-2 antibody to the immobilized Protein G, after which various concentrations (0-100 nM) of huAng-2 or mAng-2 were then injected over the bound antibody surface at a flow rate of about 50 ul/min for about 3 minutes. Antibody binding kinetics including $k_a$ (association rate constant), $k_d$ (dissociation rate constant) and $K_D$ (dissociation equilibrium constant) were determined using the BIA evaluation 3.1 computer program (BIAcore, Inc.). Lower dissociation equilibrium constants indicated greater affinity of the antibody for Ang-2.

EXAMPLE 4

Production of Fully Human Ang-2 Antibodies by Phage Display

Fully human Ang-2 antibodies were generated by panning a Target Quest Phage Display Fab library (Target Quest, Inc.) against a human Ang-2 polypeptide (R and D Systems Inc., catalog 623-AN), according to the following protocol.

Human Ang-2 was immobilized on the surface of polystyrene magnetic beads by two methods: (1) direct coating of Ang-2 at 50 ug/ml at 4C overnight; and (2) indirect capture of Ang-2 by goat anti-Ang-2 antibody at 50 ug/ml at 4C overnight. The bead surface was blocked by 2% milk in PBS (MPBS). The human Fab phage library was pre-selected to remove phage clones reactive to uncoated magnetic beads or the goat anti-Ang-2 antibody. Ang-2-coated magnetic beads were then incubated with library phage at room temperature for 1.5 hours. After the phage binding step, the surface was washed 6 times with MPBS containing about 0.1 percent Tween 20, followed by washing 6 times with PBS containing about 0.1 percent Tween 20, followed 2 times with PBS. The bound phage were eluted first with about 100 ug/ml human Tie2-Fc (R and D Systems, Minneapolis, Minn.), and then with about 100 mM triethanolamine. Eluted phage were infected into E. coli TG1 cells, amplified, and rescued for the next round of screening. Selection pressure was increased in successive rounds by incorporating more stringent washes and reducing the number of input phage. After 3 rounds of selection, 18 unique, Ang-2-binding Fab clones were identified, virtually all of which recognized human Ang-2, mouse Ang-2, and rat Ang-2 as measured using the ELISA affinity assay described above. Approximately ten percent of these phage also bound human Ang-1. These clones were converted into IgG1 antibodies as described below.

To obtain additional unique phage, a second round of screening was conducted using the same library but a slightly different protocol. In this protocol, human Ang-2 was plated in NaHCO3 buffer at pH 9.6 in Nunc maxisorp immunotubes at about 4 C. overnight. Ang-2 was plated at about 1.5, 0.74, and 0.3 ug/ml for panning rounds 1, 2, and 3, respectively. The immunotube surface was blocked using about 2 percent milk in PBS (MPBS), before it was incubated with about 2 trillion phage particles (about 50 copies of each unique phage in the library) from the same phage display library referred to above (Target Quest) in about 4 ml of 2% MPBS. After the phage incubation step, the surface was washed 20 times with PBS plus about 0.1 percent Tween 20, followed 20 times with PBS. The bound phage were eluted using 1 uM hAng-2 or 1 uM human Tie2 (R and D Systems, described above). Eluted phage were infected into E. coli TG1 cells (provided with the phage library), amplified, and rescued for the next round of screening. Sixteen unique, Ang-2-binding Fab clones were identified by PCR amplification of all phage to which hAng-2 or Tie2 bound, and these clones were analyzed by restriction digestion. The DNA of each clone was sequenced.

The sequence coding for the variable region of each heavy chain from each phage was amplified with complementary primers. The primers were designed to incorporate a HindIII site, XbaI site, Kozak sequence and a signal sequence (translated peptide is NDMRVPAQLLGLLLLWLRGARC; SEQ ID NO: 69) onto the 5' end of the variable region, while a BsmBI site was added onto the 3' end of the PCR product. As an example of how heavy chains were cloned, the template phage DNA for clone 544 (Seq ID No. 19) was amplified using primers 2248-21 (GTG GTT GAG AGG TGC CAG ATG TCA GGT CCA GCT GGT GCA G; SEQ ID NO: 70) which added the last 7 amino acids of the signal sequence and 2502-31 (ATT ACG TCT CAC AGT TCG TTT GAT CTC CAC; SEQ ID NO: 71) which added the BsmBI site onto the end of the variable region. The resulting product was amplified by primers 2148-98 (CCG CTC AGC TCC TGG GGC TCC TGC TAT TGT GGT TGA GAG GTG CCA GAT; SEQ ID NO: 72) which added nine amino acids to the signal peptide (AQLLGLLLL; SEQ ID NO: 73) and 2502-31, and then 2489-36 (CAG CAG AAG CTT CTA GAC CAC CAT GGA CAT GAG GGT CCC CGC TCA GCT CCT GGG; SEQ ID NO: 74) and 2502-31. Primer 2489-36 added, from 5' to 3', the HindIII site, XbaI site, Kozak sequence, and the first 6 amino acids of the signal sequence. The PCR products were digested with XbaI and BsmBI, and then cloned into a mammalian expression vector containing the human IgG1 constant region. This vector contains an SV40 promoter and DHFR selection.

Light chains from each phage were either kappa or lambda class. For each light chain, complementary primers were designed to add, from 5' to 3', a HindIII site, an XbaI site, Kozak sequence and signal sequence (set forth above). Those chains which had error-free coding regions were cloned as full-length products. As an example, the light chain from phage clone 536 (Seq ID NO. 11) was amplified as a full length coding region using primers 2627-69 (GTG GTT GAG AGG TGC CAG ATG TGA CAT TGT GAT GAC TCA GTC TCC; SEQ ID NO: 75), which added the last seven amino acids of the signal sequence, and primer 2458-54 (CTT GTC GAC TTA TTA ACA CTC TCC CCT GTT G; SEQ ID NO: 76), which added a SalI site after the stop codon. This PCR product was then amplified as previously stated with additional 5' primers, 2148-98 and 2489-36 respectively, paired with primer 2458-54, to finish addition of the signal sequence and cloning sites. The full-length light chains were cloned as XbaI-SalI fragments into the mammalian expression vector described above.

Certain lambda clones had errors in their constant regions when compared to natural human constant region sequence. To correct for these discrepancies, overlap PCR was performed using DNA coding for a perfect lambda constant region and the phage derived variable region. These clones were also cloned as XbaI-SalI fragments as described above.

Where kappa variable regions were cloned separately from their constant regions, a BsmBI site was added to the 3' end of the PCR product. After digestion of the PCR product with XbaI and BsmBI, the kappa chain variable region was cloned into an expression vector containing the human kappa constant region.

The paired light and heavy chain constructs from each converted phage were co-transfected into CHO cells using the Calcium Phosphate Transfection Kit (Invitrogen Corp.) generally according to the manufacturer's suggested protocol. Media was changed 14-16 hours post transfection, and the cells were passaged into tissue culture dishes for selection after about 48 hours per the manufacturer's recommendations. Transfected cells were isolated by HT selection for approximately 3 weeks, at which time transfected CHO cell colonies were trypsinzed and combined into a "pool" of transfected cells.

Small-scale conditioned media was collected after 48 hours and assayed for antibody production by Western blot analysis using either anti-human Fc antibody, anti-human kappa antibody, or anti-human lambda antibody. The selected cell populations were then passaged under selective pressure using standard tissue culture sterile technique until enough cells were obtained to seed four 850 cm$^2$ roller bottles with $2\times10^7$ viable cells each, and to prepare frozen stock cell lines using DMSO. After seeding, the cells were maintained in roller bottles with about 10 percent serum containing DMEM medium (Gibco/BRL, Inc) supplemented with glutamine and non-essential amino acids. Cells were maintained for two to three days until a cell confluency of approximately 80% was reached. At this point the media in the roller bottles was switched to a serum free media mixture (50 percent DMEM, 50 percent F12, Gibco) supplemented with glutamine and non-essential amino acids. Conditioned media was harvested after seven days, with fresh serum-free medium being added for one or two additional harvests.

Antibodies were purified by Protein G affinity chromatography directly from conditioned medium, using standard procedures. Elution from the Protein G column was accomplished using low pH (about pH 3) buffer, after which the eluted antibody protein was neutralized using 1M Tris, pH 8.5, and then concentrated using 10 kD molecular weight cutoff centrifugal concentrators. The concentrated antibody stock was then buffer exchanged into PBS.

Thirty-one antibodies have been created, and each consists of two heavy chains and 2 light (kappa or lambda) chains as designated in the following Table 2.

TABLE 2

| Antibody Heavy Chain | Antibody Light Chain |
|---|---|
| 526 HC* | 526 kappa |
| 528 HC* | 528 lambda |
| 531 HC* | 531 lambda |
| 533 HC* | 533 lambda |
| 535 HC* | 535 lambda |
| 536 HC* | 536 kappa |
| 537 HC* | 537 lambda |
| 540 HC* | 540 lambda |
| 543 HC* | 543 kappa |
| 544 HC* | 544 kappa |
| 545 HC* | 545 lambda |
| 546 HC* | 546 lambda |
| 551 HC* | 551 kappa |
| 553 HC* | 553 kappa |
| 555 HC* | 555 kappa |
| 558 HC | 558 kappa |
| 559 HC | 559 lambda |
| 565 HC* | 565 kappa |
| F1-C6 HC | F1-C6 lambda |
| FB1-A7 HC | FB1-A7 lambda |
| FD-B2 HC | FD-B2 lambda |
| FE-B7 HC | FE-B7 kappa |
| FJ-G11 HC | FJ-G11 kappa |
| FK-E3 HC | FK-E3 kappa |
| G1D4 HC* | G1D4 lambda |
| GC1E8 HC | GC1E8 lambda |
| H1C12 HC | H1C12 lambda |
| IA1-1E7 HC | IA1-1E7 kappa |
| IF-1C10 HC | IF-1C10 lambda |
| IK-2E2 HC | IK-2E2 lambda |
| IP-2C11 HC | IP-2C11 kappa |

*Tested for binding to hAng-2, mAng-2, and hAng-1 as described herein.

The following four tables set forth the sequences and SEQ ID NOs. of the heavy and light (kappa and lambda) chains of the 31 anti-Ang-2 antibodies converted from phage to full length IgG1 antibodies. The complementarity-determining regions (CDRs) of the monoclonal antibodies were predicted using the VBASE database which uses the technique described by Kabat et al in: Sequences of Proteins of Immunological Interest (NIH Publication No. 91-3242; U.S. Dept. Health and Human Services, 5$^{th}$ ed.). Fab regions were aligned to sequences in the database with the closest germline sequence and then visually compared with such sequences. The CDRs for each variable region (heavy or light chain) are set forth in Table 7.

TABLE 3

Heavy Chain Variable Regions

| Antibody HC | Sequence |
|---|---|
| 526 HC (SEQ ID NO. 1) | EVQLVESGGGVVQPGRSLRLSCAASGFTFSSYGM HWVRQAPGKGLEWVSAISGSGGSTYYADSVKGRF TISRDNAKNSLYLQMNSLRAEDTAVYYCARDLLD YDILTGPYAYWGQGTLVTVSS |
| 528 HC (SEQ ID NO. 3) | QVQLVQSGAEVKKPGSSVKVSCKASGGTFSSYAI SWVRQAPGQGLEWMGGIIPIFGTANYAQKFQGRV TITADESTSTAYMELSSLRSEDTAVYYCARGVVG DFDWLSFFDYWGQGTLVTVSS |

TABLE 3-continued

Heavy Chain Variable Regions

| Antibody HC | Sequence |
|---|---|
| 531 HC (SEQ ID NO. 5) | EVQLVQSGAEVKKPGSSVKVSCKASGGTFSSYAI SWVRQAPGQGLEWMGGIIPILGIANYAQKFQGRV TITADKSTNTAYMELTSLTSDDTAVYYCARDRED TAMVFNYWGQGTLVTVSS |
| 533 HC (SEQ ID NO. 7) | EVQLVQSGGGVVQPGRSLRLSCAASGFTFSSYGM HWVRQAPGKGLEWVSYISSSGSTIYYADSVKGRF TISRDNAKNSLYLQMNSLRAEDTAVYYCARDLLD YDILTGYGYWGQGTLVTVSS |
| 535 HC (SEQ ID NO. 9) | QVQLVQSGAEVKKPGSSVKVSCKASGGTFSSYAI SWVRQAPGQGLEWMGGIIPIFGTANYAQKFQGRV TITADKSTSTAYMELSSLRSEDTAVYYCAAFSPF TETDAFDIWGQGTMVTVSS |
| 536 HC (SEQ ID NO. 11) | EVQLVQSGGGVVQPGRSLRLSCAASGFTFSSYGM HWVRQAPGKGLEWVSYISSSGSTIYYADSVKGRF TISRDNAKNSLYLQMNSLRAEDTAVYYCARDLLD YDILTGYGYWGQGTLVTVSS |
| 537 HC (SEQ ID NO 13) | QVQLVQSGAEVKKPGSSVKVSCKASGGTFSSYAI SWVRQAPGQGLEWMGGIIPILGIANYAQKFQGRV TITADKSTSTAYMELSGLGSEDTAVYYCARGSSD AAVAGMWGQGTLVTVSS |
| 540 HC (SEQ ID NO. 15) | QVQLVQSGAEVKKPGSSVKVSCKASGGTFSSYAI SWVRQAPGQGLEWMGGIIPILGIANYAQKFQGRV TITADKFTSTAYMELSSLGSEDTAVYYCARAVPG TEDAFDIWGQGTMVTVSS |
| 543 HC (SEQ ID NO. 17) | QVQLVQSGAEVKKPGSSVKVSCKASGGTFSSYAI SWVRQAPGQGLEWMGRIIPILGIANYAQKFQGRV TITADKSTSTAYMELSSLRSEDTAVYYCARPYYD FWSGPGGMDVWGQGTTVTVSS |
| 544 HC (SEQ ID NO. 19) | QVQLVQSGAEVKKPGASVKVSCKASGGTFSSYAI SWVRQAPGQGLEWMGGIIPIFGTANYAQKFQGRV TITADESTSTAYMELSSLRSEDTAVYYCARFESG YWGDAFDIWGQGTMVTVSS |
| 545 HC (SEQ ID NO. 21) | QVQLQESGGGVVQPGRSLRLSCAASGFTFSSYGM HWVRQAPGKGLEWVAVISYDGSNKYYADSVKGRF TISRDNSKNTLYLQMNSLRAEDTAVYYCAKGPVD FDYGDYAIDYWGQGTLVTVSS |
| 546 HC (SEQ ID NO. 23) | EVQLVDSGGGLVQPGGSLRLSCAASGFTFSSYAM SWVRQAPGKGLEWVSAISGSGGSTYYADSVKGRF TISRDNSKNTLYLQMNSLRAEDTAVYYCAKETIS FSTFSGYFDYWAQGTLVTVSS |
| 551 HC (SEQ ID NO. 25) | QVQLVQSGAEVKKPGSSVKVSCKASGGTFSSYAI SWVRQAPGQGLEWMGGIIPIFGTANYAQKFQGRV TITADESTSTAYMELSSLRSEDTAVYYCARGYDF WSGYSLDAFDIWGQGTMVTVSS |
| 553 HC (SEQ ID NO. 27) | QVQLVQSGAEVKKPGASVKVSCKASGYTFTSYAM HWVRQAPGQRLEWMGWINAGNGNTKYSQKFQGRV TITRDTSASTAYMELSGLRSEDTAVYYCARGVDD YGGNSWAFDIWGQGTMVTVSS |
| 555 HC (SEQ ID NO. 29) | QVQLESGGGVVQPGRSLRLSCAASGFTFSSYAM HWVRQAPGKGLEWVAVISYDGSNKYYADSVKGRF TISRDNSKNTLYLQMNSLRAEDTAVYYCARSASD HYYDSSGYYSDAFDIWGQGTMVTVSS |
| 558 HC (SEQ ID NO. 31) | QVQLQQWGAGLLKPSETLSLTCAVYGGSFSGYYW SWIRQSPGKGLEWIGEINHSGSTNFNPSLKSRIT ISVDTSNNQFSLKLSSVTAADTAAYYCARGHDWG MGIGGAAYDIWGQGTMVTVSS |
| 559 HC (SEQ ID NO. 33) | QVQLVQSGAEVKKPGASVKVSCKVSGYTLTESSM HWVRQAPGKGLEWMGGFDPEHGETIYAQKFQGRL TMTEDTSTDTAYMELSSLRSEDTAVYFCARGVQV TSGYHYFDHWGQGTLVTVSS |

TABLE 3-continued

Heavy Chain Variable Regions

| Antibody HC | Sequence |
|---|---|
| 565 HC<br>(SEQ ID NO. 35) | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARSPIYYDILTGIDAFDIWGQGTMVTVSS |
| F1-C6 HC<br>(SEQ ID NO. 37) | QVQLVQSGAEVKKPGSSVKVSCKASGGTFSSYAISWVRQAPGQGLEWMGRIIPILGIANYAQKFQGRVTITADKSTSTAYMELSSLRSEDTAVYYCARDPIPSGWYFDLWGRGTLVTVSS |
| FB1-A7 HC<br>(SEQ ID NO. 39) | QVQLVESGGGLVKPGRSLRLSCAASGFTFSSYGMHWVRQAPGKGLEWVAVIWYDGSNKYYADSVKGRFTISRDNSKNTLYLQMNSLRAEDTAVYYCAREVGNYYDSSGYGWGQGTLVTVSS |
| FD-B2 HC<br>(SEQ ID NO. 41) | QVQLQQSGPGLVKPSQTLSLTCAISGDTVSSNSAAWNWIRQSPSRGLEWLGRTYYRSKWYSDYAVSLRGRITINLDTDTSKNQFSLQLNSVTPEDTAVYYCARDRGGYIDSWGQGTLVTVSS |
| FE-B7 HC<br>(SEQ ID NO. 43) | EVQLVESGGGLGQPGGSLRLSCAATGFSLDDYEMNWVRQAPGRGLEWVSYIIGSGKTIFYADSVKGRFTISRDNGKNSVYLQMNSLRAEDTAIYYCARGGGSAYYLNTSDIWGQGTMVTVSS |
| FJ-G11 HC<br>(SEQ ID NO. 45) | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARDRGIAARSAYYYGMDVWGQGTTVTVSS |
| FK-E3 HC<br>(SEQ ID NO. 47) | QVQLVQSGAEVKKPGASVKVSCKASGYTFTSYDLNWVRQASGQGLEWMGWMNPTSGNTGYAQKFQGRITMTRNTSISTAYMELRSLRSDDTAVYYCARDPPSGGWEFDYWGQGTLVTVSS |
| G1D4 HC<br>(SEQ ID NO. 49) | QVQLVQSGAEVKKPGSSVKVSCKASGGTFSSHAISWVRQAPGQGLEWMGRIIPILGIANYAQKFQGRVTITADESTSTAYMELSSLRSEDTAVYYCATSRLEWLLYLDYWGQGTLVTVSS |
| GC1E8 HC<br>(SEQ ID NO. 51) | QVQLVQSGAEVKKPGASVKVSCKASGYTFTSYGISWVRQAPGQGLEWMGWISAYNGNTNYAQKLQGRVTMTTDTSTSTAYMEVRSLRSDDTAVYYCARGGSPYGGYAYPFDYWGQGTLVTVSS |
| H1C12 HC<br>(SEQ ID NO. 53) | EVQLVESGGGVVQPGRSLRLSCAASGFTFSSYGMHWVRQAPGKGLEWVSYISSSGSTIYYADSVKGRFTISRDNAKNSLYLQMNSLRAEDTAVYYCARDLLDYDILTGYGYWGQGTLVTVSS |
| 1A1-1E7 HC<br>(SEQ ID NO. 55) | QVQLQQWGAGLLKPSETLSLTCAVYGGSFSGYYWSWIRQSPGKGLEWIGEINHSGSTNFNPSLKSRITISVDTSNNQFSLKLSSVTAADTAVYYCARGHDWGMGIGGAAYDIWGQGTMVTVSS |
| IF-1C10 HC | QVQLVESGGGLVQPGGSLRLSCAASGFTFFSTYAMT |

TABLE 3-continued

Heavy Chain Variable Regions

| Antibody HC | Sequence |
|---|---|
| (SEQ ID NO. 57) | WVRQAPGKGLEWVSVIRSNGGTDYADFVKGRFTISRDNSKNTLYLQMNGLRAEDTAVYYCMTDYYWGQGTLVTVSS |
| IK-2E2 HC<br>(SEQ ID NO. 59) | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKETISFSTFSGYFDYWGQGTLVTVSS |
| IP-2C11 HC<br>(SEQ ID NO. 61) | QVQLVQSGAEVKKPGASVKVSCKASGYTFTSYDINWVRQATGQGLEWMGWMNPNSGNTGYAQKFQGRVTMTRNTSISTAYMELSSLRSEDTAVYYCAKEIAVAGTRYGMDVWGQGTTVTVSS |

TABLE 4

Kappa Chain Variable Regions

| Antibody LC | Sequence |
|---|---|
| 526 kappa<br>(SEQ ID NO. 2) | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPPTFGGGTKVEIK |
| 536 kappa<br>(SEQ ID NO. 12) | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQGTHWPPTFGQGTKLEIK |
| 543 kappa<br>(SEQ ID NO. 18) | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFGGGTKVEIK |
| 544 kappa<br>(SEQ ID NO. 20) | DIVMTQSPLSLPVTPGEPASISCRSSQSLLHSNGYNYLNWYLQKPGQSPQILIYLGSNRASGVPDRFSGSGSGTDFTLKISRVEAEDVGVYYCMQGLQTPPTFGQGTKLEIK |
| 551 kappa<br>(SEQ ID NO. 26) | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFGGGTKVEIK |
| 553 kappa<br>(SEQ ID NO. 28) | DIVMTQSPLSLPVTPGEPASISCRSSQSLLHSNGYNYLDWYLQKPGQSPQLLIYLGSNRASGVPDRFTGSGSATDFTLRISRVEAEDVGVYYCMQALQTPLTFGGGTKVEIK |
| 555 kappa<br>(SEQ ID NO. 30) | DIVMTQSPLSLPVTPGEPASISCRSSQSLLHSNGYNYLDWYLQKPGQSPQLLIYLASNRASGVPDRFSGSGSGTDFTLRISRVEAEDVGVYYCMQTLQIPITFGPGTKVDIK |
| 558 kappa<br>(SEQ ID NO. 32) | EIVLTQSPGTLSLSPGERATLSCRASQSVSSSSLAWYQQKPGQAPRLLVYAASSRATGIPDRFSGSGSGTDFTLTISRLEPEDFAVYYCQHYGSSPRTFGQGTKVEIK |
| 565 kappa<br>(SEQ ID NO. 36) | EIVLTQSPGTLSLSPGERATLSCRASQSVSSSSLAWYQQKPGQAPRLLVYAASSRATGIPDRFSGSGSGTDFTLTISRLEPEDFAVYYCQHYGSSPRTFGQGTKVEIK |

TABLE 4-continued

Kappa Chain Variable Regions

| Antibody LC | Sequence |
|---|---|
| FE-B7 kappa (SEQ ID NO. 44) | DIVMTQSPLSLPVTPGEPASISCRSSQSLLHSKG DNYLDWYLQKPGQSPQLLIYLGSHRASGVPDRFS GSGSGTDFTLKISRVEAEDVGVYYCMQALQTPLT FGGGTKVEIK |
| FJ-G11 kappa (SEQ ID NO. 46) | DIVMTQTPLSLPVTPGEPASISCRSSQSLLDSDD GKTYLDWYLQRPGQSPQLLMYTTSSRASGVPDRF SGSGSGTDFTLKISRVEAEDVGVYYCMQATQFPY TFGQGTKLEIK |
| FK-E3 kappa (SEQ ID NO. 48) | DIVMTQTPLSSTVTLGQPASISCRSSQSLVHEDG NTYLNWLHQRPGQPPRLLIYKISKRFSGVPDRFS GSGAGTDFTLKISRVEPEDVGVYYCMQSTRFPRT FGQGTKLEIK |
| IA1-1E7 kappa (SEQ ID NO. 56) | EIVLTQSPATLSLSPGERATLSCRASQSVSSSFL AWYQQKAGQAPRLLIYDTSTRATGIADRFSGSGS GTDFTLTISRLEAEDSAVYYCQQYDFSPLTFGGG TKVEIK |
| IP-2C11 kappa (SEQ ID NO. 62) | EIVLTQSPGTLSLSPGERATLSCRASQSISTFLA WYQQKPGQAPRLLIYDASNRATGIPGRFSGSGSG TDFTLTISNLEPEDFAVYYCQHRINWPLTFGGGT KVEIK |

TABLE 5

Lambda Chain Variable Regions

| Antibody LC | Sequence |
|---|---|
| 528 lambda (SEQ ID NO. 4) | SYELTQPPSVSVSPGQTASITCSGDKLGYTYTSW FQQKPGQSPVLVIFQDFKRPSGIPERFSGSNSGN TATLTISGTQAMDEADYYCQAWDSTTAVVFGTGT KVTVL |
| 531 lambda (SEQ ID NO. 6) | QSVLTQPPSVSAAPGQKVTVSCSGSSSNIGNNYV SWYQQLPGTAPKLLIYDNNKRPSGIPDRFSGSKS GTSATLGITGLQTDEADYYCGTWDSSLSAFWVF GGGTKLTVL |
| 533 lambda (SEQ ID NO. 8) | SYELTQPPSVSVSPGQTARITCSGDALPKQYAYW YQQKPGQAPVLVIYKDSERPSGIPERFSGSSSGT TVTLTISGVQAEDEADYYCQSADSSHVVFGGGTK LTVL |
| 535 lambda (SEQ ID NO. 10) | QSVLTQPPSVSAAPGQKVTISCSGSNSIGNNFV SWYQQLPGTAPKLLVYDNNKRPSGIPDRFSGSKS GTSATLGITGLQTGDEADYYCGTWDSSLSAAEVV FGGGTKLTVL |
| 537 lambda (SEQ ID NO. 14) | QSVLTQPPSVSAAPGQDVTISCSGNNSIGNNYV SWYQQVPGTAPKLLVYDNHKRPSGISDRFSGSKS DTSATLDITGLQPGDEADYYCGTWDTSLSANWVF GGGTKLTVL |
| 540 lambda (SEQ ID NO. 16) | QSVLTQPPSVSAAPGQKVTISCSGSSSNIGANYV SWYQQLPGTAPKLLIYNNNKRPSGIPDRFSGSKS DTSATLGITGLQTGDEADYYCGAWDSSLSASWVF GGGTKLTVL |
| 545 lambda (SEQ ID NO. 22) | QSVLTQPSSVSGAPGQRVTISCTGQSSNIGAGYD VHWYQQFPGRAPKLLIYGNSNRPSGVPDRFSGSK SGTSASLAITGLQPEDEADYYCQSYDSRLSGSVF GGGTKLTVL |
| 546 lambda (SEQ ID NO. 24) | QSVLTQPSSVSEAPRQRVTISCSGSASNIGANGV SWYHQVPGKAPRLLLSHDGLVTSGVPDRLSVSKS GTSASLAISGLHSDDEGDYYCAVWDDSLNAVVFG GGTKLTVL |

TABLE 5-continued

Lambda Chain Variable Regions

| Antibody LC | Sequence |
|---|---|
| 559 lambda (SEQ ID NO. 34) | QSALTQPPSASGSPGQSITISCTGTNSDIGSYPF VSWYQRHPGKAPKLLIYDVSNRPSGVSDRFSGSK SGNTASLTISGLQAEDEGDYYCSSFTMNSFVIFG GGTKLTVL |
| F1-C6 lambda (SEQ ID NO 38) | QSVLTQPPSVSEAPRQRVTISCSGSSSNIGNNAV NWYQQLPGKAPKLLIYYDDLLPSGVSDRFSGSKS GTSASLAISGLRSEDEADYYCATWDDSLSGWVFG GGTKLTVL |
| FB1-A7 lambda (SEQ ID NO 40) | NFMLTQPHSVSESPGKTVTISCTRSGGGIGSSFV HWFQQRPGSSPTTVIFDDNQRPTGVPDRFSAAID TSSSSASLTISGLTAEDEADYYCQSSHSTAVVFG GGTKLTVL |
| FD-B2 lambda (SEQ ID NO 42) | NFMLTQPHSVSESPGKTVTISCTRSSGSIATNYV QWYQQRPGSSPATVIYEDNQRPSGVPDRFSGSID TSSNSASLTISGLTTEDEADYFCQSYGDNNWVFG GGTKLTVL |
| G1D4 lambda (SEQ ID NO 50) | NFMLTQPHSVSESPGKTVIIPCTRSSGSIASNYV QWYQKRPGSAPSIVIYEDKQRPSGVPDRFSGSID SSSNSASLTISGLKTEDEADYYCQSYNSRGVMFG GGTKLTVL |
| GC1E8 lambda (SEQ ID NO 52) | NFMLTQPHSVLESAGKTVTISCTRSSGSIASNYV QWYQQRPGTSPTNVIFEDNQRPSGVPDRFSGSID SSSNSASLTISGLKTEDEADYFCQSYDSNIWVFG GGTKLTVL |
| H1C12 lambda (SEQ ID NO 54) | QSVLTQPPSVSAAPGQKVTISCSGSSSNIGNNYV SWYQHLPGTAPKLLIYGNTNRPSGVDRFSGSKS GTSASLAIAGLQAEDEADYYCQSYDSSLSGSLVF GGGTKLTVL |
| IF-1C10 lambda (SEQ ID NO 58) | NFMLTQPHSVSESPGKTVTISCTGSGGSIASNYV QWYQQRPGSAPTTVIYEDNQRPSGVPDRFSGSID SSSNSASLTISGLKTEDEADYYCQSYDSSTWVFG GGTKLTVL |
| IK-2E2 lambda (SEQ ID NO 60) | QSALTQPASVSGSPGQSITISCTGTSSDVGGYNY VSWFQQHPGKAPKLMIYKVNNRPSGLSNRFSGSQ SGNTASLTISGLQAEDEADYYCSSYTSSSTLGFG GGTKLTVL |

TABLE 6

Human Constant Regions (CR)

| Antibody CR | Sequence |
|---|---|
| Human lambda constant region 1 (SEQ ID NO. 63) | GQPKANPTVTLFPPSSEELQANKATLVCLISD FYPGAVTVAWKADSSPVKAGVETTKPSKQSNN KYAASSYLSLTPEQWKSHRSYSCQVTHEGSTV EKTVAPTECS |
| Human lambda constant region 2 (SEQ ID NO. 64) | GQPKAAPSVTLFPPSSEELQANKATLVCLISD FYPGAVTVAWKADSSPVKAGVETTTPSKQSNN KYAASSYLSLTPEQWKSHRSYSCQVTHEGSTV EKTVAPTECS |
| Human lambda constant region 3 (SEQ ID NO. 65) | GQPKAAPSVTLFPPSSEELQANKATLVCLISD FYPGAVTVAWKADSSPVKAGVETTTPSKQSNN KYAASSYLSLTPEQWKSHKSYSCQVTHEGSTV EKTVAPTECS |
| Human lambda constant region 7 (SEQ ID NO. 66) | GQPKAAPSVTLFPPSSEELQANKATLVCLVSD FYPGAVTVAWKADSSPVKVGVETTKPSKQSNN KYAASSYLSLTPEQWKSHRSYSCRVTHEGSTV EKTVAPAECS |

TABLE 6-continued

Human Constant Regions (CR)

| Antibody CR | Sequence |
|---|---|
| Human kappa constant region (SEQ ID NO. 67) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| Human IgG1 constant region (SEQ ID NO. 68) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |

TABLE 7

Complementarity-Determining Regions (CDRs) of Heavy Chains (HC) and Light Chains (LC) of Ang-2 Antibodies

| Antibody | CDR 1 Residues | CDR 2 Residues | CDR 3 Residues |
|---|---|---|---|
| Ab 526 HC | 26-36 | 50-66 | 96-113 |
| Ab 526 KC | 23-46 | 54-62 | 93-102 |
| Ab 528 HC | 26-36 | 50-66 | 96-113 |
| Ab 528 LC | 22-34 | 56-76 | 87-98 |
| Ab 531 HC | 26-36 | 50-66 | 96-110 |
| Ab 531 LC | 22-36 | 58-78 | 89-102 |
| Ab 533 HC | 26-36 | 50-66 | 96-112 |
| Ab 533 LC | 22-34 | 56-76 | 87-97 |
| Ab 535 HC | 26-36 | 50-66 | 96-111 |
| Ab 535 LC | 22-36 | 58-78 | 89-103 |
| Ab 536 HC | 26-36 | 50-66 | 96-112 |
| Ab 536 KC | 23-40 | 54-62 | 93-102 |
| Ab 537 HC | 26-36 | 50-66 | 96-109 |
| Ab 537 LC | 22-36 | 58-78 | 89-102 |
| Ab 540 HC | 26-36 | 50-66 | 96-110 |
| Ab 540 LC | 22-36 | 58-78 | 89-102 |
| Ab 543 HC | 26-36 | 50-66 | 96-113 |
| Ab 543 KC | 23-40 | 54-62 | 93-102 |
| Ab 544 HC | 26-36 | 50-66 | 96-111 |
| Ab 544 KC | 23-40 | 54-62 | 93-102 |
| Ab 545 HC | 26-36 | 50-66 | 96-113 |
| Ab 545 LC | 22-37 | 59-79 | 90-102 |
| Ab 546 HC | 26-36 | 50-66 | 96-113 |
| Ab 546 LC | 22-36 | 58-78 | 89-101 |
| Ab 551 HC | 26-36 | 50-66 | 96-114 |
| Ab 551 KC | 23-40 | 54-62 | 93-102 |
| Ab 553 HC | 26-36 | 50-66 | 96-113 |
| Ab 553 KC | 23-40 | 54-62 | 93-102 |
| Ab 555 HC | 26-36 | 50-66 | 96-118 |
| Ab 555 KC | 23-40 | 54-62 | 93-102 |
| Ab 558 HC | 26-36 | 50-65 | 95-113 |
| Ab 558 KC | 23-36 | 50-58 | 89-98 |
| Ab 559 HC | 26-36 | 50-66 | 96-112 |
| Ab 559 LC | 22-37 | 59-79 | 90-101 |
| Ab 565 HC | 26-36 | 50-66 | 96-115 |
| Ab 565 KC | 23-36 | 50-58 | 89-98 |
| Ab F1-C6 HC | 26-36 | 50-66 | 96-110 |
| Ab F1-C6 LC | 22-36 | 58-78 | 89-101 |
| Ab FB1-A7 HC | 26-36 | 50-66 | 96-112 |
| Ab FB1-A7 LC | 22-36 | 58-80 | 91-101 |
| Ab FD-B2 HC | 26-38 | 52-69 | 101-112 |
| Ab FD-B2 LC | 22-36 | 58-80 | 91-101 |
| Ab FE-B7 HC | 26-36 | 50-66 | 96-112 |
| Ab FE-B7 KC | 23-40 | 54-62 | 93-102 |
| Ab FJ-G11 HC | 26-36 | 50-66 | 96-115 |
| Ab FJ-G11 KC | 23-41 | 55-63 | 94-103 |
| Ab FK-E3 HC | 26-36 | 50-66 | 96-110 |
| Ab FK-E3 KC | 23-40 | 54-62 | 93-102 |
| Ab G1D4 HC | 26-36 | 50-66 | 96-110 |
| Ab G1D4 LC | 22-36 | 58-80 | 91-101 |
| Ab GC1E8 HC | 26-36 | 50-66 | 96-113 |
| Ab GC1E8 LC | 22-36 | 58-80 | 91-101 |
| Ab H1C12 HC | 26-36 | 50-66 | 96-112 |
| Ab H1C12 LC | 22-36 | 58-78 | 89-102 |
| Ab IA1-1E7 HC | 26-36 | 50-65 | 95-113 |
| Ab IA1-1E7 KC | 23-36 | 50-58 | 89-98 |
| Ab IF-1C10 HC | 26-37 | 51-66 | 96-102 |
| Ab IF-1C10 LC | 22-36 | 58-80 | 91-101 |
| Ab IK-2E2 HC | 26-36 | 50-66 | 96-113 |
| Ab IK-2E2 LC | 22-37 | 59-79 | 90-101 |
| Ab IP-2C11 HC | 26-36 | 50-66 | 96-112 |
| Ab IP-2C11 KC | 23-35 | 49-57 | 88-97 |

Seventeen of the antibodies and a negative control IgG1 (referred to as RDB1) were tested using affinity and neutralization ELISA (as described in Example 3 above) as well as the BIAcore neutralization assay to determine their affinity, neutralization, and specificity capabilities. The results are set forth below (Table 8) and were calculated using standard procedures.

TABLE 8

Ang-2 Antibody EC50s and IC50s

| Antibody | hAng-2 IC50 (nM) | hAng-2 EC50 (nM) | mAng-2 IC50 (nM) | mAng-2 EC50 (nM) | hAng-1 IC50 (nM) | hAng-1 EC50 (nM) |
|---|---|---|---|---|---|---|
| Ab 536 | 0 08 | 0.005 | 0 05 | 0 01 | 114 65 | 30 |
| Ab 565 | 0 26 | | 0 26 | | No inhibition | |
| Ab 546 | 0 37 | | 1 09 | | No inhibition | |
| Ab 543 | 0 51 | | 0 24 | | No inhibition | |
| Ab 533 | 0 3 | | 0 08 | | No inhibition | |
| Ab 537 | 0 56 | | 0 62 | | No inhibition | |
| Ab 540 | 0 70 | | 1 53 | | No inhibition | |
| Ab 544 | 0.97 | | 1.82 | | 23 32 | |
| Ab 545 | 1.04 | 0 02 | 1.30 | 0 05 | 8 31 | 2 |
| Ab 528 | 1.37 | | 0.73 | | No inhibition | |
| Ab G1D4 | 1 39 | | 0.60 | | 69 48 | |
| Ab 551 | 1 41 | | 2 88 | | No inhibition | |
| Ab 553 | 1 47 | | 1 41 | | No inhibition | |

TABLE 8-continued

Ang-2 Antibody EC50s and IC50s

| | hAng-2 | | mAng-2 | | hAng-1 | |
|---|---|---|---|---|---|---|
| Antibody | IC50 (nM) | EC50 (nM) | IC50 (nM) | EC50 (nM) | IC50 (nM) | EC50 (nM) |
| Ab 526 | 1 83 | | 0 27 | | 243 15 | |
| Ab 531 | 2 15 | | 1 67 | | No inhibition | |
| Ab 555 | 2.21 | | 1.76 | | No inhibition | |
| Ab 535 | 2 81 | | 2 45 | | No inhibition | |
| RDB1 | No inhibition | No binding | No inhibition | No binding | No inhibition | No binding |

Two antibodies, clone 536 and clone 545, were evaluated using the BIAcore analysis described above. Antibody binding was determined as described above for the BIAcore assay, with lower $K_D$s indicating greater affinities, and results are reported in the following Table 9.

TABLE 9

Antibody Affinities for hAng-2 and mAng-2

| | hAng-2 | | | mAng-2 | | |
|---|---|---|---|---|---|---|
| Ab | $K_D$ (nM) | $k_a$ (1/Ms) | $k_d$ (1/s) | $K_D$ (nM) | $k_a$ (1/Ms) | $k_d$ (1/s) |
| Ab 536 | 0.12 | $3.2 \times 10^5$ | $3.8 \times 10^{-5}$ | 0.15 | $6.2 \times 10^5$ | $9.5 \times 10^{-5}$ |
| Ab 545 | 1.2 | $3.3 \times 10^5$ | $3.9 \times 10^{-4}$ | 0.9 | $5.9 \times 10^5$ | $5.3 \times 10^{-4}$ |

EXAMPLE 5

Therapeutic Efficacy Studies using Anti-Ang-2 Antibodies

The pharmacokinetics of Protein-G purified rabbit anti-Ang-2 polyclonal antibodies were examined in mice. Twenty-four mice were treated with polyclonal anti-Ang-2 rabbit antibody (1 mg per mouse). Four treated animals were sacrificed at each of the following time points post-injection of antibody: 1 hour, 6 hours, 1 day, 3 days, 7 days, and 14 days.

The results indicated that total rabbit IgG had a circulatory half-life in serum of approximately 19 days, while the anti-Ang-2 IgG component of the total IgG had a half-life of approximately eight days.

To assess therapeutic efficacy, mice (10 animals/group) bearing A431 tumor xenografts were given 10 doses (about 10 mg IgG per mouse per dose) intraperitoneally of Protein G purified anti-mAng-2 polyclonal antibody on days 1, 5, 6, 7, 8, 12, 13, 14, 15, and 18 after xenografting. Tumor size was measured on days 7, 12, 15, 19, and 21. Body weight was measured on days 0, 7, 15, and 21, and was unaffected by treatment. Results indicated that the anti-Ang-2 polyclonal antibody inhibited the A431 tumor xenograft growth by about 50 percent with p=0.008 versus controls of non-immune purified polyclonal antiserum (10 mg IgG per mouse per dose) and vehicle (PBS) by repeated measures ANOVA.

To test the efficacy of the fully human monoclonal anti-Ang-2 antibodies in vivo, mice (10 animals/group) bearing A431 tumor xenografts were treated intraperitoneally with either anti-Ang-2 antibody clone 533, 537, or 544, or with negative controls of PBS or human IgG1-kappa. Dosing was about 420 ug protein per mouse for the first dose, about 140 ug protein per mouse for each of the next three doses, and about 55 ug protein per mouse for each of the next four doses, for a total of 8 doses per mouse. Tumor volumes and body weights were recorded twice weekly. At the end of the study, animals were sacrificed and their serum was collected for measuring antibody levels by ELISA. Tumors and a panel of normal tissues were collected from all groups.

Remarkable differences in tumor growth between the anti-Ang-2-treated and control groups were found as shown in FIG. 1. All three anti-Ang-2 treatments inhibited tumor growth as compared to controls (p<0.005 vs. hIgG1 control in all treatments using repeated measure ANOVA for all 3 antibodies). In contrast, tumors in control groups continued to grow at a much greater rate.

EXAMPLE 6

Epitope Mapping

Full-length (amino acids 1-495), N-terminal (amino acids 1-254) and C-terminal (amino acids 255-495) human Ang-2 (hAng-2) proteins were cloned into a CMV-driven mammalian expression vector with C-terminal 6×His tags. The three resultant constructs plus a vector control were transiently expressed into 293T cells. Conditioned media were then collected from the transfected cells, and the expression level of Ang-2 in the media was estimated by anti-6×his ELISA and Western blotting.

The binding epitope of anti-Ang-2 antibodies and peptibodies was determined by their ability to bind the three versions of human hAng-2 by ELISA according to the following protocol: a high-binding 96-well assay plate was coated with 100 μl of conditioned media per well, and incubated at 37° C. for 1 hour. Conditioned media was aspirated, and the plate was blocked with 200 μl per well of 5% BSA in PBS at room temperature for 1 hour. The blocking solution was then aspirated. 100 μl per well of antibody, peptibody, or Tie2-Fc was added at 1 μg/ml in 1% BSA in PBS, and incubated at room temperature for 1 hour. The wells were washed 4 times with 200 μl of 0.1% Tween in PBS. 100 μl per well of HRP-conjugated goat anti-human IgG or goat anti-mouse IgG were added, and incubated at room temperature for 45 minutes. The wells were then washed with 200 μl of 0.1% Tween in PBS 4 times. 100 μl per well of TMB substrate was then added. O.D. was read at 370 nm.

The results are set forth in FIG. 2A, FIG. 2B, and FIG. 2C.

What is claimed is:

1. An isolated antibody comprising a heavy chain and a light chain, wherein the heavy chain comprises a heavy chain variable region comprising CDR1, CDR2, and CDR3 of SEQ ID NO. 11, and wherein the light chain comprises a light chain variable region comprising CDR1, CDR2, and CDR3 of SEQ ID NO. 12, wherein the antibody binds angiopoietin-2 (Ang-2).

2. The antibody of claim 1, wherein the heavy chain variable region comprises SEQ ID NO. 11; and the light chain variable region comprises CDR1, CDR2, and CDR3 of SEQ ID NO. 12.

3. The antibody of claim 1, wherein the heavy chain variable region comprises CDR1, CDR2, and CDR3 of SEQ ID NO. 11; and the light chain variable region comprises of SEQ ID NO. 12.

4. The antibody of claim 1, wherein the heavy chain variable region comprises SEQ ID NO. 11, and the light chain variable region comprises SEQ ID NO. 12.

5. An isolated antibody comprising a heavy chain and a light chain, wherein the heavy chain comprises a heavy chain variable region comprising the amino acid sequence of SEQ ID NO: 11, wherein the antibody binds angiopoietin-2 (Ang-2).

6. An isolated antibody comprising a heavy chain and a light chain, wherein the light chain comprises a light chain variable region comprising the amino acid sequence of SEQ ID NO: 12, wherein the antibody binds angiopoietin-2 (Ang-2).

7. An isolated antibody comprising a heavy chain variable region comprising the amino acid sequence of SEQ ID NO: 11, or an antigen-binding fragment thereof, wherein the antigen-binding fragment comprises at least CDR1, CDR2, and CDR3 of SEQ ID NO. 11, and a light chain variable region comprising the amino acid sequence of SEQ ID NO: 12, or an antigen-binding fragment thereof, wherein the antigen-binding fragment comprises at least CDR1, CDR2, and CDR3 of SEQ ID NO. 12, wherein the antibody binds angiopoietin-2 (Ang-2).

8. An isolated antibody comprising:
   a. heavy chain framework regions, a heavy chain CDR1 region comprising CDR1 of SEQ ID NO. 11, a heavy chain CDR2 region comprising CDR2 of SEQ ID NO. 11, and a heavy chain CDR3 region comprising CDR3 of SEQ ID NO. 11; and
   b. light chain framework regions, a light chain CDR1 region comprising CDR1 of SEQ ID NO. 12, a light chain CDR2 region comprising CDR2 of SEQ ID NO. 12, and a light chain CDR3 region comprising CDR3 of SEQ ID NO. 12;

wherein the antibody binds angiopoietin-2 (Ang-2).

9. The antibody of claim 1, 5, 6, or 7 that is a polyclonal, monoclonal, chimeric, humanized, or fully human antibody.

10. The antibody of claim 9 that is a single chain antibody.

11. The antibody of claim 9, or 10, wherein the antibody is covalently attached to a molecule selected form the group consisting of a reporter group, a water soluble polymer, an Fc region, and a cytotoxic agent.

12. The antibody of claim 10, which is a single-chain Fv antibody.

13. The antibody of claim 10, which is a Fab antibody fragment.

14. The antibody of claim 10, which is a Fab' antibody fragment.

15. The antibody of claim 10, which is a (Fab')$_2$ antibody fragment.

16. A pharmaceutical composition comprising the isolated antibody of claim 9 and a pharmaceutically acceptable formulation agent.

17. A pharmaceutical composition comprising the antibody of claim 9 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,521,053 B2 | Page 1 of 1 |
| APPLICATION NO. | : 10/269805 | |
| DATED | : April 21, 2009 | |
| INVENTOR(S) | : Oliner | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 697 days Delete the phrase "by 697 days" and insert -- by 1,366 days --

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,521,053 B2 | Page 1 of 1 |
| APPLICATION NO. | : 10/269805 | |
| DATED | : April 21, 2009 | |
| INVENTOR(S) | : Jonathan Daniel Oliner | |

It is certified that error appears in the above-identified patent and that said Letters Patent is hereby corrected as shown below:

On the title page, in the Assignee Field (73), delete "Medarex, Inc., Princeton, NJ (US)".

Signed and Sealed this
Twenty-third Day of October, 2012

David J. Kappos
*Director of the United States Patent and Trademark Office*